US012584830B2

(12) United States Patent
Lee et al.

(10) Patent No.: US 12,584,830 B2
(45) Date of Patent: Mar. 24, 2026

(54) BLOOD STAINING PATCH, METHOD AND DEVICE FOR BLOOD TEST USING THE SAME

(71) Applicant: NOUL CO., LTD., Yongin-si (KR)

(72) Inventors: Dong Young Lee, Gyeonggi-do (KR);
Chan Yang Lim, Gyeonggi-do (KR);
Kyung Hwan Kim, Gyeonggi-do (KR);
Young Min Shin, Gyeonggi-do (KR);
Hyun Jeong Yang, Gyeonggi-do (KR)

(73) Assignee: NOUL CO., LTD., Yongin-si (KR)

( * ) Notice: Subject to any disclaimer, the term of this patent is extended or adjusted under 35 U.S.C. 154(b) by 12 days.

(21) Appl. No.: 18/160,985

(22) Filed: Jan. 27, 2023

(65) Prior Publication Data

US 2023/0194398 A1 Jun. 22, 2023

Related U.S. Application Data

(62) Division of application No. 16/079,271, filed as application No. PCT/KR2017/002030 on Feb. 23, 2017, now abandoned.

(Continued)

(30) Foreign Application Priority Data

Jun. 4, 2016 (KR) ........................ 10-2016-0069936
Jun. 4, 2016 (KR) ........................ 10-2016-0069937

(Continued)

(51) Int. Cl.
*G01N 1/31* (2006.01)
*B01L 3/00* (2006.01)
(Continued)

(52) U.S. Cl.
CPC ................ *G01N 1/312* (2013.01); *B01L 3/00*
(2013.01); *C07K 16/3061* (2013.01);
(Continued)

(58) Field of Classification Search
CPC .. B01L 3/00; B01L 3/505; G01N 1/30; G01N
1/31; G01N 1/312; G01N 15/06;
(Continued)

(56) References Cited

U.S. PATENT DOCUMENTS 555,270 A 2/1896 Taylor
3,870,146 A 3/1975 Greenfield et al.
(Continued)

FOREIGN PATENT DOCUMENTS

CN 1034617 8/1989
CN 1207171 2/1999
(Continued)

OTHER PUBLICATIONS

Becton, Dickinson and Company, "BD™ EMB Agar (Eosin Methylene Blue Agar), Modified Intended Use", Becton, Dickinson and Company, Available Online at: https://www.bd.com/resource.aspx?idx=8973, 2013, pp. 1-3.

(Continued)

*Primary Examiner* — Elizabeth A Robinson
*Assistant Examiner* — Austin Q Le
(74) *Attorney, Agent, or Firm* — Kilpatrick Townsend & Stockton LLP

(57) ABSTRACT

The present disclosure relates to a blood staining patch, a method and device for a blood test using the same, and more particularly, to a patch configured to contain a staining reagent for staining blood and a method and device for economically testing blood using the same. A blood testing method according to an aspect of the present disclosure, which is a blood testing method in which a patch, which (Continued)

includes a mesh structure forming micro-cavities and is configured to contain a staining reagent for staining targets present in blood in the micro-cavities, is used to perform a blood test through staining of the staining target, includes placing blood in a reaction region, and providing the staining reagent to the reaction region using the patch configured to contain the staining reagent.

12 Claims, 65 Drawing Sheets

Related U.S. Application Data

(60) Provisional application No. 62/298,959, filed on Feb. 23, 2016.

(30) Foreign Application Priority Data

| Jun. 4, 2016 | (KR) | ........................ | 10-2016-0069938 |
| Jul. 27, 2016 | (KR) | ........................ | 10-2016-0095739 |
| Sep. 13, 2016 | (KR) | ........................ | 10-2016-0118462 |
| Nov. 1, 2016 | (KR) | ........................ | 10-2016-0144551 |
| Feb. 23, 2017 | (KR) | ........................ | 10-2017-0024391 |

(51) Int. Cl.

| C07K 16/30 | (2006.01) |
| C12Q 1/6844 | (2018.01) |
| C12Q 1/6848 | (2018.01) |
| C12Q 1/686 | (2018.01) |
| C12Q 1/70 | (2006.01) |
| G01N 1/30 | (2006.01) |
| G01N 15/06 | (2024.01) |
| G01N 15/14 | (2024.01) |
| G01N 21/77 | (2006.01) |
| G01N 33/483 | (2006.01) |
| G01N 33/49 | (2006.01) |
| G01N 33/50 | (2006.01) |
| G01N 33/52 | (2006.01) |
| G01N 33/53 | (2006.01) |
| G01N 33/533 | (2006.01) |
| G01N 33/558 | (2006.01) |
| G01N 33/574 | (2006.01) |
| G01N 33/60 | (2006.01) |
| G06T 7/00 | (2017.01) |
| B01L 7/00 | (2006.01) |
| G01N 15/01 | (2024.01) |
| G01N 15/075 | (2024.01) |

(52) U.S. Cl.
CPC ......... *C12Q 1/6844* (2013.01); *C12Q 1/6848* (2013.01); *C12Q 1/686* (2013.01); *C12Q 1/701* (2013.01); *G01N 1/30* (2013.01); *G01N 1/31* (2013.01); *G01N 15/06* (2013.01); *G01N 15/14* (2013.01); *G01N 21/77* (2013.01); *G01N 33/4833* (2013.01); *G01N 33/49* (2013.01); *G01N 33/5082* (2013.01); *G01N 33/52* (2013.01); *G01N 33/5304* (2013.01); *G01N 33/533* (2013.01); *G01N 33/574* (2013.01); *G01N 33/60* (2013.01); *G06T 7/0012* (2013.01); *G06T 7/0014* (2013.01); *B01L 3/505* (2013.01); *B01L 7/52* (2013.01); *G01N 2001/302* (2013.01); *G01N 15/01* (2024.01); *G01N 15/075* (2024.01); *G01N 2021/7723* (2013.01); *G01N 2021/7786* (2013.01)

(58) Field of Classification Search
CPC ........ G01N 15/14; G01N 21/77; G01N 33/49; G01N 33/52; G01N 33/5304; G01N 33/533; G01N 33/558; G01N 33/92; G01N 2001/302; G01N 2015/0065; B01F 33/3039; C07K 16/3061; C12N 2503/12; C12Q 1/025; C12Q 1/6844; C12Q 1/6848; C12Q 1/686; C12Q 1/701
See application file for complete search history.

(56) References Cited

U.S. PATENT DOCUMENTS

| 4,250,257 | A | 2/1981 | Lee et al. |
| 4,839,297 | A | 6/1989 | Freitag et al. |
| 4,938,593 | A | 7/1990 | Morris et al. |
| 5,143,714 | A | 9/1992 | Cosgrove et al. |
| 5,385,846 | A | 1/1995 | Kuhn et al. |
| 5,552,270 | A | 9/1996 | Khrapko et al. |
| 5,552,279 | A | 9/1996 | Weisburg et al. |
| 5,776,684 | A | 7/1998 | Chirikjian et al. |
| 5,779,982 | A | 7/1998 | Aota et al. |
| 5,928,879 | A | 7/1999 | Dumler et al. |
| 6,063,029 | A | 5/2000 | Saita et al. |
| 6,174,683 | B1 | 1/2001 | Hahn et al. |
| 7,183,356 | B2 | 2/2007 | Ishida |
| 7,261,800 | B1 | 8/2007 | Nakazato |
| 7,522,757 | B2 | 4/2009 | Tsipouras et al. |
| 7,767,414 | B1 | 8/2010 | Smith et al. |
| 8,293,487 | B1 | 10/2012 | Zhang |
| 8,305,579 | B2 | 11/2012 | Treynor et al. |
| 8,409,849 | B2 | 4/2013 | Yamasaki |
| 8,597,574 | B2 | 12/2013 | Gumbrecht et al. |
| 8,628,787 | B2 | 1/2014 | Soldani et al. |
| 8,809,027 | B1 | 8/2014 | Lynch et al. |
| 8,936,912 | B2 | 1/2015 | Mitra et al. |
| 10,234,447 | B2 | 3/2019 | Manaresi et al. |
| 10,254,286 | B2 | 4/2019 | Pirie-Shepherd et al. |
| 10,345,204 | B2 | 7/2019 | Lee et al. |
| 10,371,610 | B2 | 8/2019 | Lee et al. |
| 11,041,842 | B2 | 6/2021 | Lee et al. |
| 2002/0055126 | A1 | 5/2002 | Schaffler et al. |
| 2003/0083294 | A1 | 5/2003 | Sullenger et al. |
| 2003/0086927 | A1 | 5/2003 | Gordon et al. |
| 2003/0124619 | A1 | 7/2003 | Weigl et al. |
| 2003/0211507 | A1 | 11/2003 | Hatch et al. |
| 2004/0038306 | A1 | 2/2004 | Agnew et al. |
| 2004/0126826 | A1 | 7/2004 | Yusuf et al. |
| 2004/0175710 | A1 | 9/2004 | Haushalter |
| 2005/0139511 | A1 | 6/2005 | Burns et al. |
| 2005/0175987 | A1 | 8/2005 | Jansen et al. |
| 2005/0175997 | A1 | 8/2005 | Ono et al. |
| 2005/0202567 | A1 | 9/2005 | Zanzucchi et al. |
| 2005/0244976 | A1 | 11/2005 | Gee et al. |
| 2006/0088847 | A1 | 4/2006 | Gu |
| 2006/0111331 | A1 | 5/2006 | Eishingdrelo et al. |
| 2006/0115905 | A1 | 6/2006 | Hatch et al. |
| 2006/0121474 | A1 | 6/2006 | Kim et al. |
| 2006/0172278 | A1 | 8/2006 | Bonner et al. |
| 2007/0051630 | A1 | 3/2007 | Larsson et al. |
| 2007/0087362 | A1 | 4/2007 | Church et al. |
| 2007/0117177 | A1 | 5/2007 | Luo et al. |
| 2007/0128073 | A1 | 6/2007 | Tappen |
| 2007/0224701 | A1 | 9/2007 | Rosenstein |
| 2008/0090267 | A1 | 4/2008 | Komatsu et al. |
| 2008/0138842 | A1 | 6/2008 | Boehringer et al. |
| 2008/0166745 | A1 | 7/2008 | Khan et al. |
| 2008/0182287 | A1 | 7/2008 | Smith et al. |
| 2008/0241890 | A1 | 10/2008 | Gumbrecht et al. |
| 2008/0286208 | A1* | 11/2008 | Korb .................. A61K 49/006 424/9.1 |
| 2009/0098165 | A1 | 4/2009 | Arulanandam et al. |
| 2009/0220968 | A1 | 9/2009 | Issadore et al. |
| 2009/0226911 | A1 | 9/2009 | Mauk et al. |
| 2010/0047790 | A1 | 2/2010 | Southern et al. |
| 2010/0168390 | A1 | 7/2010 | Brix et al. |

(56) References Cited

U.S. PATENT DOCUMENTS

| | | | |
|---|---|---|---|
| 2011/0041978 A1 | 2/2011 | Wallace | |
| 2011/0070606 A1 | 3/2011 | Winkelman et al. | |
| 2011/0257666 A1 | 10/2011 | Ladet et al. | |
| 2012/0040397 A1 | 2/2012 | Luo et al. | |
| 2012/0064041 A1 | 3/2012 | Alexanian | |
| 2012/0169863 A1* | 7/2012 | Bachelet | G01N 21/23 |
| | | | 348/79 |
| 2012/0171290 A1 | 7/2012 | Coursaget et al. | |
| 2012/0196320 A1 | 8/2012 | Seibel et al. | |
| 2013/0130930 A1* | 5/2013 | Parikh | G01N 33/689 |
| | | | 435/6.12 |
| 2013/0213811 A1 | 8/2013 | Kennedy et al. | |
| 2013/0288273 A1 | 10/2013 | Takagi et al. | |
| 2013/0296761 A1 | 11/2013 | Goto et al. | |
| 2013/0337566 A1 | 12/2013 | Schmidt et al. | |
| 2013/0338016 A1 | 12/2013 | McDonough et al. | |
| 2014/0004527 A1 | 1/2014 | Oka et al. | |
| 2014/0038230 A1 | 2/2014 | Beck et al. | |
| 2014/0073063 A1 | 3/2014 | Lieber et al. | |
| 2014/0193892 A1* | 7/2014 | Mohan | G01N 15/1434 |
| | | | 435/287.2 |
| 2014/0242601 A1 | 8/2014 | Belbruno | |
| 2014/0242607 A1 | 8/2014 | Sogabe et al. | |
| 2014/0273088 A1 | 9/2014 | Winther | |
| 2014/0349382 A1 | 11/2014 | Thomson et al. | |
| 2015/0080252 A1 | 3/2015 | Godwin et al. | |
| 2015/0139511 A1 | 5/2015 | Yoon et al. | |
| 2015/0167073 A1 | 6/2015 | Romanov et al. | |
| 2016/0265028 A1 | 9/2016 | Kim et al. | |
| 2017/0003309 A1 | 1/2017 | Mitra | |
| 2019/0025281 A1 | 1/2019 | Lee et al. | |
| 2019/0048395 A1 | 2/2019 | Lee et al. | |
| 2019/0049349 A1 | 2/2019 | Lee et al. | |
| 2019/0049426 A1 | 2/2019 | Lee et al. | |
| 2019/0056298 A1 | 2/2019 | Lee et al. | |
| 2019/0064140 A1 | 2/2019 | Lee et al. | |
| 2019/0316995 A1 | 10/2019 | Lee et al. | |
| 2020/0011772 A1 | 1/2020 | Lee et al. | |
| 2020/0240882 A1 | 7/2020 | Lee et al. | |
| 2020/0249134 A1 | 8/2020 | Lee et al. | |
| 2021/0340607 A1 | 11/2021 | Lee et al. | |

FOREIGN PATENT DOCUMENTS

| | | |
|---|---|---|
| CN | 1363006 | 8/2002 |
| CN | 1409110 | 4/2003 |
| CN | 1561202 | 1/2005 |
| CN | 1747703 | 3/2006 |
| CN | 1971276 | 5/2007 |
| CN | 101004377 | 7/2007 |
| CN | 101225430 | 7/2008 |
| CN | 101464237 | 6/2009 |
| CN | 101598731 | 12/2009 |
| CN | 101610847 | 12/2009 |
| CN | 102245305 | 11/2011 |
| CN | 102245755 | 11/2011 |
| CN | 102272595 | 12/2011 |
| CN | 102665917 | 9/2012 |
| CN | 103038639 | 4/2013 |
| CN | 103261872 | 8/2013 |
| CN | 103328651 | 9/2013 |
| CN | 103800040 | 5/2014 |
| CN | 103808551 | 5/2014 |
| CN | 104271191 | 1/2015 |
| CN | 104349769 | 2/2015 |
| CN | 104651473 | 5/2015 |
| CN | 105122034 | 12/2015 |
| CN | 105136795 | 12/2015 |
| CN | 105259095 | 1/2016 |
| EP | 2072993 | 6/2009 |
| EP | 2206462 | 7/2010 |
| EP | 2940474 | 11/2015 |
| JP | 5289375 | 7/1977 |
| JP | 63281050 | 11/1988 |
| JP | H 08-271390 | 10/1996 |
| JP | 2003344394 | 12/2003 |
| JP | 2004077387 | 3/2004 |
| JP | 2004298157 | 10/2004 |
| JP | 2004298158 | 10/2004 |
| JP | 2005003529 | 1/2005 |
| JP | 2008518662 | 6/2008 |
| JP | 2008164520 | 7/2008 |
| JP | 2009518651 | 5/2009 |
| JP | 2012515931 | 7/2012 |
| JP | 5198399 | 5/2013 |
| JP | 2013515235 | 5/2013 |
| JP | 2013515955 | 5/2013 |
| KR | 100601831 | 7/2006 |
| KR | 20060112258 | 10/2006 |
| KR | 20110084636 | 7/2011 |
| KR | 20110136782 | 12/2011 |
| KR | 20130138153 | 12/2013 |
| KR | 20140082757 | 7/2014 |
| KR | 20140100580 | 8/2014 |
| KR | 20140103350 | 8/2014 |
| KR | 101453796 | 10/2014 |
| KR | 20150048964 | 5/2015 |
| KR | 101540845 | 7/2015 |
| WO | 200077293 | 12/2000 |
| WO | 02072081 | 9/2002 |
| WO | 02072262 | 9/2002 |
| WO | 2004024955 | 3/2004 |
| WO | 2004071469 | 8/2004 |
| WO | 2006050032 | 5/2006 |
| WO | 2006053770 | 5/2006 |
| WO | 2006108087 | 10/2006 |
| WO | 2007067847 | 6/2007 |
| WO | 2007138568 | 12/2007 |
| WO | 2008075086 | 6/2008 |
| WO | 2010039627 | 4/2010 |
| WO | 2010041088 | 4/2010 |
| WO | 2010052543 | 5/2010 |
| WO | 2010082820 | 7/2010 |
| WO | 2011066449 | 6/2011 |
| WO | 2011076705 | 6/2011 |
| WO | 2011080539 | 7/2011 |
| WO | 2011143075 | 11/2011 |
| WO | 2012003579 | 1/2012 |
| WO | 2012030313 | 3/2012 |
| WO | 2012048154 | 4/2012 |
| WO | 2012072980 | 6/2012 |
| WO | 2012137506 | 10/2012 |
| WO | 2013086015 | 6/2013 |
| WO | 2013095896 | 6/2013 |
| WO | 2013103712 | 7/2013 |
| WO | 2013111054 | 8/2013 |
| WO | 2013169924 | 11/2013 |
| WO | 2014041093 | 3/2014 |
| WO | 2014146062 | 9/2014 |
| WO | 2015137595 | 9/2015 |
| WO | 2017048871 | 3/2017 |

OTHER PUBLICATIONS

Cardinal Health, "Histology vol. II: Laboratory Products for Your Histology Needs", Cardinal Health, Available Online at: https://www.henryschein.com/assets/medical/2883001.pdf, 2013, 95 pages.

Definition of "Mesh", Available Online at: https://www.dictionary.com/browse/mesh?s=t, Accessed from Internet on Sep. 7, 2022, 5 pages.

U.S. Appl. No. 16/079,271 , "Final Office Action", Nov. 28, 2022, 11 pages.

Beck et al., "On-Chip Sample Preparation by Controlled Release of Antibodies for Simple CD4 Counting", Lab on a Chip, vol. 12, No. 1, Nov. 3, 2011, pp. 167-173.

Deiss et al., "Antimicrobial Susceptibility Assays in Paper-Based Portable Culture Devices", Lab on a Chip, vol. 14, No. 1, Jan. 2014, pp. 167-171.

EP21207600.4 , "Extended European Search Report", Mar. 11, 2022, 11 pages.

(56)          References Cited

OTHER PUBLICATIONS

Geckil et al., "Engineering Hydrogels as Extracellular Matrix Mimics", Nanomedicine (Lond), vol. 5, No. 2, Apr. 2010, pp. 469-484.

Horibata et al., "Utilization of the Soft Agar Colony Formation Assay to Identify Inhibitors of Tumorigenicity in Breast Cancer Cells", Journal of Visualized Experiments, vol. 99, May 20, 2015, pp. 1-7.

Hudzicki , "Kirby-Bauer Disk Diffusion Susceptibility Test Protocol", Available Online at: https://asm.org/getattachment/2594ce26-bd44-47f6-8287-0657aa9185ad/Kirby-Bauer-Disk-Diffusion-Susceptibility-Test-Protocol-pdf.pdf, Dec. 8, 2009, 23 pages.

Kim et al., "A Disposable, Self-Contained PCR Chip", Lab Chip, vol. 9, No. 4, Feb. 21, 2009, pp. 606-612.

Liu et al., "Aptamer-Nanoparticle Strip Biosensor for Sensitive Detection of Cancer Cells", Analytical Chemistry, vol. 81, No. 24, Dec. 15, 2009, 13 pages.

Man et al., "Currently Used Markers for CTC Isolation—Advantages, Limitations and Impact on Cancer Prognosis", Journal of Clinical & Experimental Pathology, vol. 1, No. 1, 2011, 7 pages.

Massart et al., "Striatal GPR88 Expression is Confined to the Whole Projection Neuron Population and is Regulated by Dopaminergic and Glutamatergic Afferents", European Journal of Neuroscience, vol. 30, No. 3, Aug. 2009, pp. 397-414.

Matsuo et al., "A Simple Method for Classification of Cell Death by Use of Thin Layer Collagen Gel for the Detection of Apoptosis and/or Necrosis After Cancer Chemotherapy", Japanese Journal of Cancer Research, vol. 92, No. 7, Jul. 2001, pp. 813-819.

Notodihardjo et al., "Gelatin Hydrogel Impregnated with Platelet-Rich Plasma Releasate Promotes Angiogenesis and Wound Healing in Murine Model", Journal of Artificial Organs, vol. 18, No. 1, Mar. 2015, pp. 64-71.

Oss-Ronen et al., "Polymer-Conjugated Albumin and Fibrinogen Composite Hydrogels as Cell Scaffolds Designed for Affinity-Based Drug Delivery", Acta Biomaterialia, vol. 7, No. 1, Jan. 2011, pp. 163-170.

PCT/KR2017/002026 , "International Search Report and Written Opinion", May 29, 2017, 15 pages.

PCT/KR2017/002027 , "International Search Report and Written Opinion", May 29, 2017, 16 pages.

PCT/KR2017/002028 , "International Search Report and Written Opinion", Jul. 6, 2017, 17 pages.

PCT/KR2017/002029 , "International Search Report and Written Opinion", May 29, 2017, 17 pages.

PCT/KR2017/002030 , "International Search Report and Written Opinion", May 29, 2017, 18 pages.

PCT/KR2017/002031 , "International Search Report and Written Opinion", May 29, 2017, 23 pages.

PCT/KR2017/002032 , "International Search Report and Written Opinion", May 29, 2017, 21 pages.

Punyani et al., "Sustained Release of Iodine from a Polymeric Hydrogel Device for Water Disinfection", Journal of Applied Polymer Science, vol. 103, No. 5, Dec. 19, 2006, pp. 3334-3340.

Rand , "Crystal Violet can be Used to Visualize DNA Bands During Gel Electrophoresis and to Improve Cloning Efficiency", Technical Tips Online, vol. 1, No. 1, Jan. 1996, pp. 23-24.

Romano et al., "Controlled Antiseptic/Eosin Release from Chitosan-Based Hydrogel Modified Fibrous Substrates", Carbohydrate Polymers, vol. 131, Oct. 20, 2015, 27 pages.

Sun et al., "Fluorescence in Situ Hybridization: Method of Choice for a Definitive Diagnosis of Mantle Cell Lymphoma", American Journal of Hematology, vol. 74, No. 1, 2003, pp. 78-84.

Wakayama et al., "Design of a Single-Step Immunoassay Principle Based on the Combination of an Enzyme-Labeled Antibody Release Coating and a Hydrogel Copolymerized with a Fluorescent Enzyme Substrate in a Microfluidic Capillary Device", Lab on a Chip, vol. 13, No. 22, Nov. 21, 2013, pp. 4304-4307.

Wu et al., "Disposable Reagentless Electrochemical Immunosensor Array Based on a Biopolymer/Sol-Gel Membrane for Simultaneous Measurement of Several Tumor Markers", Clinical Chemistry, vol. 54, No. 9, Sep. 2008, pp. 1481-1488.

Zhu et al., "Microbiology Experiment and Learning Guide—Experiment 6 In Vitro Antibacterial Test of Drug", Fourth Force Medical University Press, 2015, 11 pages.

Zustiak et al., "Solute Diffusion and Interactions in Cross-Linked Poly(Ethylene Glycol) Hydrogels Studied by Fluorescence Correlation Spectroscopy", Soft Matter, vol. 6, No. 15, Aug. 7, 2010, 24 pages.

Zheng S. et al., 3D microfilter device for viable circulating tumor cell (CTC) enrichment from blood, Biomedical microdevices, kluwer academic publishers, BO, vol. 13, No. 1, Oct. 27, 2010 pp. 203-213.

Extended European Search Report, EP Application No. 23206369.3 mailed Feb. 21, 2024, 9 pages.

\* cited by examiner

PA

MH

SS

PA

SB3

FIG. 7
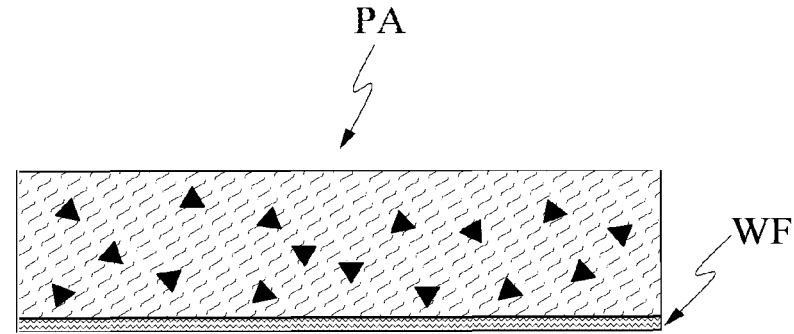
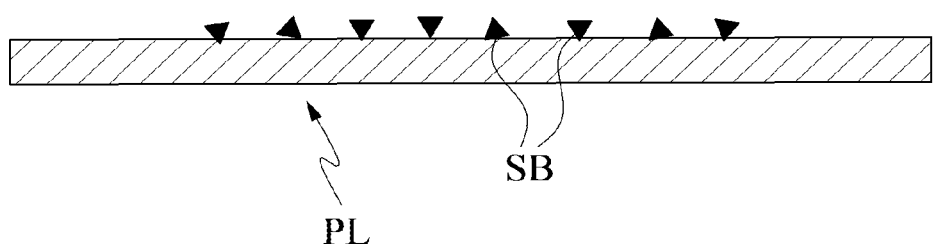

FIG. 8
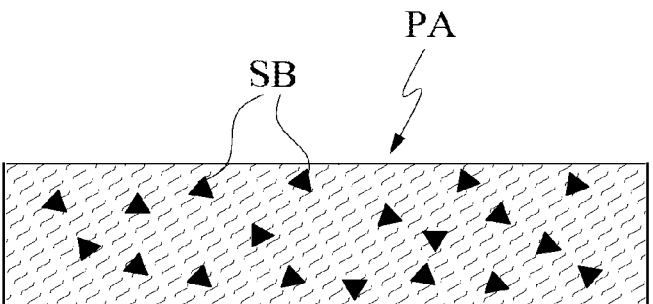
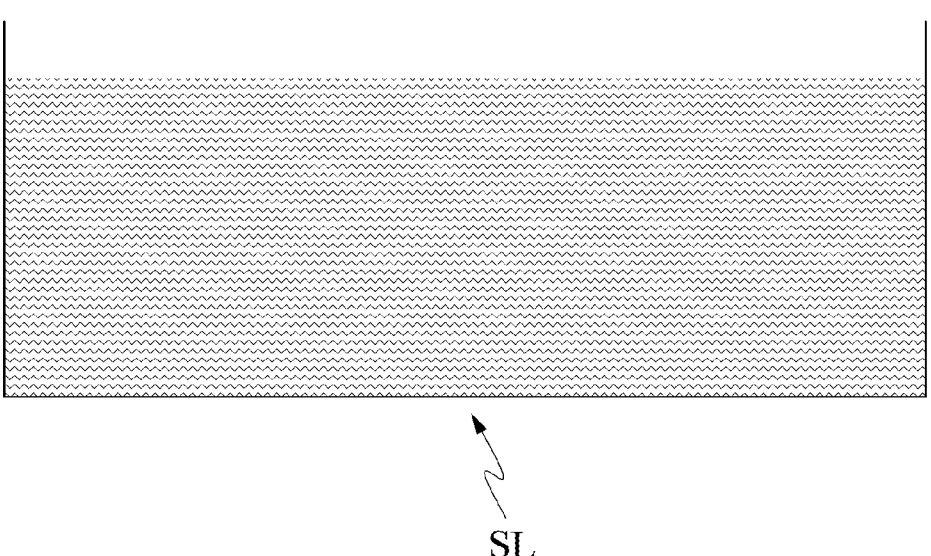

FIG. 14
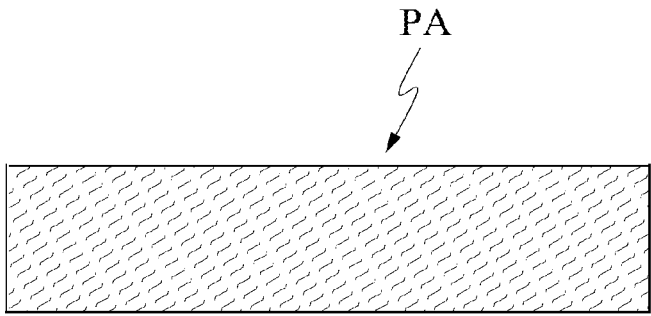
PA
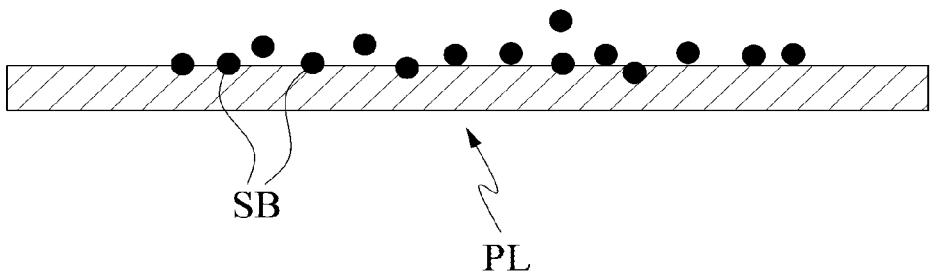
SB
PL

FIG. 16
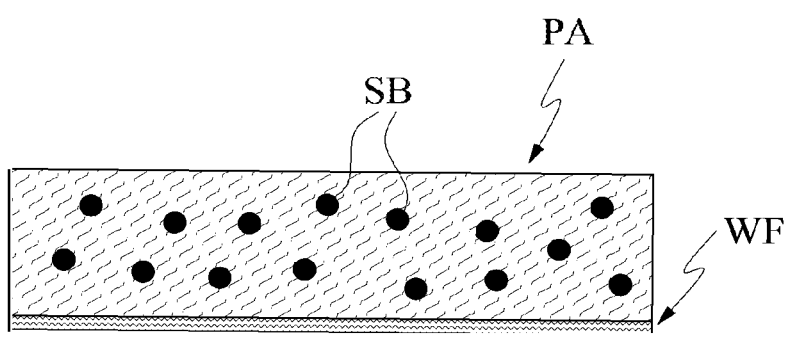
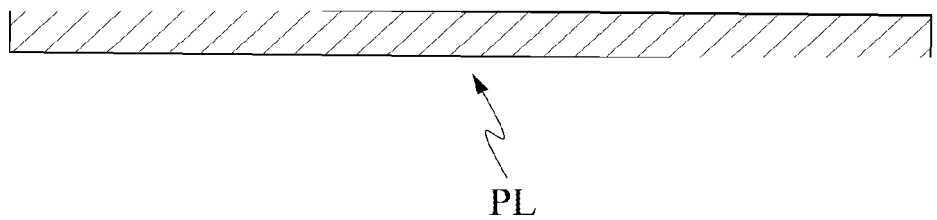

FIG. 17
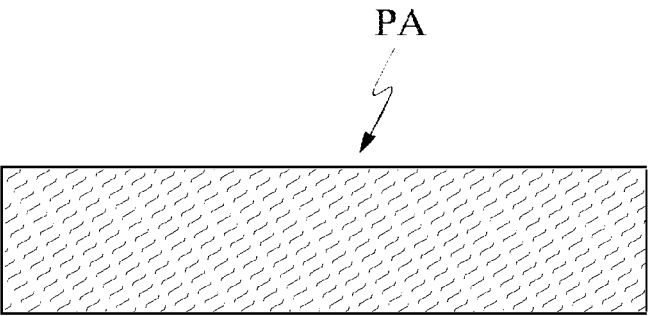
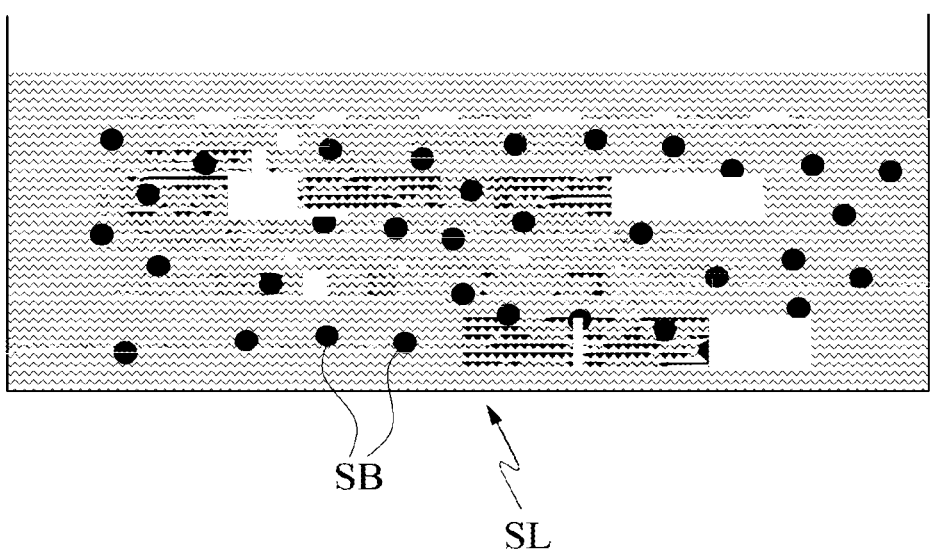

FIG. 23
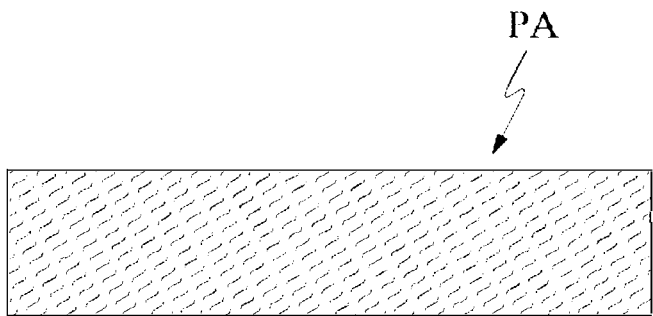
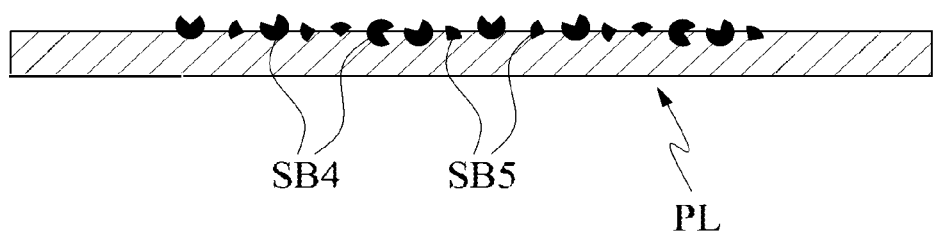

FIG. 25
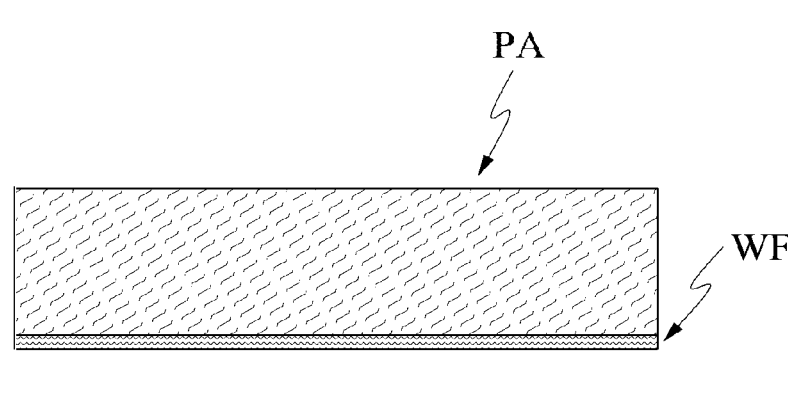
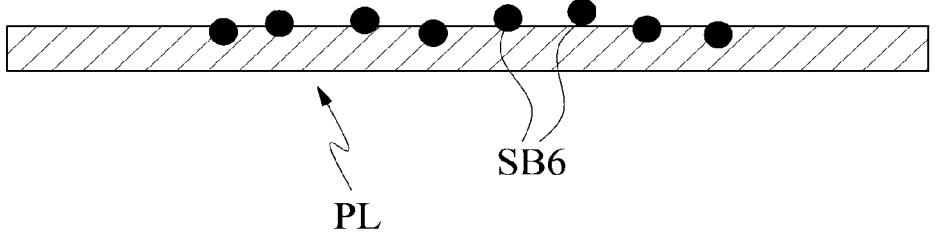

FIG. 26
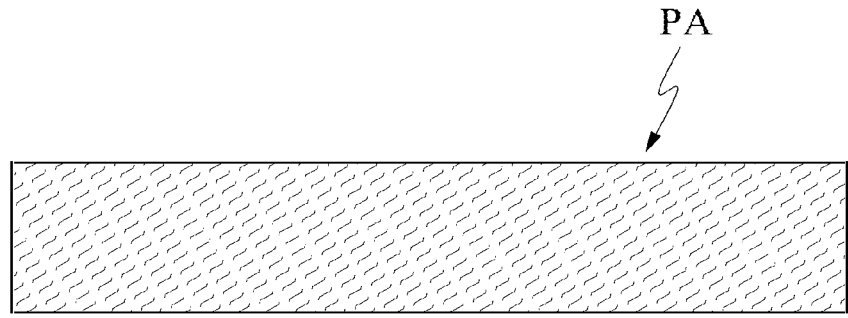
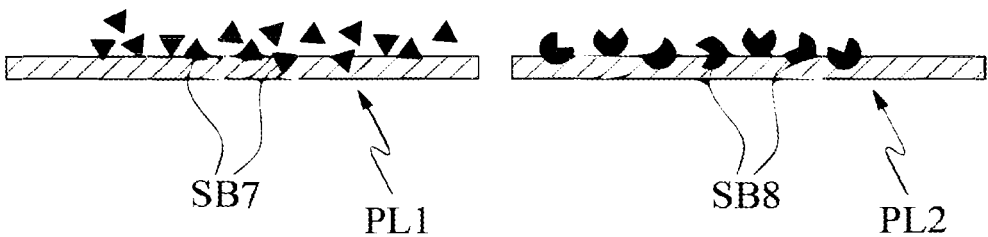

TA

○  1st staining
   reagent

△  1st target which is
   not stained

▲  1st target which is stained
   by 1st staining reagent

□  2nd target which is
   not stained

▨  2nd target which is
   stained

FIG. 60

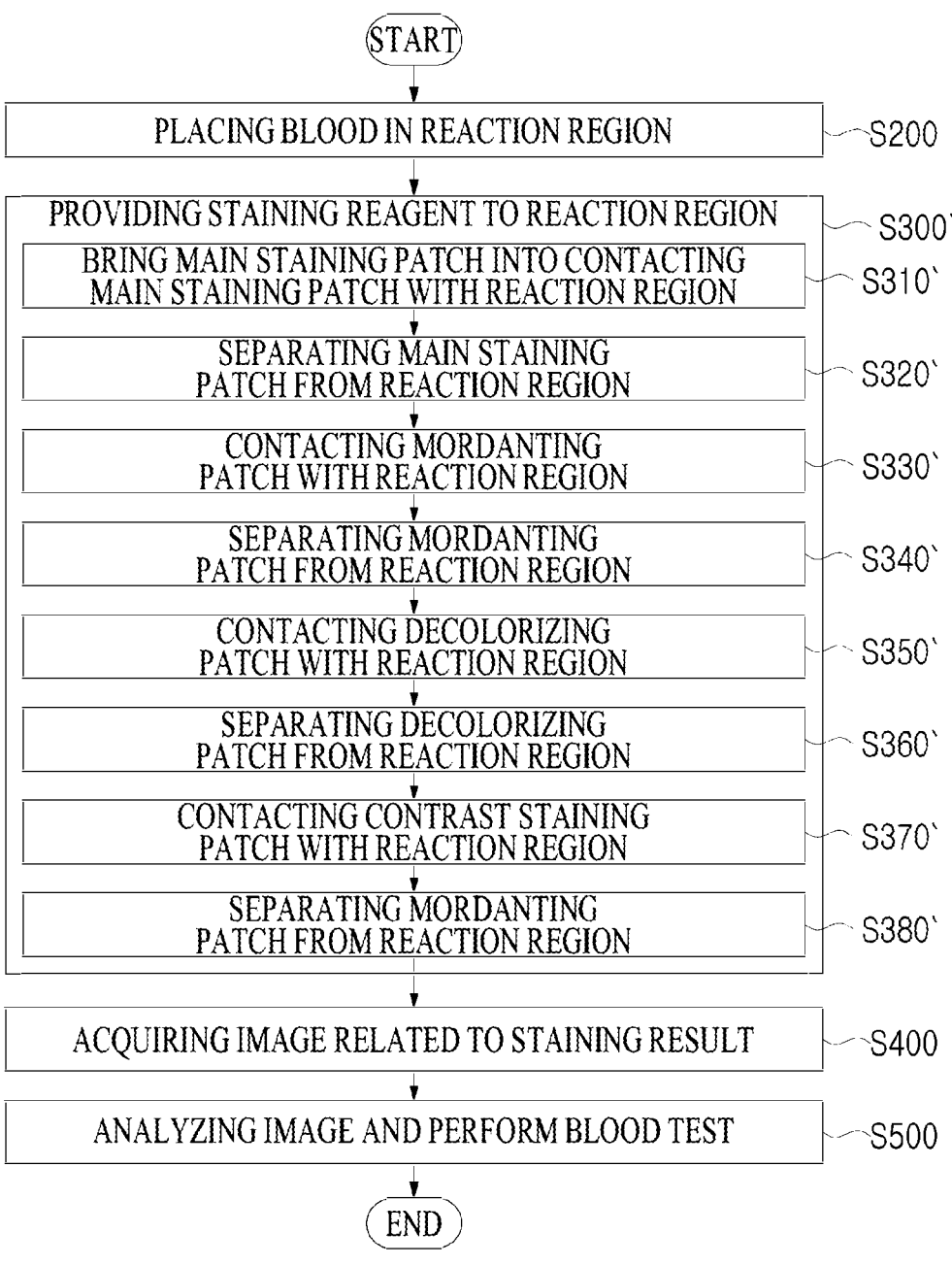

START

PLACING BLOOD IN REACTION REGION — S200

PROVIDING STAINING REAGENT TO REACTION REGION — S300`

BRING MAIN STAINING PATCH INTO CONTACTING MAIN STAINING PATCH WITH REACTION REGION — S310`

SEPARATING MAIN STAINING PATCH FROM REACTION REGION — S320`

CONTACTING MORDANTING PATCH WITH REACTION REGION — S330`

SEPARATING MORDANTING PATCH FROM REACTION REGION — S340`

CONTACTING DECOLORIZING PATCH WITH REACTION REGION — S350`

SEPARATING DECOLORIZING PATCH FROM REACTION REGION — S360`

CONTACTING CONTRAST STAINING PATCH WITH REACTION REGION — S370`

SEPARATING MORDANTING PATCH FROM REACTION REGION — S380`

ACQUIRING IMAGE RELATED TO STAINING RESULT — S400

ANALYZING IMAGE AND PERFORM BLOOD TEST — S500

END

○     main staining reagent

△     positive target
      not stained

▲     positive target which is stained
      by main staining reagent

□     negative target which is
      not stained

■     negative target which is stained
      by main staining reagent

●    sub staining reagent

△    positive target which is not stained

▲    positive target which is stained by main staining reagent

☐    negative target which is not stained

▨    negative targe which is stained by sub staining reagent

BLOOD STAINING PATCH, METHOD AND DEVICE FOR BLOOD TEST USING THE SAME

CROSS REFERENCE TO RELATED APPLICATIONS

This application is a divisional of U.S. patent application Ser. No. 16/079,271, filed on Aug. 23, 2018, the disclosure of which is incorporated by reference in its entirety for all purposes.

TECHNICAL FIELD

The present disclosure relates to a blood staining patch, a method and device for a blood test using the same, and more particularly, to a patch configured to contain a staining reagent for staining blood and an economical method and device for testing blood using the same.

BACKGROUND ART

Due to a rapidly aging society and increasing need for quality of life, the diagnostics market which aims at early diagnosis and early treatment is growing every year in the world, including South Korea, and quick and easy diagnosis is becoming an important issue. In particular, forms of diagnosis are being transitioned into forms in which diagnosis can be performed without using large diagnostic equipment, such as in-vitro diagnosis (IVD) or point-of-care testing (POCT) which is immediately performed next to a patient. Blood testing, which is one specific diagnostic field for performing IVD, is one diagnostic method that accounts for a large portion in the IVD field and is widely used.

Blood testing belongs in a field of hematology. Blood testing is used to diagnose a patient's health condition, illness, or disease by examining for the presence of bacteria in blood or blood cells, such as red blood cells, white blood cells, and platelets.

Conventionally, blood tests may be broadly classified into direct testing methods in which a tester observes blood directly through visual inspection using a microscope and indirect testing methods, of which typical examples are flow cytometry and an electrical impedance measurement method.

The direct testing methods are performed mostly by staining blood which is smeared on a slide glass using a staining solution and then observing staining results through a microscope. In the conventional direct testing methods, a process of smearing blood, a process of staining the smeared blood, and a process of observing the stained blood through visual inspection using a microscope depends entirely on work manually performed by a tester. Therefore, due to requiring not only a skilled tester but also a large amount of time for testing, the conventional direct testing methods are not able to be performed outside laboratory units.

On the other hand, in indirect testing methods, characteristics of blood are examined through light dispersed as a result of irradiating a laser on blood while blood passing through a micro-fluidic channel, or a change in impedance as a result of applying a current to a blood sample. The indirect testing methods are relatively automated and used in large hospitals due to the above-mentioned characteristics. However, since blood is not directly observed, and it is difficult to perform a precise blood test with the indirect testing methods due to the indirect technical limitations.

SUMMARY

An aspect of the present disclosure is to provide a patch capable of storing a sub stance.

An aspect of the present disclosure is to provide a patch capable of providing a reaction space for a substance.

An aspect of the present disclosure is to provide a patch capable of providing a sub stance.

An aspect of the present disclosure is to provide a patch capable of absorbing a sub stance.

An aspect of the present disclosure is to provide a patch capable of providing an environment.

An aspect of the present disclosure is to provide a patch capable of storing a staining reagent for staining blood.

An aspect of the present disclosure is to provide a blood testing method using a patch.

Aspects of the present disclosure are not limited to those mentioned above, and unmentioned aspects will be clearly understood by those of ordinary skill in the art to which the present disclosure pertains from the present specification and the accompanying drawings.

According to an aspect of the present disclosure, there is provided a staining patch including a staining reagent configured to stain staining targets present in blood, and a mesh structural body provided in a mesh structure forming micro-cavities in which the staining reagent is contained that is configured to come into contact with a reaction region in which the blood is placed and deliver a portion of the contained staining reagent to the reaction region.

According to another aspect of the present disclosure, there is provided a blood testing method in which a patch, which includes a mesh structural body forming micro-cavities and is configured to contain a staining reagent for staining staining targets present in blood in the micro-cavities, is used to perform a blood test through staining of the staining target, the blood testing method including placing blood in a reaction region and providing the staining reagent to the reaction region using the patch configured to contain the staining reagent.

According to yet another aspect of the present disclosure, there is provided a blood test device using a patch, which includes a mesh structural body forming micro-cavities and is configured to contain a staining reagent for staining staining targets present in blood in the micro-cavities, to perform a blood test through staining of the staining target, the blood test device including a plate supporter configured to support a plate on which a reaction region is placed and blood is placed in the reaction region, a patch controller configured to use the patch, which is configured to contain the staining reagent, and control a relative position of the patch relative to the reaction region so that the staining reagent is provided to the reaction region, and a reaction detector configured to detect a result of staining of the staining target present in the blood to examine the blood.

Solutions of the present disclosure are not limited to those mentioned above, and unmentioned solutions should be clearly understood by those of ordinary skill in the art to which the present disclosure pertains from the present specification and the accompanying drawings.

According to the present disclosure, containing, providing, and absorption of a substance can be easily performed.

According to the present disclosure, a reaction region for a substance can be provided or a predetermined environment can be provided to a target region.

According to the present disclosure, a blood test can be more conveniently performed, and a test result can be promptly obtained.

According to the present disclosure, a diagnosis result with sufficient validity can be obtained using a small amount of blood.

According to the present disclosure, providing and absorption of a substance can be properly adjusted using a path, and an amount of a staining reagent consumed for diagnosis can be significantly reduced.

According to the present disclosure, diagnosis can be performed by detecting a plurality of targets simultaneously, and patient-specific diagnosis can be performed as a result.

Advantageous effects of the present disclosure are not limited to those mentioned above, and unmentioned advantageous effects should be clearly understood by those of ordinary skill in the art to which the present disclosure pertains from the present specification and the accompanying drawings.

DESCRIPTION OF DRAWINGS

FIG. 7 illustrates providing of a substance as an example of a function of a patch according to the present application.

FIG. 8 illustrates providing of a substance as an example of a function of a patch according to the present application.

FIG. 14 illustrates absorbing of a substance as an example of a function of a patch according to the present application.

FIG. 16 illustrates absorbing of a substance as an example of a function of a patch according to the present application.

FIG. 17 illustrates absorbing of a substance as an example of a function of a patch according to the present application.

FIG. 23 illustrates providing of an environment as an example of a function of a patch according to the present application.

FIG. 25 illustrates providing of an environment as an example of a function of a patch according to the present application.

FIG. 26 illustrates performance of absorbing and providing of a substance as an embodiment of a patch according to the present application.

FIG. 60 is a flowchart for describing a blood testing method using a Gram stain as still another example of a blood testing method according to the present application.

DETAILED DESCRIPTION

Figure 1:
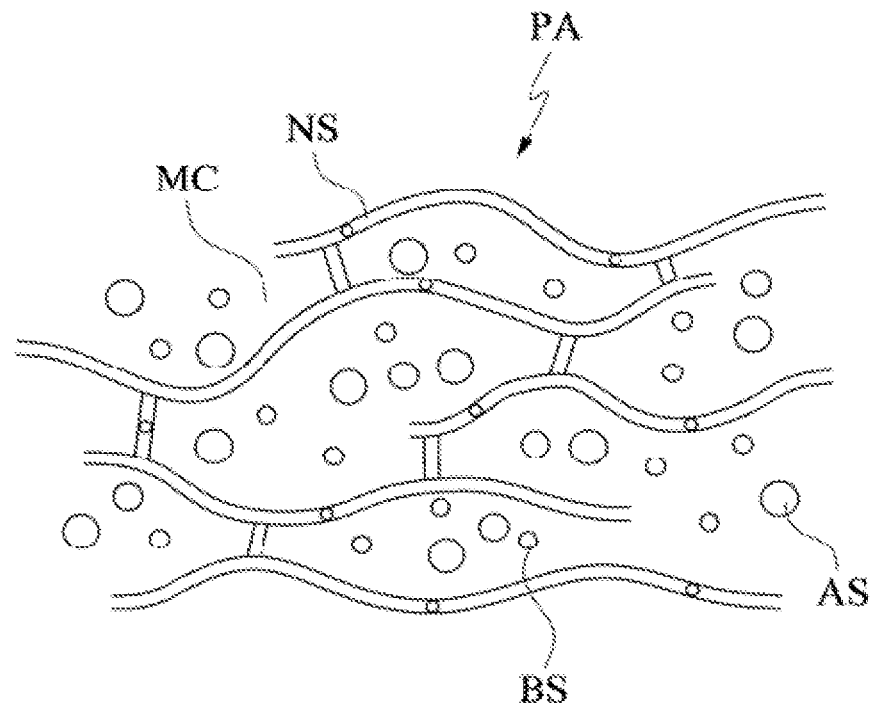
FIG. 1 illustrates an example of a patch in detail according to the present application.

Since embodiments described herein are for clearly describing the spirit of the present disclosure to those of ordinary skill in the art to which the present disclosure pertains, the present disclosure is not limited to the embodiments described herein, and the scope of the present disclosure should be construed as including revised examples or modified examples not departing from the spirit of the present disclosure.

General terms currently being used as widely as possible have been selected as terms used herein in consideration of functions in the present disclosure, but the terms may be changed according to intentions and practices of those of ordinary skill in the art to which the present disclosure pertains or the advent of new technologies, etc. However, instead, when a particular term is defined as a certain meaning and used, the meaning of the term will be separately described. Consequently, the terms used herein should be construed on the basis of substantial meanings of the terms and content throughout the present specification instead of simply on the basis of names of the terms.

The accompanying drawings herein are for easily describing the present disclosure. Since shapes illustrated in the drawings may have been exaggeratedly depicted as much as necessary to assist in understating the present disclosure, the present disclosure is not limited by the drawings.

When detailed description of a known configuration or function related to the present disclosure is deemed to obscure the gist of the present disclosure in the present specification, the detailed description related thereto will be omitted as necessary.

According to an aspect of the present disclosure, there is provided a staining patch including a staining reagent configured to stain staining targets present in blood, and a mesh structural body provided in a mesh structure forming microcavities in which the staining reagent is contained that is configured to come into contact with a reaction region in which the blood is placed and provide a portion of the contained staining reagent to the reaction region.

The staining reagent configured to stain the staining target may include at least one of an acidic staining reagent, a basic staining reagent, and a neutral staining reagent.

The staining reagent may include a fluorescent staining reagent configured to allow the staining target develop fluorescent color.

The staining target may include at least one of blood cells, bacteria, and parasites present in the blood, and the staining reagent may stain at least one of a cytoplasm, a nucleus, and a granule of the staining target.

There may be a plurality of staining targets, and the staining reagent may include a first staining reagent configured to stain a first staining target in the staining targets and a second staining reagent configured to stain a second staining target in the staining targets.

According to another aspect of the present disclosure, there is provided a blood testing method, in which a patch, which includes a mesh structural body forming microcavities and is configured to contain a staining reagent for staining staining targets present in blood in the microcavities, is used to perform a blood test through staining of the staining target, the blood testing method including placing blood in a reaction region and providing the staining reagent to the reaction region using the patch configured to contain the staining reagent.

The blood testing method may further include acquiring an image of the blood stained by the provided staining reagent.

The staining targets may be blood cells in the blood, and the blood testing method may further include acquiring at least one of a type information of the blood cells, a count information of the blood cells, and a morphological information of the blood cells on the basis of the image.

The blood testing method may further include performing a complete blood cell count (CBC) on the basis of the acquired information.

The staining targets may be parasites or bacteria in the blood, and the blood testing method may further include acquiring at least one of information related to presence of the parasites or bacteria, an information related to a type of the parasites or bacteria, information related to the parasites or bacteria, and a morphological information on the parasites or bacteria.

The blood testing method may further include performing a peripheral blood smear examination (CBC) on the basis of the acquired information.

The placing of the blood may be performed by any one of a method of fixing the blood to a plate, a method of smearing a sample on a plate, or a method of smearing a sample on a plate and fixing the sample to the plate.

The providing of the staining reagent to the reaction region using the patch may include bringing the patch into contact with the reaction region so that the staining reagent is movable to the reaction region, and separating the patch from the reaction region, and when the patch is separated from the reaction region, a residual staining reagent that has not reacted with the staining targets may be removed from the reaction region.

The blood testing method may further include absorbing the residual staining reagent and a foreign substance remaining in the reaction region from the reaction region using a washing patch configured to contain a washing liquid.

The providing of the staining reagent to the reaction region using the patch may include using a first patch configured to contain a first staining reagent for staining any one of a cytoplasm and a nucleus from among staining targets and providing the first staining reagent to the reaction region, and using a second patch configured to contain a second staining reagent for staining the other one of the cytoplasm and the nucleus from among the staining targets and providing the second staining reagent to the reaction region.

The blood testing method may further include providing an optimal pH for the reaction region using a first buffer patch configured to contain a buffer solution.

The providing of the optimal pH may be performed during at least one time point from among a time point between the providing of the first staining reagent and the providing of the second staining reagent and a time point after the providing of the second staining reagent.

The staining patch may contain the first staining reagent configured to stain the cytoplasm from among the staining targets and the second staining reagent configured to stain the nucleus from among the staining targets, and the providing of the staining reagent to the reaction region using the patch may include providing the first staining reagent and the second staining reagent to the reaction region so that the staining patch stains both the cytoplasm and the nucleus from among the staining targets.

After the providing of the first staining reagent and the second staining 20 reagent, the blood testing method may further include providing an optimal pH for the reaction region using a buffer patch configured to contain a buffer solution.

According to yet another aspect of the present disclosure, there is provided a blood test device, which is a blood test device using a patch, which includes a mesh structural body forming micro-cavities and is configured to contain a staining reagent for staining staining targets present in blood in the micro-cavities, to perform a blood test through staining of the staining target, the blood test device including a plate supporter configured to support a plate on which a reaction region is placed and blood is placed in the reaction region, a patch controller configured to use the patch, which is configured to contain the staining reagent, and control a relative position of the patch relative to the reaction region so that the staining reagent is provided to the reaction region, and a reaction detector configured to detect a result of staining of the staining target present in the blood in order to examine the blood.

1. Patch

1.1 Meaning of Patch

In the present application, a patch for managing a liquid substance is disclosed.

The liquid substance may mean a substance which is in a liquid state and can flow.

The liquid substance may be a substance formed of a single component having fluidity. Alternatively, the liquid substance may be a mixture that includes a substance formed of a plurality of components.

When the liquid substance is a substance formed of a single component, the liquid substance may be a substance formed of a single chemical element or a compound including a plurality of chemical elements.

When the liquid substance is a mixture, a portion of the substance formed of a plurality of components may serve as a solvent, and the other portion may serve as a solute. That is, the mixture may be a solution.

A plurality of components constituting the mixture which forms the substance may be uniformly distributed. Alternatively, the mixture including the substance formed of a plurality of components may be a uniformly mixed mixture. The substance formed of a plurality of components may include a solvent and a substance that is not dissolved in the solvent and is uniformly distributed.

A portion of the substance formed of a plurality of components may be non-uniformly distributed. The non-uniformly distributed substance may include non-uniformly distributed particle components in the solvent. In this case, the non-uniformly distributed particle components may be in a solid phase.

For example, a substance that may be managed using the patch may be in a state of 1) a liquid formed of a single component, 2) a solution, or 3) a colloid, or according to circumstances, may be in a state in which 4) solid particles are non-uniformly distributed within another liquid substance.

Hereinafter, the patch according to the present application will be described in more detail.

1.2 General Nature of Patch

1.2.1 Configuration

Figure 2:
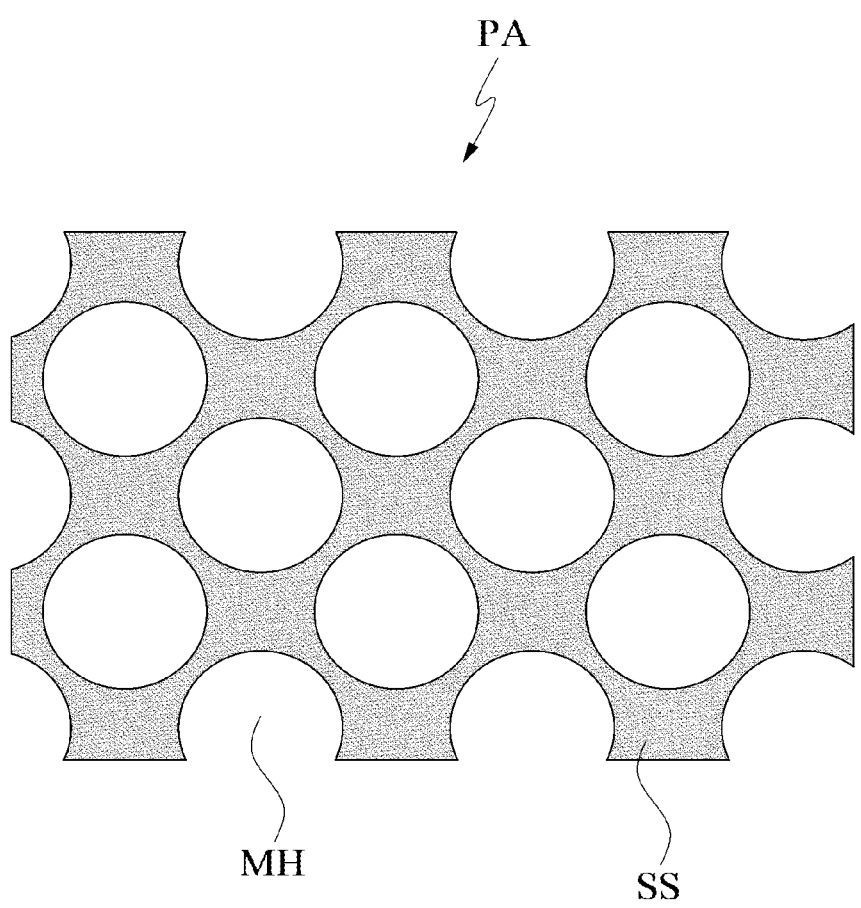
FIG. 2 illustrates an example of a patch in detail according to the present application.

FIGS. 1 and 2 are views illustrating an example of a patch according to the present application. The patch according to the present application will be described below with reference to FIGS. 1 and 2.

Referring to FIG. 1, a patch PA according to the present application may include a mesh structural body NS and a liquid substance.

As the liquid substance, a base substance BS and an additive substance AS may be taken into consideration separately.

The patch PA may be in a gel state(gel type). The patch PA may be implemented as a gel-type structural body in which colloidal molecules are bound and mesh tissues are formed.

The patch PA according to the present application is a structure for managing a liquid substance SB, and may include a three-dimensional mesh(net-like) structural body NS. The mesh structural body NS may be a continuously distributed solid structure. The mesh structural body NS may have a mesh structure in which a plurality of micro-threads are intertwined. However, the mesh structural body NS is not limited to the mesh form in which the plurality of micro-threads are intertwined, and may also be implemented in the form of an arbitrary three-dimensional matrix that is formed by connection of a plurality of micro-structures. For example, the mesh structural body NS may be a frame structural body that includes a plurality of micro-cavities. In other words, the mesh structural body NS may form a plurality of micro-cavities MC.

FIG. 2 illustrates a structure of a patch according to an embodiment of the present application. Referring to FIG. 2, the mesh structural body of the patch PA may have a sponge structure SS. The mesh structural body of the sponge structure SS may include a plurality of micro-holes MH. Hereinafter, the terms micro-holes MH and the micro-cavities MC may be used interchangeably, and unless particularly mentioned otherwise, the term micro-cavities MC is defined as encompassing the concept of the micro-holes MH.

The mesh structural body NS may have a regular or irregular pattern. Furthermore, the mesh structural body NS may include both a region having a regular pattern and a region having an irregular pattern.

A density of the mesh structural body NS may have a value within a predetermined range. Preferably, the predetermined range may be set within a limit in which the form of the liquid substance SB captured in the patch PA is maintained in a form that corresponds to the patch PA. The density may be defined as a degree to which the mesh structural body NS is dense or a mass ratio, a volume ratio, or the like that the mesh structural body NS occupies in the patch.

The patch according to the present application may manage the liquid substance SB by having a three-dimensional mesh structure.

The patch PA according to the present application may include the liquid substance SB, and the fluidity of the liquid substance SB included in the patch PA may be limited by the form of the mesh structural body NS of the patch PA.

The liquid substance SB may freely flow within the mesh structural body NS. In other words, the liquid substance SB is placed in the plurality of micro-cavities formed by the mesh structural body NS. An exchange of liquid substance SB may occur between neighboring micro-cavities. In this case, the liquid substance SB may be present in a state in which the liquid substance SB permeating into a frame structural body that forms the mesh tissues. In such a case, nano-sized pores into which the liquid substances SB may permeate may be formed in the frame structural body.

Further, whether to the liquid substance SB is filled in the frame structural body of the mesh structure may be determined depending on a molecular weight or a particle size of the liquid substance SB to be captured in the patch PA. A substance having a relatively large molecular weight may be captured in the micro-cavities, and a substance having a relatively small molecular weight may be captured by the frame structural body and filled in the micro-cavities and/or the frame structural body of the mesh structural body NS.

In the present specification, the term "capture" may be defined as a state in which the liquid substance SB is placed in the plurality of micro-cavities and/or nano-sized holes formed by the mesh structural body NS. As described above, the state in which the liquid substance SB is captured in the patch PA is defined as including a state in which the liquid substance SB may flow between the micro-cavities and/or the nano-sized holes.

As in the following, the base substance BS and the additive substance AS may be taken into consideration separately as the liquid substance SB.

The base substance BS may be a liquid substance SB having fluidity.

The additive substance AS may be a substance that is mixed with the base substance BS and has fluidity. In other words, the base substance BS may be a solvent. The additive substance AS may be a solute that is dissolved in the solvent or may be particles that are not melted in the solvent.

The base substance BS may be a substance capable of flowing inside a matrix formed by the mesh structural body NS. The base substance BS may be uniformly distributed in the mesh structural body NS or may be distributed only in a partial region of the mesh structural body NS. The base substance BS may be a liquid having a single component.

The additive substance AS may be a substance that is mixed with the base substance BS or dissolved in the base substance BS. For example, the additive substance AS may serve as a solute while the base substance BS is a solvent. The additive substance AS may be uniformly distributed in the base substance BS.

The additive substance AS may be fine particles that are not dissolved in the base substance BS. For example, the additive substance AS may include colloidal molecules and fine particles such as microorganisms.

The additive substance AS may include particles larger than the micro-cavities formed by the mesh structural body NS. When the size of the micro-cavities is smaller than the size of the particles included in the additive substance AS, fluidity of the additive substance AS may be limited.

According to an embodiment, the additive substance AS may include a component that is selectively included in the patch PA.

The additive substance AS does not necessarily refer to a substance that is lower in quantity or inferior in function in comparison to the above-described base substance BS.

Hereinafter, characteristics of the liquid substance SB captured in the patch PA may be presumed as characteristics of the patch PA. That is, the characteristics of the patch PA may depend on characteristics of a substance captured in the patch PA.

1.2.2 Characteristics

As described above, the patch PA according to the present application may include the mesh structural body NS. The patch PA may manage the liquid substance SB through the mesh structural body NS. The patch PA may allow the liquid substance SB captured in the patch PA to maintain at least some of its unique characteristics.

For example, diffusion of a substance may occur in a region of the patch PA in which the liquid substance SB is distributed, and a force such as surface tension may come into action.

The patch PA may provide a liquid environment in which diffusion of a target substance is caused due to thermal motion of a substance or a difference in density or concentration thereof. Generally, "diffusion" refers to a phenomenon in which particles that constitute a substance are spread from a side at which concentration is high to a side at which a concentration is low due to a difference in concentration. Such a diffusion phenomenon may be basically understood as a phenomenon that occurs due to motion of molecules (translational motion in a gas or liquid, vibrational motion in a solid, and the like). In the present application, in addition to referring to the phenomenon in which particles are spread from a side at which a concentration is high toward a side at which a concentration is low due to a difference in concentration or density, "diffusion" also refers to a phenomenon in which particles move due to irregular motion of molecules that occurs even when a concentration is uniform. The expression "irregular motion" may also have the same meaning as "diffusion" unless particularly mentioned otherwise. The diffused substance may be a solute that is dissolved in the liquid substance SB, and the diffused substance may be provided in a solid, liquid, or gas state.

More specifically, a non-uniformly-distributed substance in the liquid substance SB captured by the patch PA may be diffused in a space provided by the patch PA. In other words, the additive substance AS may be diffused in a space defined by the patch PA.

The non-uniformly-distributed substance or the additive substance AS in the liquid substance SB managed by the patch PA may be diffused within the micro-cavities provided by the mesh structural body NS of the patch PA. A region in which the non-uniformly-distributed substance or the additive substance AS may be diffused may be changed by the patch PA being connected or coming into contact with another substance.

Even when, after the concentration of the substance or the additive substance AS has become uniform, as a result of diffusion of the non-uniformly-distributed substance or the additive substance AS within the patch PA or within an external region connected to the patch PA, the substance or the additive substance AS may continuously move due to irregular motion of molecules inside the patch PA and/or within the external region connected to the patch PA.

The patch PA may be implemented to exhibit a hydrophilic or hydrophobic property. In other words, the mesh structural body NS of the patch PA may have a hydrophilic or hydrophobic property.

When properties of the mesh structural body NS and the liquid substance SB are similar, the mesh structural body NS may be able to manage the liquid substance SB more effectively.

The base substance BS may be a polar hydrophilic substance or a nonpolar hydrophobic substance. The additive substance AS may exhibit a hydrophilic or hydrophobic property.

The properties of the liquid substance SB may be related to the base substance BS and/or the additive substance AS. For example, when both the base substance BS and the additive substance AS are hydrophilic, the liquid substance SB may be hydrophilic, and when both the base substance BS and the additive substance AS are hydrophobic, the liquid substance SB may be hydrophobic. When polarities of the base substance BS and the additive substance AS are different, the liquid substance SB may be hydrophilic or hydrophobic.

When polarities of both the mesh structural body NS and the liquid substance SB are hydrophilic or hydrophobic, an attractive force may come into action between the mesh structural body NS and the liquid substance SB. When polarities of the mesh structural body NS and the liquid substance SB are opposite, e.g., when the polarity of the mesh structural body NS is hydrophobic and the polarity of the liquid substance SB is hydrophilic, a repulsive force may act between the mesh structural body NS and the liquid substance SB.

On the basis of the above-described properties, the patch PA may be solely used, a plurality of patches PA may be used, or the patch PA may be used with another medium to induce a desired reaction. Hereinafter, functional aspects of the patch PA will be described.

However, hereinafter, for convenience of description, the patch PA is assumed as being a gel type that may include a hydrophilic solution. In other words, unless particularly mentioned otherwise, the mesh structural body NS of the patch PA is assumed to have a hydrophilic property.

However, the scope of the present application should not be interpreted as being limited to the gel-type patch PA having a hydrophilic property. In addition to a gel-type patch PA that includes a solution exhibiting a hydrophobic property, a gel-type patch PA from which a solvent is removed and even a sol-type patch PA, as long as it is capable of implementing functions according to the present application, may belong to the scope of the present application.

2. Functions of Patch

Due to the above-described characteristics, the patch according to the present application may have some useful functions. In other words, by capturing the liquid substance SB, the patch may become involved in behavior of the liquid substance SB. Accordingly, hereinafter, in accordance with forms of behavior of the substance with respect to the patch PA, a reservoir function in which a state of the substance is defined in a predetermined region formed by the patch PA and a channeling function in which a state of the substance is defined in a region including an external region of the patch PA will be separately described.

2.1 Reservoir

2.1.1 Meaning

As described above, the patch PA according to the present application may capture the liquid substance SB. In other words, the patch PA may perform a function as a reservoir.

The patch PA may capture the liquid substance SB in the plurality of micro-cavities formed in the mesh structural body NS using the mesh structural body NS. The liquid substance SB may occupy at least a portion of the fine micro-cavities formed by the three-dimensional mesh structural body NS of the patch PA or be penetrated in the nano-sized pores formed in the mesh structural body NS.

The liquid substance SB placed in the patch PA does not lose properties of a liquid even when the liquid substance SB is distributed in the plurality of micro-cavities. That is, the liquid substance SB has fluidity even in the patch PA, and diffusion of a substance may occur in the liquid substance SB distributed in the patch PA, and an appropriate solute may be dissolved in the substance.

The reservoir function of the patch PA will be described below in more detail.

2.1.2 Containing

In the present application, the patch PA may capture a target substance due to the above-described characteristics. The patch PA may have resistance to a change in an external environment within a predetermined range. In this way, the patch PA may maintain a state in which the substance is captured therein. The liquid substance SB, which is a target to be captured, may occupy the three-dimensional mesh structural body NS.

Hereinafter, for convenience, the above-described function of the patch PA will be referred to as "containing."

However, "the patch PA containing the liquid substance" is defined to encompass a case in which the liquid substance is contained in a space formed by the mesh structure and/or a case in which the liquid substance is contained in the frame structural body constituting the mesh structural body NS.

The patch PA may contain the liquid substance SB. For example, the patch PA may contain the liquid substance SB, due to an attractive force that acts between the mesh structural body NS of the patch PA and the liquid substance SB. The liquid substance SB may be bound to the mesh structural body NS with an attractive force of a predetermined strength or higher and contained in the patch PA.

Properties of the liquid substance SB contained in the patch PA may be classified in accordance with properties of the patch PA. More specifically, when the patch PA exhibits a hydrophilic property, the patch PA may be bound to a hydrophilic liquid substance SB which is polar in general and contain the hydrophilic liquid substance SB in the three-dimensional micro-cavities. Alternatively, when the patch PA exhibits a hydrophobic property, the hydrophobic liquid substance SB may be contained in the micro-cavities of the three-dimensional mesh structural body NS.

The amount of substance that may be contained in the patch PA may be proportional to a volume of the patch PA. In other words, the amount of substance contained in the patch PA may be proportional to an amount of three-dimensional mesh structural body NS that serves as a support body that contributes to the form of the patch PA. However, there is no constant proportional factor between the amount of substance that may be contained in the patch PA and the volume of the patch PA, and thus the relationship between the amount of substance that may be contained in the patch PA and the volume of the patch PA may be changed in accordance with the design or manufacturing method of the mesh structure.

The amount of substance contained in the patch PA may be reduced due to evaporation, loss, etc. with time. The substance may be additionally injected into the patch PA to increase or maintain the content of the substance contained in the patch PA. For example, a moisture keeping agent for suppressing evaporation of moisture may be added to the patch PA.

The patch PA may be implemented in a form in which it is easy to store the liquid substance SB. This signifies that, when the substance is affected by environmental factors such as humidity level, amount of light, and temperature, the patch PA may be implemented to minimize denaturalization of the substance. For example, to prevent the patch PA from being denaturalized due to external factors such as bacteria, the patch PA may be treated with a bacteria inhibitor.

A liquid substance SB having a plurality of components may be contained in the patch PA. In this case, the substance formed of a plurality of components may be placed together in the patch PA before a reference time point, or a primarily-injected substance may be first contained in the patch PA and then a secondary substance may be contained in the patch PA after a predetermined amount of time. For example, when a liquid substance SB formed of two components is contained in the patch PA, the two components may be contained in the patch PA upon manufacturing the patch PA, only one component may be contained in the patch PA upon manufacturing the patch PA and the other component may be contained therein later, or the two components may be sequentially contained in the patch PA after the patch PA is manufactured.

As described above, the substance contained in the patch may exhibit fluidity, and the substance may move irregularly or be diffused due to molecular motion in the patch PA.

2.1.3 Providing of Reaction Space

Figure 3:
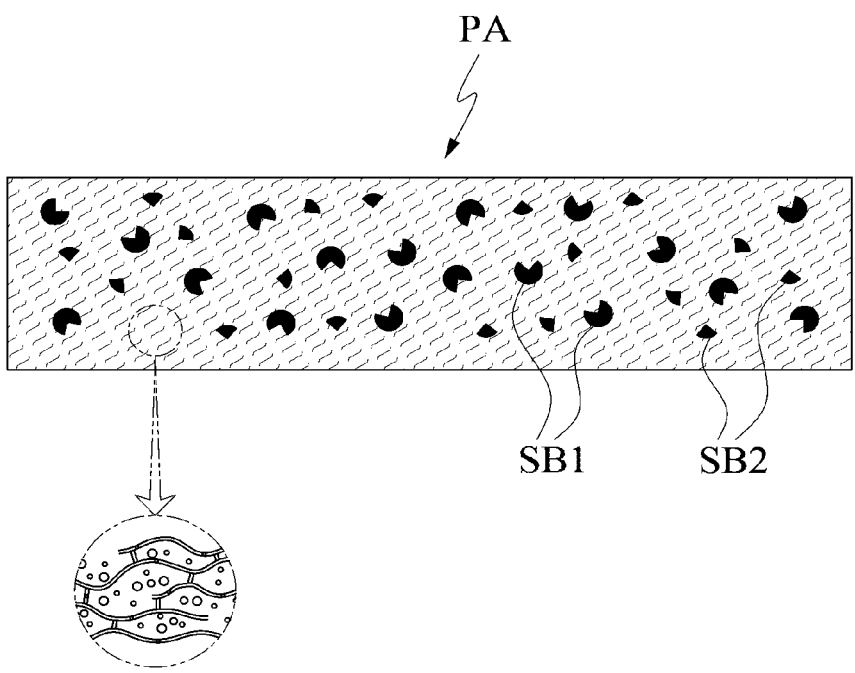
FIG. 3 illustrates providing of a reaction space as an example of a function of a patch according to the present application.
Figure 4:
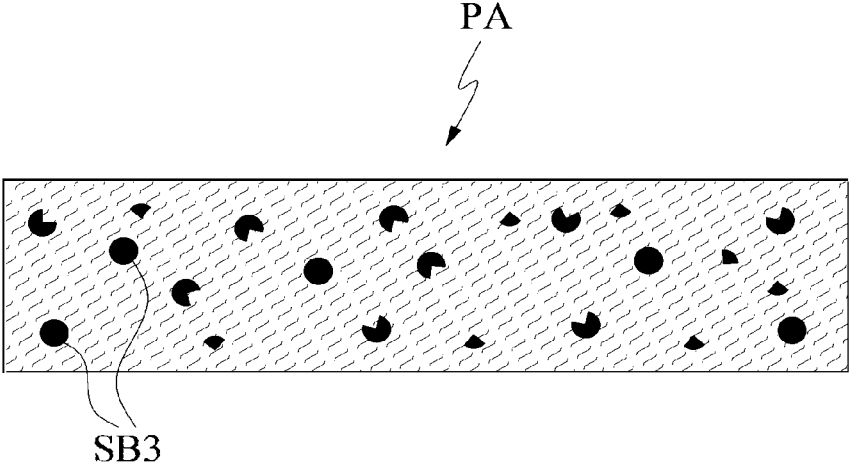
FIG. 4 illustrates providing of a reaction space as an example of a function of a patch according to the present application.

FIGS. 3 and 4 are views illustrating providing a reaction space as an example of a function of the patch according to the present application.

As illustrated in FIGS. 3 and 4, the patch PA according to the present application may perform a function of providing a space. In other words, the patch PA may provide a space in which the liquid substance SB may move through a space formed by the mesh structural body NS and/or a space constituting the mesh structural body NS.

The patch PA may provide a space for activity other than diffusion of particles and/or irregular motion of particles (hereinafter referred to as activity other than diffusion). The activity other than diffusion may refer to a chemical reaction, but is not limited thereto, and may also refer to a physical state change. More specifically, the activity other than diffusion may include a chemical reaction in which a chemical composition of the substance changes after the activity, a specific binding reaction between components included in the substance, homogenization of solutes or particles included in the substance and non-uniformly distributed therein, condensation of some components included in the substance, or a biological activity of a portion of the substance.

When a plurality of substances become involved in the activity, the plurality of substances may be placed together in the patch PA before a reference time point. The plurality of substances may be sequentially inserted into the patch PA.

By changing environmental conditions of the patch PA, efficiency of the function of providing a space for activities other than diffusion in the patch PA may be enhanced. For example, the activity may be promoted or a start of the activity may be induced by changing a temperature condition of the patch PA or adding an electrical condition thereto.

According to FIGS. 3 and 4, a first substance SB1 and a second substance SB2 placed in the patch PA may react inside the patch PA and be deformed into a third substance SB3 or generate the third substance SB3.

20.1 Channel

2.2.1 Meaning

Movement of a substance may occur between the patch PA and an external region. The substance may be moved from the patch PA to the external region of the patch PA or may be moved from the external region to the patch PA.

The patch PA may form a substance movement path or get involved in movement of the substance. More specifically, the patch PA may become involved in movement of the liquid substance SB captured in the patch PA or become involved in movement of an external substance through the liquid substance SB captured in the patch PA. The base substance BS or the additive substance AS may move out from the patch PA, or an external substance may be introduced from an external region to the patch PA.

The patch PA may provide a substance movement path. That is, the patch PA may become involved in movement of the substance and provide a substance movement channel. The patch PA may provide a substance movement channel based on unique properties of the liquid substance SB.

In accordance with whether the patch PA is connected to the external region, the patch PA may be in a state in which the liquid substance SB is movable between the patch PA and the external region or a state in which the liquid substance SB is immovable between the patch PA and the external region. When channeling between the patch PA and the external region begins, the patch PA may have unique functions.

Hereinafter, the state in which the substance is movable and the state in which the substance is immovable will be described first, and the unique functions of the patch PA will be described in detail in connection with whether the patch PA and the external region are connected.

Basically, irregular motion and/or diffusion of the substance are fundamental causes of movement of the liquid substance SB between the patch PA and the external region. However, controlling an external environmental factor (e.g., controlling a temperature condition, controlling an electrical condition, or the like) in order to control movement of a substance between the patch PA and the external region has already been described.

2.2.2 Movable State

In the state in which the substance is movable, a flow may occur between the liquid substance SB captured in the patch PA and/or the substance placed in the external region. In the state in which the substance is movable, substance movement may occur between the liquid substance SB captured in the patch PA and the external region.

For example, in the state in which the substance is movable, the liquid substance SB or some components of the liquid substance SB may be diffused to the external region or moved due to irregular motion. Alternatively, in the state in which the substance is movable, an external substance placed in the external region or some components of the external substance may be diffused to the liquid substance SB in the patch PA or moved due to irregular motion.

The state in which the substance is movable may be caused by contact. The contact may refer to connection between the liquid substance SB captured in the patch PA and the external region. Contact may refer to at least a partial overlap between a flow region of the liquid substance SB and the external region. The contact may refer to the external substance being connected to at least a portion of the patch PA. It may be understood that the range in which the captured liquid substance SB may flow is expanded in the state in which the substance is movable.

In other words, in the state in which the substance is movable, the range in which the liquid substance SB may flow may be expanded to include at least a portion of the external region of the captured liquid substance SB. For example, when the liquid substance SB is in contact with the external region, the range in which the captured liquid substance SB may flow may be expanded to include at least a portion of the external region in contact. More specifically, when the external region is an external plate, the region in which the liquid substance SB may flow may be expanded to include a region of the external plate in contact with the liquid substance SB.

2.2.3 Immovable State

In the state in which the substance is immovable, substance movement may not occur between the liquid substance SB captured in the patch PA and the external region. However, substance movement may respectively occur in the liquid substance SB captured in the patch PA and in external substance placed in the external region.

The state in which the substance is immovable may be a state in which the contact is released. In other words, in the state in which contact between the patch PA and the external region is released, substance movement is not possible between the liquid substance SB remaining in the patch PA and the external region or the external substance.

More specifically, the state in which the contact is released may refer to a state in which the liquid substance SB captured in the patch PA is not connected to the external region. The state in which the contact is released may refer to a state in which the liquid substance SB is not connected to an external substance placed in the external region. For example, the state in which movement of the substance is impossible may be caused by separation between the patch PA and the external region.

In the present specification, although "movable state" has a meaning differentiated from that of "immovable state," a transition may occur between the states due to an elapse of time, an environmental change, and the like. In other words, the patch PA may be in the immovable state after being in the movable state, in the movable state after being in the immovable state, or may be in the movable state again, after being in the immovable state after being in the movable state.

2.2.4 Differentiation of Functions

2.2.4.1 Delivery

In the present application, due to the above-described characteristics, the patch PA may deliver at least a portion of the liquid substance SB captured in the patch PA to a desired external region. The delivery of the substance may refer to separation of a portion of the liquid substance SB captured in the patch PA from the patch PA due to a predetermined condition being satisfied. The separation of the portion of the liquid substance SB may refer to the portion of the substance being extracted, emitted, or released from a region that is affected by the patch PA. This is a concept subordinate to the above-described channeling function of the patch PA, and may be understood as defining transfer(delivery) of the substance placed in the patch PA to the outside of the patch PA.

The desired external region may be another patch PA, a dried region, or a liquid region.

The predetermined condition for the delivery to occur may be set as an environmental condition such as a temperature change, a pressure change, a change in an electrical characteristic, and a change in a physical state. For example, when the patch PA is in contact with an object whose force of binding to the liquid substance SB is larger than a force of binding to the mesh structural body NS of the patch PA, the liquid substance SB may be chemically bound with the object in contact, and as a result, at least a portion of the liquid substance SB may be provided to the object.

Hereinafter, for convenience, the above-described function of the patch PA will be referred to as "delivery."

The delivery may occur between the patch PA and the external region, via the state in which the liquid substance SB is movable and the state in which the liquid substance SB is immovable between the patch PA and the external region.

More specifically, when the liquid substance SB is in the movable state, the liquid substance SB may be diffused between the patch PA and the external region or may be moved to the external region due to irregular motion. In other words, the base solution and/or the additive substance AS included in the liquid substance SB may be moved from the patch PA to the external region. In the state in which the liquid substance SB is immovable, the liquid substance SB is unable to move between the patch PA and the external region. In other words, due to a transition from the movable state to the immovable state, a portion of the substance that has moved from the patch PA to the external region due to diffusion and/or irregular motion of the liquid substance SB become unable to move back to the patch PA. Thus, a portion of the liquid substance SB may be provided to the external region.

The delivery may be performed due to a difference between an attractive force between the liquid substance SB and the mesh structural body NS and an attractive force between the liquid substance SB and the external region or the external substance. The attractive force may be caused by similarity between polarities or a specific binding relationship.

More specifically, when the liquid substance SB is hydrophilic and the external region or the external substance is more hydrophilic than the mesh structural body NS, at least a portion of the liquid substance SB captured in the patch PA may be provided to the external region via the movable state and the immovable state.

The delivery of the liquid substance SB may also be performed selectively. For example, when a specific binding relationship exists between some components included in the liquid substance SB and the external substance, some of the ingredients may be selectively delivered via the state in which the substance is movable and the state in which the substance is immovable.

More specifically, when it is assumed that the patch PA provides a substance to an external plate PL, which is in a form of a flat plate, a substance that binds specifically to a portion of the liquid substance SB captured in the patch PA (e.g., a portion of a solute) may be applied on the external plate PL. In this case, the patch PA may selectively deliver a portion of the solute that binds specifically to the substance applied on the external plate PL from the patch PA to the plate PL via the movable state and the immovable state.

The delivery as a function of the patch PA will be described below according to a few examples of different regions to which the substance is moved. However, in giving the detailed description, the concepts of "release" of the liquid substance SB and "delivery" of the liquid substance SB may be interchangeably used.

Here, a case in which the liquid substance SB is provided from the patch PA to a separate external plate PL will be described. For example, a case in which the substance is moved from the patch PA to a plate PL, such as a slide glass, may be taken into consideration.

As the patch PA and the plate PL come into contact, at least a portion of the liquid substance SB captured in the patch PA is diffused to the plate PL or moved due to irregular motion. When the contact between the patch PA and the plate PL is released, the portion of the substance that has been moved from the patch PA to the plate PL (that is, the portion of the liquid substance SB) become unable to move back to the patch PA. As a result, the portion of the substance may be provided from the patch PA to the plate PL. In this case, the portion of the substance being provided may be the additive substance AS. For a substance in the patch PA to be "provided" by the contact and separation, an attractive force and/or binding force that acts between the substance and the plate PL should be present, and the attractive force and/or the binding force should be larger than the attractive force acting between the substance and the patch PA. Therefore, if the above-described "delivery condition" is not satisfied, delivery of a substance may not occur between the patch PA and the plate PL.

The delivery of a substance may be controlled by providing a temperature condition or an electrical condition to the patch PA.

The movement of a substance from the patch PA to the plate PL may depend on an extent of a contact area between the patch PA and the plate PL. For example, the substance movement efficiency between the patch PA and the plate PL may be increased or decreased in accordance with an extent of an area in which the patch PA and the plate PL come into contact.

When the patch PA includes a plurality of components, only some of the components may be selectively moved to the external plate PL. More specifically, a substance that binds specifically to some of the plurality of components may be fixed to the external plate PL. In this case, the substance fixed to the external plate PL may be in a liquid or solid state, or may be fixed to a different region. In this case, a portion of the substance of the plurality of components moves to the plate PL and binds specifically to the plate PL due to contact between the patch PA and the different region, and when the patch PA is separated from the plate PL, only some of the components may be selectively released to the plate PL.

Figure 5:
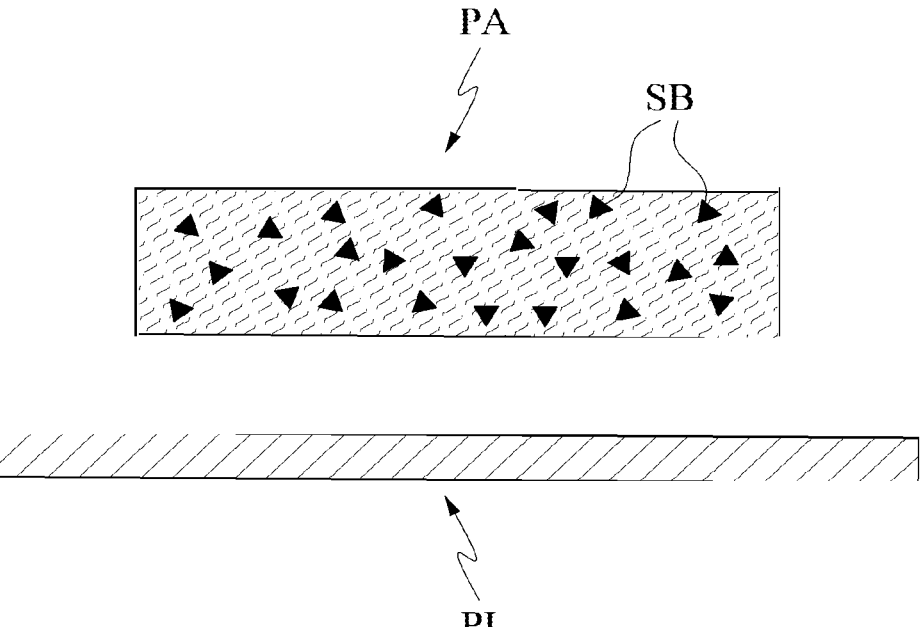
FIG. 5 illustrates providing of a substance as an example of a function of a patch according to the present application.
Figure 6:
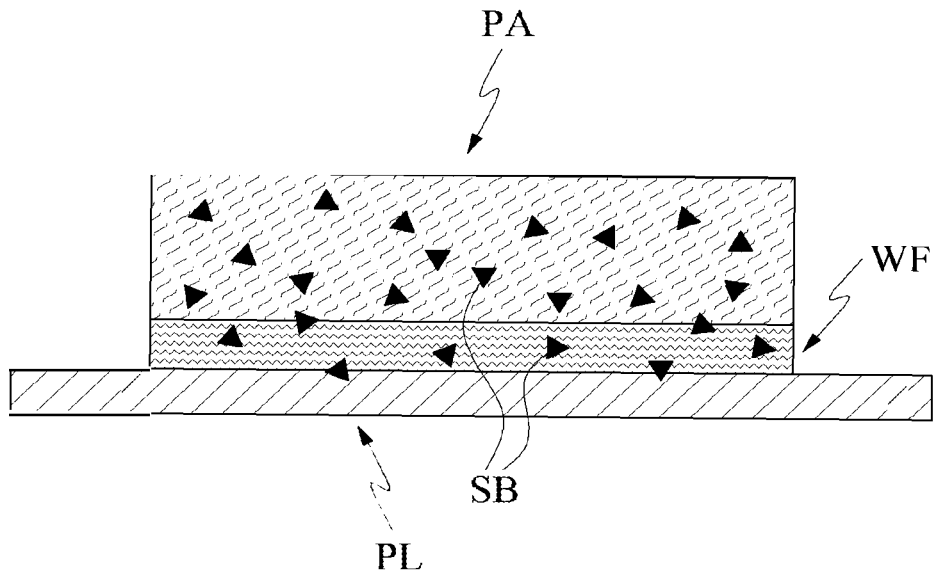
FIG. 6 illustrates providing of a substance as an example of a function of a patch according to the present application.

FIGS. 5 to 7 illustrate delivery of a substance from the patch PA to the external plate PL as an example of delivery of a substance from among the functions of the patch PA according to the present application. According to FIGS. 5 to 7, by the patch PA coming into contact with the external plate PL, a portion of a substance contained in the patch PA may be provided to the plate PL. In this case, providing of the substance may become possible by the patch PA coming into contact with the plate so that the substance is movable. In this case, a water film WF may be formed in the vicinity of a contact surface at which the plate and the patch PA come into contact, and the substance may be movable through the formed water film WF.

Here, a case in which the liquid substance SB is provided from the patch PA to a substance having fluidity SL will be described. The substance having fluidity SL may be a liquid substance that is held in other containing space or that is flowing.

As the patch PA and the substance having fluidity come into contact (for example, the patch PA is put into a solution), at least a portion of the liquid substance SB captured in the patch PA may be diffused or moved due to irregular motion to the substance having fluidity SL. When the patch PA and the substance having fluidity SL are separated, a portion of the liquid substance SB that has been moved from the patch PA to the substance having fluidity become unable to move back to the patch PA so that a portion of the substance in the patch PA may be provided to the substance having fluidity.

The substance movement between the patch PA and the substance having fluidity SL may depend on an extent of a contact area between the patch PA and the substance having fluidity SL. For example, the substance movement efficiency between the patch PA and the substance having fluidity SL may be increased or decreased in accordance with an extent of an area at which the patch PA and the substance having fluidity SL come into contact (for example, a depth at which the patch PA is immersed into a solution or the like).

The substance movement between the patch PA and the substance having fluidity SL may be controlled through physical separation between the patch PA and the substance having fluidity.

A partial concentration of the additive substance AS in the liquid substance SB and a partial concentration of the additive substance AS in the substance having fluidity may be different, and the additive substance AS may be provided from the patch PA to the substance having fluidity.

However, in the patch PA providing the liquid substance SB to the substance having fluidity SL, the physical separation between the patch PA and the substance having fluidity SL is not essential. For example, when a force (driving force/casual force) that causes a substance to move from the patch PA to a liquid having fluidity disappears or is decreased to a reference value or lower, the movement of the substance may be stopped.

In "delivery" between the patch PA and the substance having fluidity SL, the above-described "delivery condition" between the patch PA and the substance having fluidity SL may not be required. It may be understood that substances that have already moved to the substance having fluidity SL are diffused and/or moved due to irregular motion in the substance having fluidity SL, and the substance has been provided to the substance having fluidity SL when a distance between the moved substance and the patch PA become larger a predetermined distance. Since, while in the case of the plate PL, a movable range expanded due to the contact is extremely limited, and thus the attractive force between the patch PA and the substances that have moved to the plate PL may be significant, in the relationship between the patch PA and the substance having fluidity, a movable range expanded due to contact between the patch PA and the plate PL is relatively much wider, and thus the attractive force between the patch PA and the substances that have moved to the substance having fluidity SL is insignificant.

Figure 9:
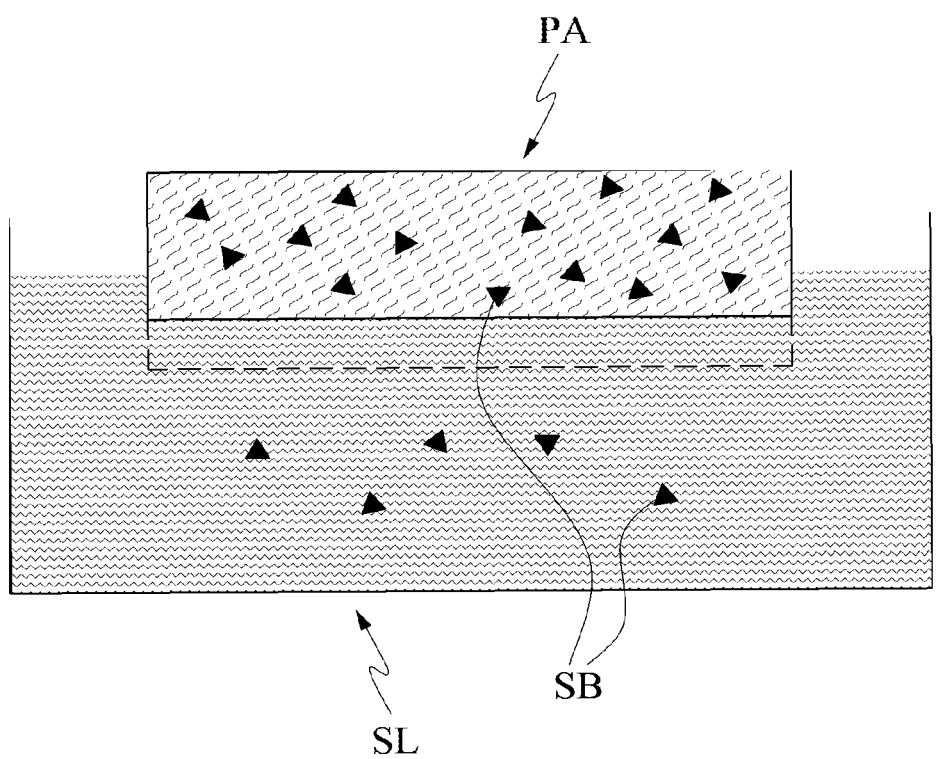
FIG. 9 illustrates providing of a substance as an example of a function of a patch according to the present application.
Figure 10:
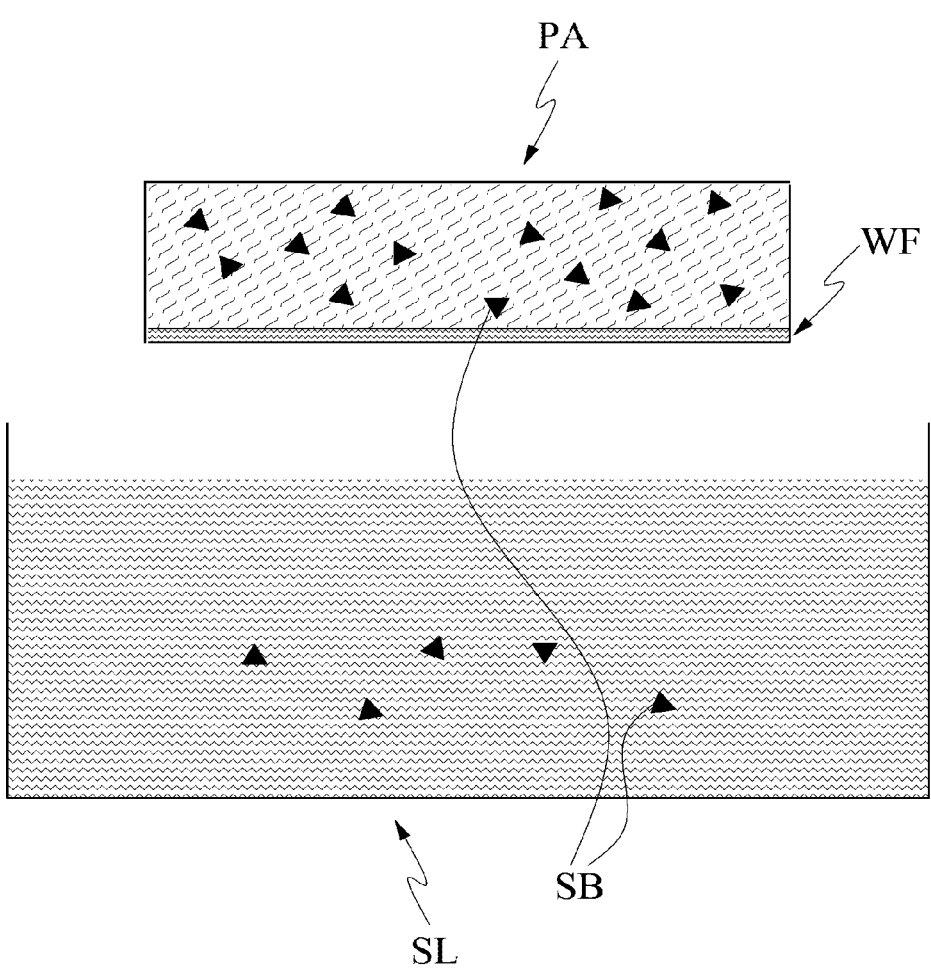
FIG. 10 illustrates providing of a substance as an example of a function of a patch according to the present application.

FIGS. 8 to 10 illustrate delivery of a substance from the patch PA to the substance having fluidity as an example of delivery of a substance from among the functions of the patch PA according to the present application. According to FIGS. 8 to 10, the patch PA may deliver a portion of a substance contained in the patch PA to an external substance having fluidity. The delivery of the portion of the contained substance may be performed by the patch PA being inserted into or coming into contact with the substance having fluidity so that substance movement is possible between the liquid substance SB captured in the patch PA and the substance having fluidity.

Here, it is assumed that a substance is moved from the patch PA to another patch PA. In a contact region in which the patch PA and the other patch PA are in contact, at least a portion of the liquid substance B provided in the patch PA may be moved to the other patch PA.

In the contact region, the liquid substance SB provided in each patch PA may be diffused and moved to the other patch PA. In this case, due to the movement of the substance, a concentration of the liquid substance SB provided in each patch PA may be changed. Also in the present embodiment, as described above, the patch PA and the other patch PA may be separated, and a portion of the liquid substance SB in the patch PA may be provided to the other patch PA.

The substance movement between the patch PA and the other patch PA may be performed through a change in an environmental condition including a change in a physical state.

The substance movement between the patch PA and another patch PA may depend on an extent of a contact area between the patch PA and the other patch PA. For example, the substance movement efficiency between the patch PA and the other patch PA may be increased or decreased in accordance with an extent of an area where the patch PA comes into contact with the other patch PA.

Figure 11:
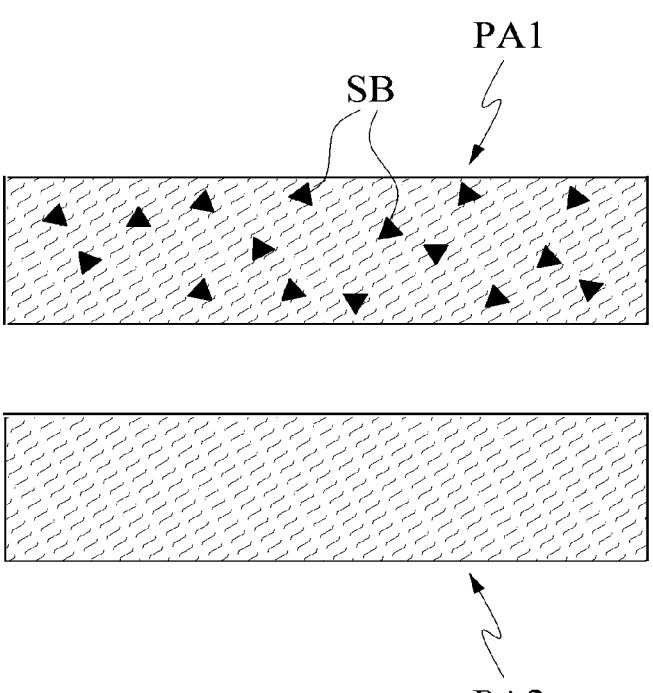
FIG. 11 illustrates providing of a substance as an example of a function of a patch according to the present application.
Figure 12:
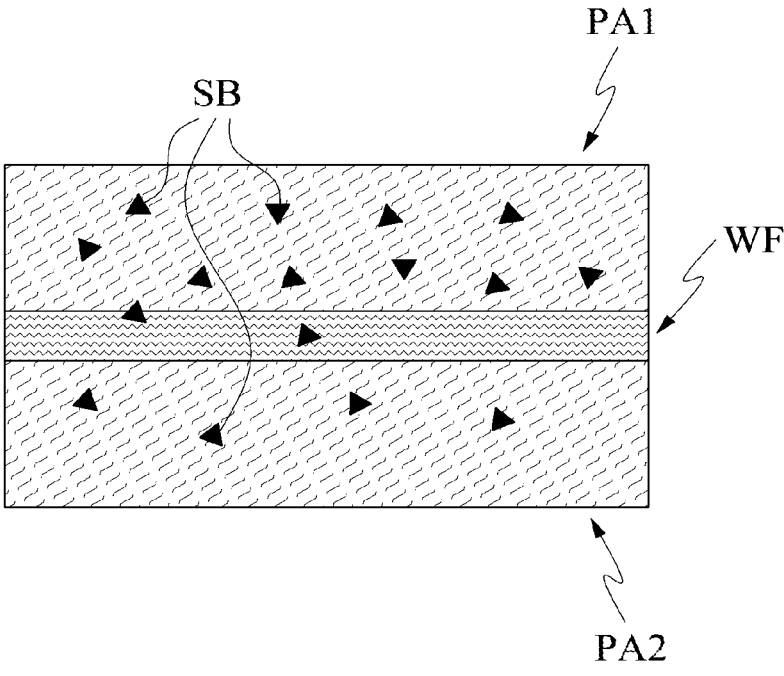
FIG. 12 illustrates providing of a substance as an example of a function of a patch according to the present application.
Figure 13:
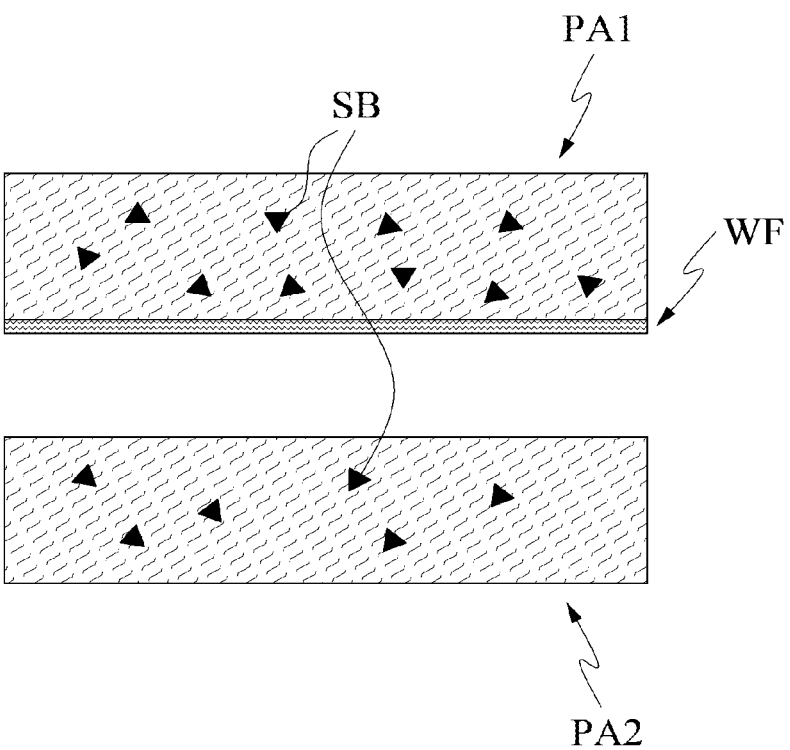
FIG. 13 illustrates providing of a substance as an example of a function of a patch according to the present application.

FIGS. 11 to 13 illustrate delivery of a substance from a patch PA1 to another patch PA2 as an example of delivery of a substance among the functions of the patch 25 PA according to the present application. According to FIGS. 11 to 13, the patch PA1 may deliver a portion of a substance contained in the patch PA1 to the other patch PA2. The delivery of the portion of the substance may be performed by the patch PA1 coming into contact with the other patch PA2 and becoming a state in which a liquid substance SB captured in the patch PA1 and a substance captured in the other patch PA2 are exchangeable.

2.2.4.2 Absorption

Prior to description, it should be noted that, among the functions of the patch PA according to the present application, "absorption" may be managed similarly as the above-described "delivery" in some embodiments. For example, in a case in which a substance moves due to a concentration differences between substances, the "absorption" may be similar to the "delivery" in that a concentration of the liquid substance SB, particularly, a concentration of the additive substance AS, may be changed to control a direction in which the substance is moved. The "absorption" may also be similar to "delivery" in terms of controlling movement and selective absorption of a substance through a release of physical contact with the patch PA, and this may be clearly understood by those of ordinary skill in the art to which the present application pertains.

Due to the above-described characteristics, the patch PA according to the present application may capture an external substance. The patch PA may pull in an external substance present outside a region defined by the patch PA toward a region affected by the patch PA. The pulled external substance may be captured along with the liquid substance SB of the patch PA. The pulling of the external substance may be caused by an attractive force between the external substance and the liquid substance SB already captured in the patch PA. Alternatively, the pulling of the external substance may be caused by an attractive force between the external substance and a region of the mesh structural body NS not occupied by the liquid substance SB. The pulling of the external substance may be caused by a force of surface tension.

Hereinafter, for convenience, the above-described function of the patch PA will be referred to as "absorption." Absorption may be understood as a concept subordinate to the above-described channeling function of the patch PA, the concept defining movement of an external substance to the patch PA.

The absorption may occur by the patch PA via a state in which the substance is movable and a state in which the substance is immovable.

A substance that is absorbable by the patch PA may be in a liquid or solid state. For example, when the patch PA comes into contact with an external substance including a solid state substance, absorption of the substance may be performed due to an attractive force between the solid state substance included in the external substance and the liquid substance SB placed in the patch PA. As another example, when the patch PA comes into contact with a liquid external substance, the absorption may be performed due to binding between the liquid external substance and the liquid substance SB placed in the patch PA.

The external substance absorbed into the patch PA may be moved to the inside of the patch PA through the micro-cavities of the mesh structural body NS forming the patch PA or may be distributed on a surface of the patch PA. Positions at which the external substance is distributed may be set on the basis of a molecular weight or a particle size of the external substance.

While the absorption is performed, the form of the patch PA may be changed. For example, the volume, color, and the like of the patch PA may be changed.

While the absorption into the patch PA is being performed, the absorption into the patch PA may be activated or delayed by adding external conditions such as a temperature change and a physical state change to an absorption environment of the patch PA.

The absorption will be described below as a function of the patch PA according to some examples of an external region that provides a substance to be absorbed into the patch PA when the absorption occurs.

Hereinafter, it will be assumed that the patch PA absorbs an external substance from an external plate PL. An example of the external plate may include a plate PL in which the external substance may be placed while the external substance is not absorbed thereinto.

A substance may be applied on the external plate PL. Particularly, a substance may be applied in a form of powder on the plate PL. The substance applied on the plate PL may be a single component or a mixture of a plurality of components.

The plate PL may have the shape of a flat plate. The shape of the plate PL may be deformed for improvement in ability to contain the substance or the like. For example, a well may be formed to improve the ability to contain the substance, a surface of the plate PL may be deformed by engraving or embossing, or a patterned plate PL may be used to improve contact with the patch PA.

The absorption of a substance from the plate PL by the patch PA according to the present application may be performed through contact between the plate PL and the patch PA. In this case, in a contact region in the vicinity of a contact surface between the plate PL and the patch PA, a water film WF may be formed due to the liquid substance SB captured in the patch PA and/or the substance applied on the plate PL. When the water film (aquaplane, hydroplane) WF is formed in the contact region, the substance applied on the plate PL may be captured by the water film WF. The substance captured in the water film WF may freely flow within the patch PA.

When the patch PA is spaced a predetermined distance or more apart and separated from the plate PL, the water film WF may be moved along with the patch PA, and the substance applied on the plate PL may be absorbed into the patch PA. The substance applied on the plate PL may be absorbed into the patch PA as the patch PA is separated a predetermined distance or more apart from the plate PL. When the patch PA and the plate PL are spaced apart and separated, the liquid substance SB provided to the patch PA may not be moved to the plate PL, or only an insignificant amount thereof may be absorbed into the patch PA.

A portion of or the entire substance applied on the plate PL may react specifically with a portion of or the entire substance captured in the patch PA. In this respect, absorption of a substance from the plate PL by the patch PA may be selectively performed. Particularly, the absorption may be performed selectively when the patch PA has a stronger attractive force than the plate PL with respect to a portion of the substance captured in the patch PA.

As an example, a portion of the substance may be fixed to the plate PL. In other words, a portion of the substance may be fixed to the plate PL while another portion of the substance is applied to have fluidity or not be fixed. In this case, when the patch PA and the plate PL are brought into contact and separated, the substance, excluding the portion of the substance fixed to the plate PL of the substance applied on the plate PL, may be selectively absorbed into the patch PA. Instead, the selective absorption may also occur due to polarities of a substance placed on the plate PL and a substance captured in the patch PA regardless of whether the substance is fixed.

As another example, when the liquid substance SB captured in the patch PA is bound specifically to at least a portion of a substance applied on the plate PL, only the portion of the substance applied on the plate PL bound specifically to the liquid substance SB may be absorbed into the patch PA when the patch PA is brought into contact with and then separated from the substance applied on the plate PL.

As yet another example, a portion of the substance applied on the plate PL may react specifically with a substance fixed to the plate PL in advance. In this case, only a remaining substance, excluding the substance that reacts specifically with the substance fixed to the plate PL in advance of the substance being applied to the plate PL, may be absorbed into the patch PA.

Figure 15:
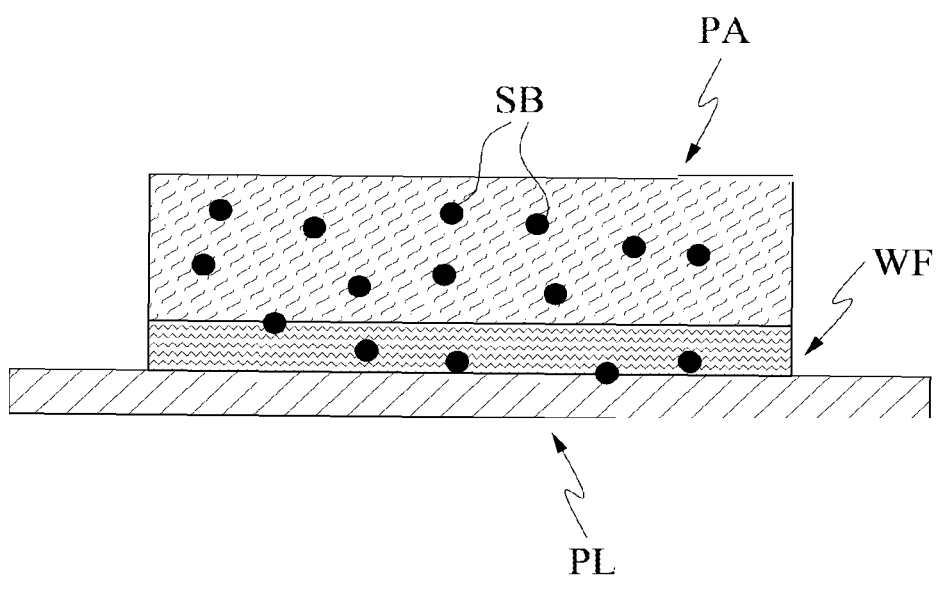
FIG. 15 illustrates absorbing of a substance as an example of a function of a patch according to the present application.

FIGS. 14 to 16 illustrate absorption of a substance from an external plate PL by the patch PA as an example of absorption of a substance from among the functions of the patch PA according to the present application. According to FIGS. 14 to 16, the patch PA may absorb a portion of a substance placed on the external plate PL from the external plate PL. The absorption of the substance may be performed by the patch PA coming into contact with the external plate PL, the water film WF being formed in the vicinity of a contact region between the external plate PL and the patch PA, and the substance being movable to the patch PA through the water film WF.

Here, it will be assumed that a substance is absorbed into the patch PA from the substance having fluidity SL. The substance having fluidity SL may refer to a liquid external substance that is held in other containing space or that is flowing. More specifically, by having an environment in which the substance having fluidity SL and the liquid substance SB captured in the patch PA may flow to and from each other, a portion of or the entire substance having fluidity SL may be absorbed into the patch PA. In this case, the environment in which the substance having fluidity SL and the liquid substance SB may flow to and from each other may be formed by the patch PA coming into contact with at least a portion of the substance having fluidity SL.

When the patch PA comes into contact with the substance having fluidity SL, the patch PA may be in a state in which a substance is movable from the substance having fluidity SL. When the patch PA is separated from the substance having fluidity SL, at least a portion of the substance having fluidity SL may be absorbed into the patch PA.

The absorption of a substance into the patch PA from the substance having fluidity SL may depend on a concentration difference between the substance captured in the patch PA and the substance having fluidity SL. In other words, when the concentration of the liquid substance SB captured in the patch PA with respect to a predetermined additive substance AS is lower than the concentration of the substance having fluidity SL with respect to the predetermined additive substance AS, the predetermined additive substance AS may be absorbed into the patch PA.

When a substance is absorbed into the patch PA from the substance having fluidity SL, in addition to the absorption depending on the concentration difference while the patch PA and the substance having fluidity SL are in contact as described above, the absorption into the patch PA may also be controlled by adding an electrical factor or changing a physical condition. Further, without direct contact between the substance captured in the patch PA and a substance to be absorbed, the absorption of a substance may also be performed through indirect contact therebetween via a medium.

Figure 18:
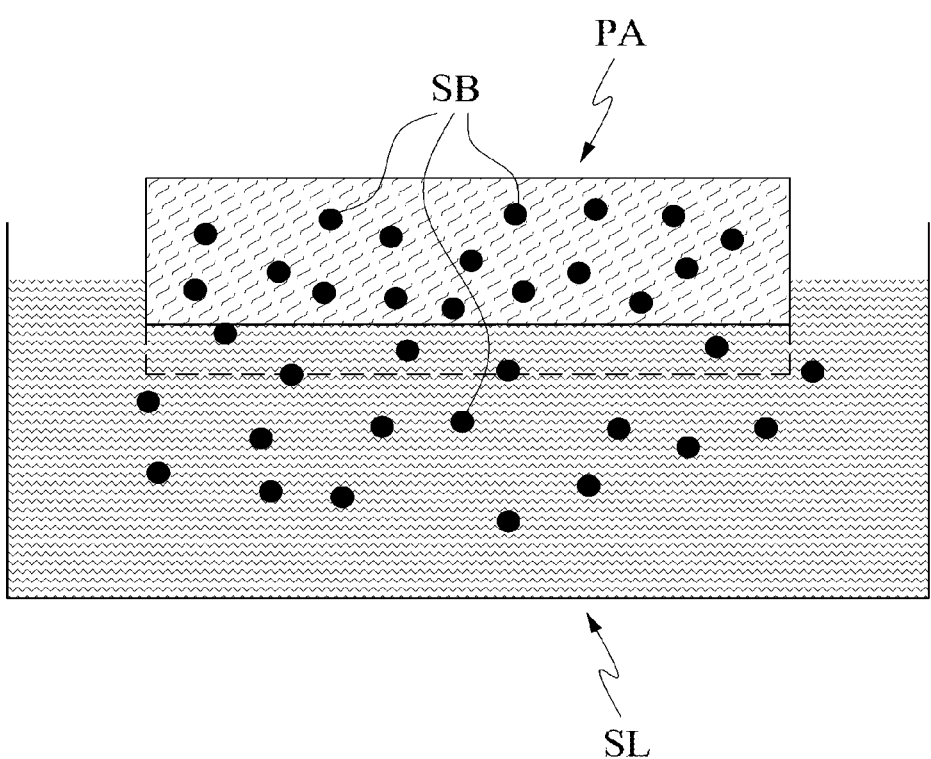
FIG. 18 illustrates absorbing of a substance as an example of a function of a patch according to the present application.
Figure 19:
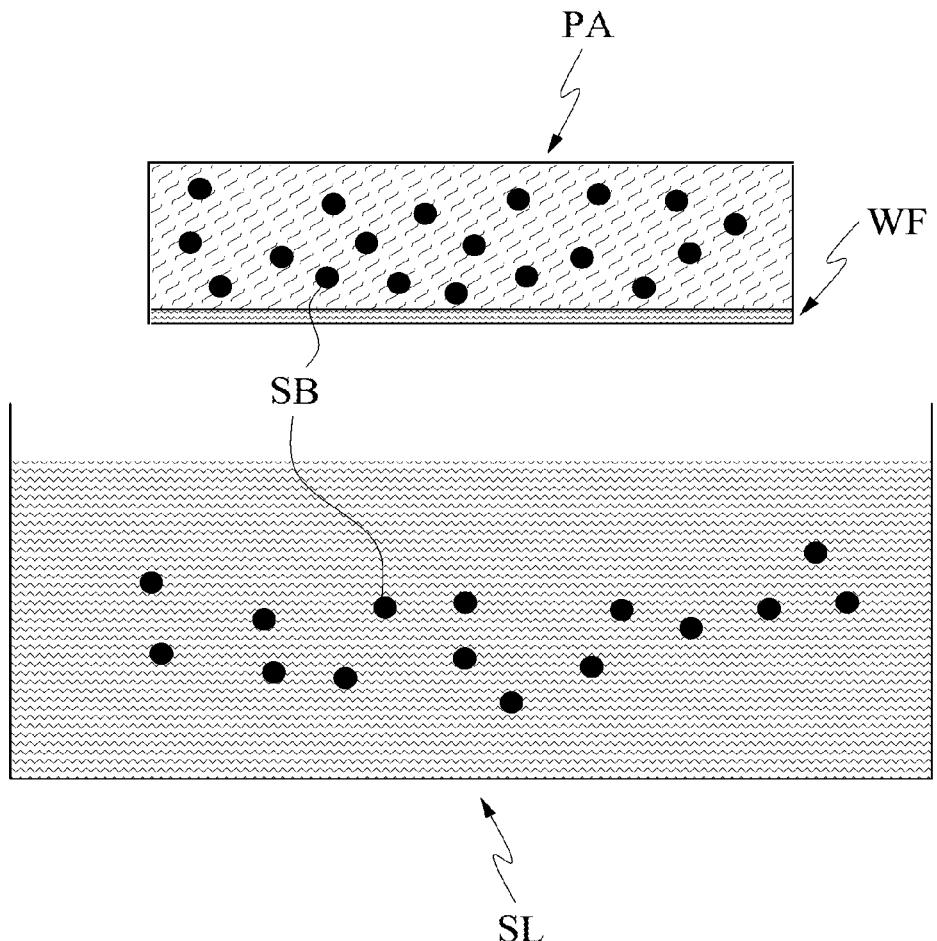
FIG. 19 illustrates absorbing of a substance as an example of a function of a patch according to the present application.

FIGS. 17 to 19 illustrate absorption of a substance from the substance having fluidity SL by the patch PA as an example of absorption of a substance from among the functions of the patch PA according to the present application. According to FIGS. 17 to 19, the patch PA may absorb a portion of the substance having fluidity SL. The absorption of a substance may be performed by the patch PA being immersed into the substance having fluidity SL or coming into contact with the substance having fluidity SL so that the liquid substance SB captured in the patch PA and the substance having fluidity SL are movable to and from each other.

Here, it will be assumed that the patch PA absorbs an external substance from another patch PA.

The absorption of an external substance from another patch PA by the patch PA may be performed due to a difference in binding force between the absorbed external substance and the substance already captured in the patch PA and between the absorbed external substance and the external substance not absorbed into the patch PA. For example, when the absorbed substance exhibits hydrophilic property, the patch PA exhibits hydrophilic property, and an attractive force between the absorbed substance and the patch PA is stronger than an attractive force between the other patch PA and the absorbed substance (that is, when the patch PA is more hydrophilic than the other patch PA), at least a portion of the external substance may be absorbed into the patch PA when the patch PA and the other patch PA are separated after being brought into contact.

Figure 20:
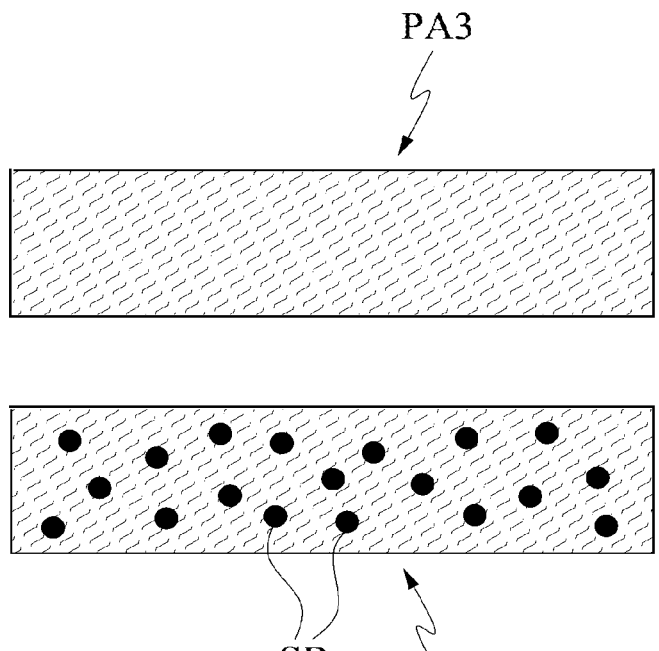
FIG. 20 illustrates absorbing of a substance as an example of a function of a patch according to the present application.
Figure 21:
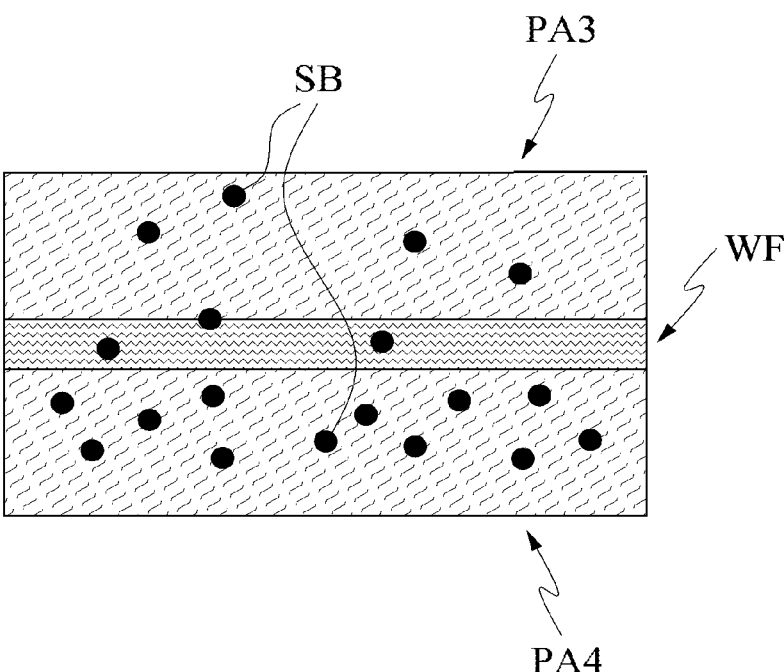
FIG. 21 illustrates absorbing of a substance as an example of a function of a patch according to the present application.
Figure 22:
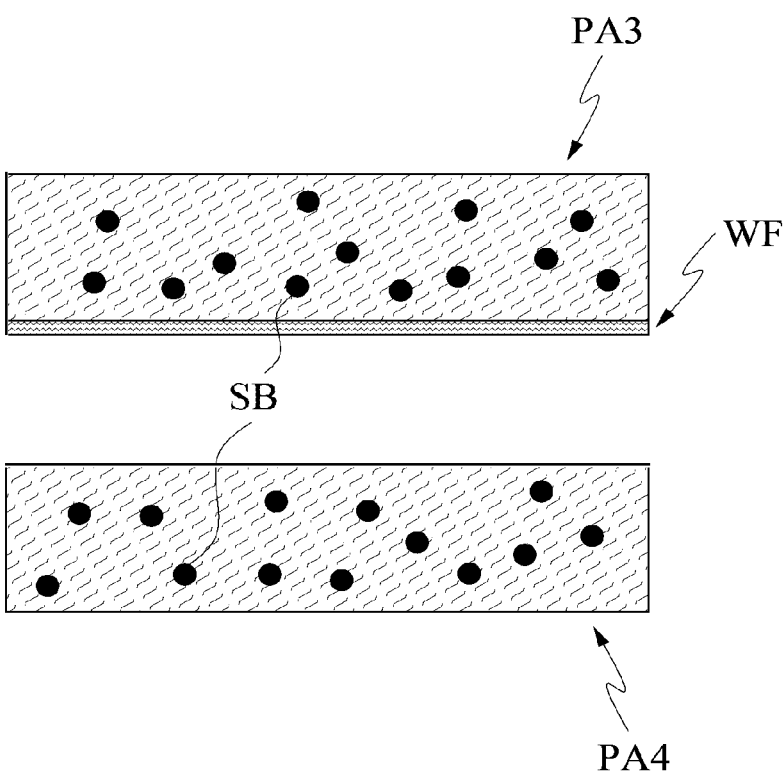
FIG. 22 illustrates absorbing of a substance as an example of a function of a patch according to the present application.

FIGS. 20 to 22 illustrate absorption of a substance from another patch PA4 by a patch PA3 as an example of absorption of a substance among the functions of the patch PA according to the present application. According to FIGS. 20 to 22, the patch PA3 may absorb a portion of a substance placed in the other patch PA4. The absorption of the substance may be performed by the patch PA3 coming into contact with the other patch PA4 so that a liquid substance SB captured in the patch PA3 and a liquid substance SB captured in the other patch PA4 are exchangeable.

A binding force of the patch PA to the external substance absorbed thereinto may be changed in accordance with a proportion of a frame structural body of the three-dimensional mesh structural body NS constituting the patch PA with respect to the total volume of the patch PA. For example, as the proportion of a volume occupied by the frame structural body in the entire patch PA increases, the amount of substance captured in the structural body may be reduced. In this case, a binding force between the patch PA and a target substance may be reduced due to a reason such as reduction in a contact area between the target substance and the substance captured in the patch PA.

In relation to this, ratios of materials that constitutes the mesh structural body NS may be adjusted during manufacturing process of the patch PA so that polarity of the patch PA is controlled. For example, in the case of a patch PA manufactured using agarose, a concentration of the agarose may be controlled to adjust a degree of the absorption.

When the certain region has a weaker binding force than the patch PA with respect to a substance provided from the patch PA, and the patch PA and another patch PA are brought into contact and then separated, the absorbed external substance may be separated from the other patch PA along with the patch PA.

2.2.4.3 Providing of Environment

Due to the above-described characteristics, the patch PA according to the present application may perform a function of adjusting an environmental condition of a desired region. The patch PA may provide an environment due to the patch PA to the desired region.

The environmental condition due to the patch PA may depend on the liquid substance SB captured in the patch PA. The patch PA may create a desired environment in a substance placed in an external region on the basis of characteristics of a substance accommodated in the patch PA or for a purpose of making the environment correspond to characteristics of the substance accommodated in the patch PA.

The adjustment of the environment may be understood as changing an environmental condition of the desired region. The changing of the environmental condition of the desired region may be implemented in a form in which a region affected by the patch PA is expanded to include at least a portion of the desired region or a form in which an environment of the patch PA is shared with the desired region.

Hereinafter, for convenience, the above-described function of the patch PA will be referred to as "providing of an environment."

The providing of an environment by the patch PA may be performed in a state in which a substance is movable between the patch PA and an external region subject to provide the environment. The providing of an environment by the patch PA may be performed through contact. For example, when the patch PA comes into contact with a desired region (for example, an external substance, a plate PL, or the like), a specific environment may be provided to the desired region by the patch PA.

The patch PA may adjust an environment of a target region TA by providing an environment with an appropriate pH, osmotic pressure, humidity level, concentration, temperature, and the like. For example, the patch PA may provide fluidity (liquidity) to the target region TA or a target substance. Such providing of fluidity may occur due to movement of a portion of a substance captured in the patch PA. A moist environment may be provided to the target region TA through the liquid substance SB or the base substance BS captured in the patch PA.

The environmental factors provided by the patch PA may be constantly maintained in accordance with a purpose. For example, the patch PA may provide 10 homeostasis to the desired region. As another example, as a result of providing an environment, the substance captured in the patch PA may be adapted to an environmental condition of the desired region The providing of an environment by the patch PA may result from diffusion of the liquid substance SB included in the patch PA. That is, when the patch PA and the desired region come into contact, a substance may be movable through a contact region that is formed due to contact between the patch PA and the desired region. In relation to this, an environmental change due to an osmotic pressure, an environmental change due to a change in ionic concentration, providing of a moist environment, and a change in a pH level may be implemented in accordance with a direction in which the substance is diffused.

Figure 24:
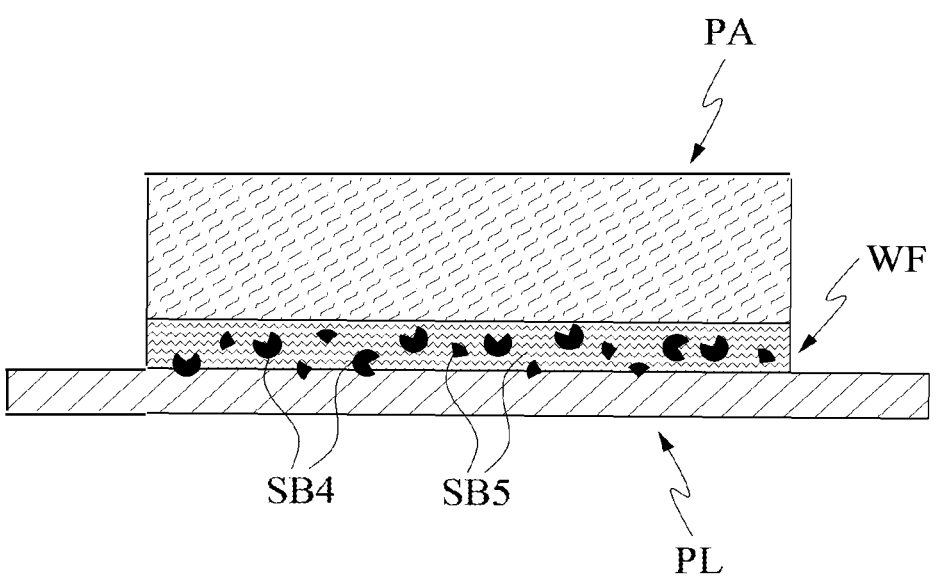
FIG. 24 illustrates providing of an environment as an example of a function of a patch according to the present application.

FIGS. 23 to 25 illustrate providing of a predetermined environment to an external plate PL by the patch PA as an example of providing of an environment among the functions of the patch PA according to the present application. According to FIGS. 23 to 25, the patch PA may provide a predetermined environment to an external plate PL on which a fourth substance SB4 and a fifth substance SB5 are placed. For example, the patch PA may provide a predetermined environment to the plate PL for the fourth substance SB4 and the fifth substance SB5 to react and form a sixth substance SB6. The providing of the environment may be performed by the patch PA coming into contact with the plate PL so that a water film WF is formed in the vicinity of a contact region and the fourth substance SB4 and the fifth substance SB5 are captured in the water film WF.

3. Application of Patch

The patch PA according to the present application may be implemented to perform various functions by suitably applying the above-described functions of the patch PA.

The technical spirit of the present application will be described below by disclosing some embodiments. However, the technical scope to which functions of the patch PA disclosed by the present application are applied may be interpreted in a broad sense within the scope that may be easily derived by those of ordinary skill in the art, and the scope of the present application should not be interpreted as being limited by the embodiments disclosed herein.

3.1. In-Patch

The patch PA may provide a reaction region for a substance. In other words, a reaction of a substance may occur in at least a portion of a spatial region affected by the patch PA. In this case, the reaction of a substance may be a reaction between liquid substances SB captured in the patch PA and/or a reaction between the captured liquid substance SB and a substance provided from the outside of the patch PA. The providing of a reaction region for a substance may activate or promote a reaction of a substance.

In this case, the liquid substance SB captured in the patch PA may include at least one of a substance added upon manufacturing the patch PA, a substance additive into the patch PA after the manufacturing of the patch PA and contained in the patch PA, and a substance temporarily captured in the patch PA. In other words, regardless of a form in which a substance is captured in the patch PA, any substance captured in the patch PA at a time point at which a reaction in the patch PA is activated may react in the patch PA. Further, a substance injected after the manufacturing of the patch PA may also act as a reaction initiator.

The providing of a reaction region for a reaction related to the liquid substance SB captured in the patch PA may be a concept subordinate, in terms of embodiment, to the above-described Section 2.1.3 (that is, providing of reaction space). Alternatively, the providing of a reaction region for a reaction related to the liquid substance SB captured in the patch PA may consist of multiple concepts that perform combined functions of the above-described Section 2.1.3 and Section 2.2.4.2 (that is, absorption). The providing of a reaction region for a reaction related to the liquid substance SB captured in the patch PA is not limited thereto and may be implemented in the form in which two or more functions are combined.

3.1.1 First Embodiment

Hereinafter, description will be given by assuming that the function of absorption into the patch PA and the function of providing of a reaction space (hereinafter referred to as "providing function") are performed by a single patch PA. In this case, the absorption function and the providing function may be simultaneously-performed functions, functions performed at different time points, or functions sequentially performed to perform another function. The patch PA further including other functions in addition to the absorption and providing functions may also be considered as belonging to the present embodiment.

As described above, the patch PA may perform a function of capturing a substance, and the substance may have fluidity even when the substance is captured.

When some components of the liquid substance SB are non-uniformly distributed, the non-uniform components may be diffused. Even when components of the liquid substance SB are uniformly distributed, the liquid substance SB may have a predetermined level of mobility due to irregular motion of particles. In this case, a reaction between substances, for example, specific binding between substances, may occur inside the patch PA.

For example, in the patch PA, in addition to a reaction between captured substances, a reaction in a form in which a substance having fluidity that is newly captured in the patch PA and the substance that has been captured in the patch PA bind specifically to each other may also be possible.

The reaction between the substance having fluidity and the substance that has been captured in the patch PA may also occur after the substance patch being separated from an space that has been provided. For example, after the patch PA absorbs the substance having fluidity from an arbitrary space, the patch PA may be separated from the arbitrary space, and a reaction between the absorbed substance and the substance that has been captured in the patch PA may occur in the patch PA.

In addition, the patch PA may allow a reaction of a substance captured therein to occur by performing the absorption function with respect to a substance having fluidity. In other words, the absorption of the substance having fluidity by the patch PA may act as a trigger for a reaction between the absorbed substance and the substance that has been captured in the patch PA. The reaction may occur inside a space defined by the patch PA.

A composition of the liquid substance SB captured in the patch PA may be changed due to the reaction occurring inside the patch PA. When, particularly, a substance captured inside the patch PA is a compound, a chemical composition thereof may be changed before and after a reaction. Alternatively, a composition distribution of a substance may be changed in accordance with a position of the substance in the patch PA. For example, this may be due to diffusion or particles having an attractive force specific to another substance.

When the composition of the liquid substance SB is changed due to a reaction inside the patch PA, a portion of the substance may be absorbed into the patch PA due to a concentration difference between the patch PA and a substance outside the patch PA (when a substance in contact with the patch PA is present, the corresponding substance), or the substance may be released from the patch PA to the substance outside the patch PA.

3.1.2 Second Embodiment

Hereinafter, an embodiment in which the containing function of the patch PA and the function of providing of a reaction space for a substance are performed together for at least a predetermined amount of time will be described. More specifically, the patch PA may perform a function of providing a space for at least a portion of the liquid substance SB contained in the patch PA to react.

The patch PA may contain a substance and provide a reaction space for the contained substance. In this case, the reaction space provided by the patch PA may be the microcavities formed by the mesh structural body NS of the patch PA or a surface region of the patch PA. Particularly, when a substance contained in the patch PA and a substance applied on a surface of the patch PA react, the reaction space may be the surface region of the patch PA.

The reaction space provided by the patch PA may serve to provide a specific environmental condition. While a reaction occurs in the liquid substance SB placed in the patch PA, an environmental condition of the reaction may be adjusted by the patch PA. For example, the patch PA may serve as a buffer solution.

By containing a substance through a mesh structure, the patch PA does not require a container, separately. When the reaction space of the patch PA is a surface of the patch PA, a reaction may be easily observed through the surface of the patch PA. For this, the shape of the patch PA may be deformed into a shape that facilitates the observation.

The liquid substance SB contained in the patch PA may be denaturalized or react with a different type of substance. The composition of the liquid substance SB contained in the patch PA may be changed with time.

The reaction may refer to a chemical reaction in which a chemical formula is changed, a physical state change, or a biological reaction. In this case, the liquid substance SB contained in the patch PA may be a substance formed of a single component or a mixture including a plurality of components.

3.2 Providing of Movement Path (Channeling)

Hereinafter, the patch PA that performs a function of providing a substance movement path will be described. More specifically, as described above, the patch PA may capture, absorb, release, and/or contain a substance having fluidity.

Various embodiments of the patch PA that performs the function of providing a substance movement path may be implemented by each of the above-described functions of the patch PA or a combination thereof. However, a few embodiments will be disclosed for a better understanding.

3.2.1 Third Embodiment

The patch PA may be implemented to perform functions described in Section 2.2.4.1 (that is, the section related to delivery) and Section 2.2.4.2 (that is, the section related to absorption) among the above-described functions of the patch PA. In this case, the absorption function and the delivery function may be provided together or sequentially provided.

The patch PA may perform the absorption and delivery functions together to provide a substance movement path. Particularly, the patch PA may absorb an external substance and provide the absorbed external substance to an external region, thereby providing a movement path to the external substance.

The providing of the movement path of the external substance by the patch PA may be performed by absorbing the external substance and releasing the external substance. More specifically, the patch PA may come into contact with the external substance, absorb the external substance, come into contact with the external region, and deliver the external substance to the external region. In this case, the capturing of the external substance and the delivery of the captured external substance to the external region by the patch PA may be performed through a process similar to those of the above-described absorption and delivery.

The external substance absorbed into the patch PA and provided may be in a liquid phase or a solid phase.

In this way, the patch PA may allow a portion of the external substance to be provided to another external substance. The external substance and the other external substance may simultaneously come into contact with the patch PA. The external substance and the other external substance may come into contact with the patch PA at different time points.

The external substance and the other external substance may come into contact with the patch PA at different time points. When the external substances come into contact with the patch PA at different time points, the external substance may come into contact with the patch PA first, and after the external substance and the patch PA are separated, the patch PA and the other external substance may come into contact. In this case, the patch PA may temporarily contain a substance captured from the external substance.

The patch PA may simultaneously provide a substance movement path and additionally provide a time delay. The patch PA may perform a function of suitably adjusting an amount of substance provided to another external substance and a speed of such providing.

Such a series of processes may be carried out in one direction with respect to the patch PA. As a specific example, absorption of a substance may be performed through a surface of the patch PA, an environment may be provided in an inner space of the patch PA, and the substance may be released through another surface facing the surface.

3.2.2 Fourth Embodiment

The patch PA may perform the absorbing and releasing of a substance among the above-described functions of the patch PA and the providing of a reaction space for the substance simultaneously. In this case, the absorption and release of the substance and the providing of the reaction space may be performed simultaneously or sequentially.

According to an embodiment, in performing the processes of absorbing and releasing an external substance, the patch PA may provide a reaction space to the absorbed external substance for at least a predetermined amount of time. The patch PA may provide a specific environment for at least some time to the liquid substance SB captured in the patch PA, including the absorbed external substance.

The liquid substance SB that has been captured in the patch PA and the external substance captured in the patch PA may react inside the patch PA. The external substance absorbed into the patch PA may be affected by an environment provided by the patch PA. The substance released from the patch PA may include at least a portion of a substance generated through the reaction. The external substance may be released from the patch PA after the composition, characteristics, and the like of the external substance are changed.

The absorbed substance may be released from the patch PA. The external substance being absorbed into the patch PA and being released from the patch PA may be understood as the external substance passing through the patch PA. The external substance that has passed through the patch PA may lose integrity due to a reaction inside the patch PA or an influence of an environment provided by the patch PA.

The above-described processes of absorption of an external substance, reaction of a substance, and providing of the substance may be carried out in one direction. In other words, the absorption of a substance may be performed at one position of the patch PA, the providing of an environment may be performed at another position of the patch PA, and the release of the substance may be performed at yet another position of the patch PA.

Figure 27:
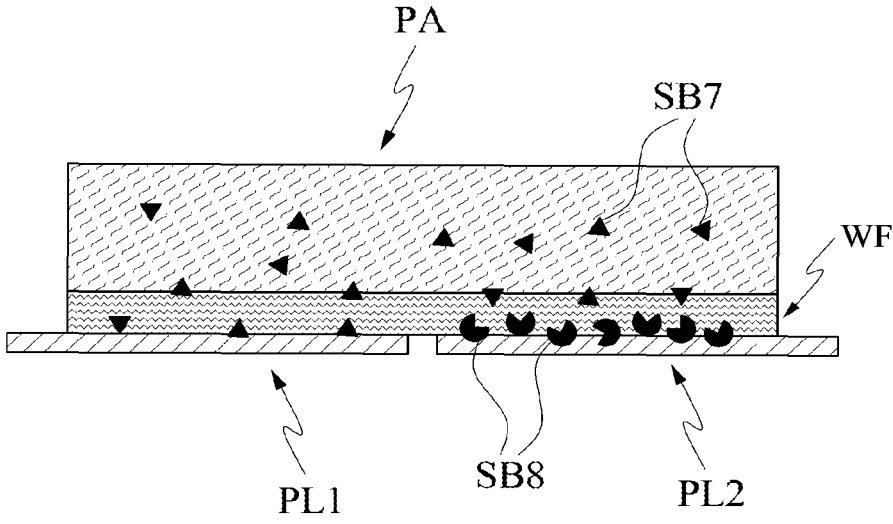
FIG. 27 illustrates performance of absorbing and providing of a substance as an embodiment of a patch according to the present application.
Figure 28:
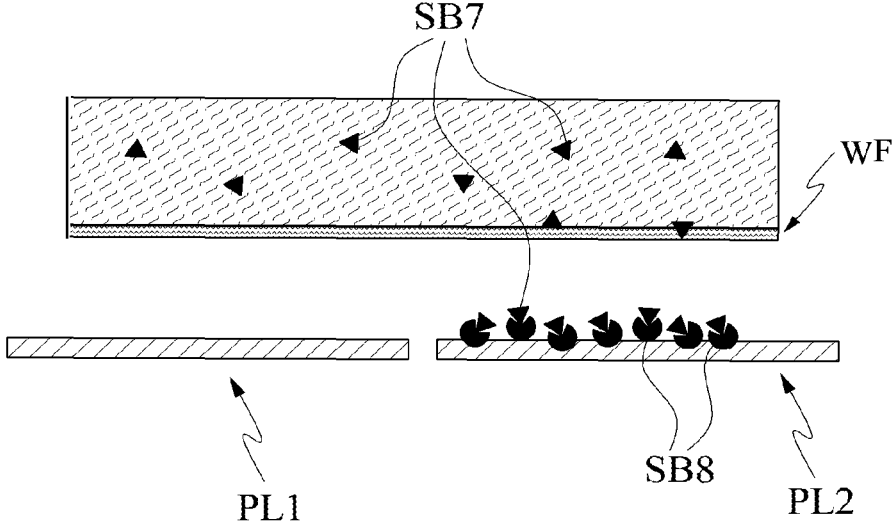
FIG. 28 illustrates performance of absorbing and providing of a substance as an embodiment of a patch according to the present application.

FIGS. 26 to 28 illustrate providing of a substance movement path between two plates PL as an embodiment of the patch PA according to the present application. According to FIGS. 26 to 28, the patch PA may provide a substance movement path between a plate PL1 on which a seventh substance SB7 is applied and a plate PL2 on which an eighth substance SB8 is applied. As a specific example, when the seventh substance SB7 is capable of binding to the eighth substance, and the eighth substance is fixed to the plate PL2, the patch PA may come into contact with the plates PL1 and PL2 so that the seventh substance SB7 is moved through the patch PA and bound to the eighth substance SB8. The seventh substance SB7 and the eighth substance SB8 may be connected to the patch PA through a water film WF formed by the patch PA coming into contact with the plates PL1 and PL2.

Figure 29:
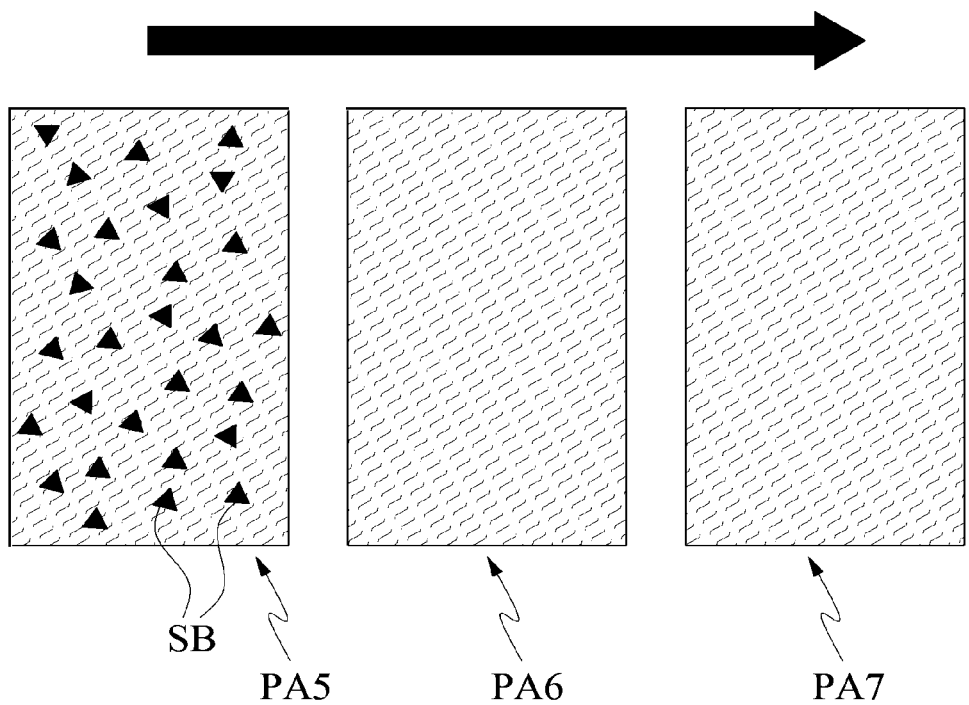
FIG. 29 illustrates performance of absorbing and providing of a substance as an embodiment of a patch according to the present application.
Figure 30:
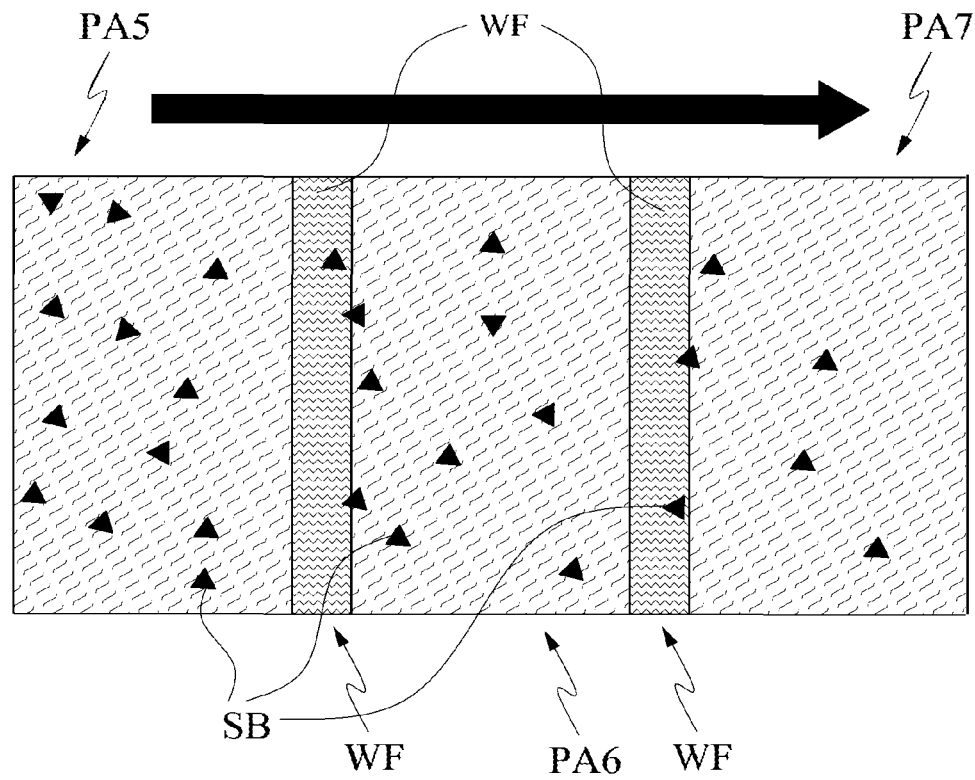
FIG. 30 illustrates performance of absorbing and providing of a substance as an embodiment of a patch according to the present application.

FIGS. 29 and 30 illustrate providing of a substance movement path between two patches as an embodiment of the patch PA according to the present application. According to FIGS. 29 and 30, a patch PA6 configured to provide the movement path may be in contact with a patch PAS configured to contain a substance to be moved, and a patch PA7 configured to receive the substance to be moved. The patch PA6 configured to provide the movement path may come into contact with the patch PAS configured to contain the substance to be moved and the patch PA7 configured to receive the substance to be moved, and the substance to be moved may be moved to the patch PA7 configured to receive the substance to be moved. The movement of the substance between the patches may be performed by a water film WF formed in the vicinity of a contact region between the patches.

Figure 31:
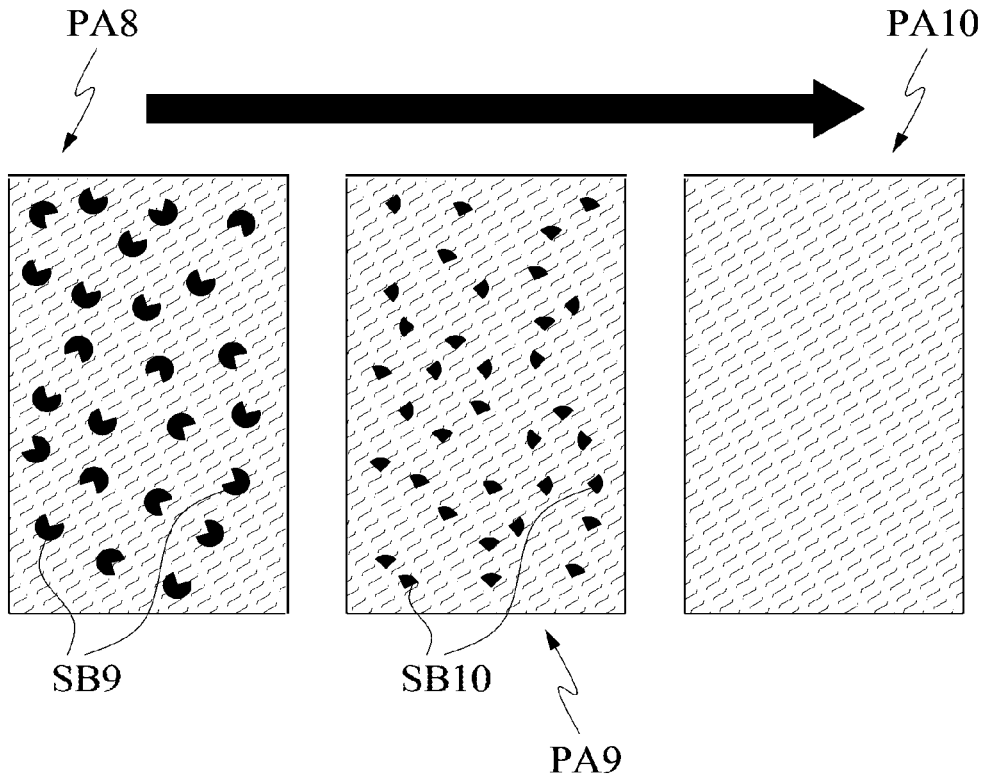
FIG. 31 illustrates performance of absorbing and providing of a substance and providing of an environment as an embodiment of a patch according to the present application.
Figure 32:
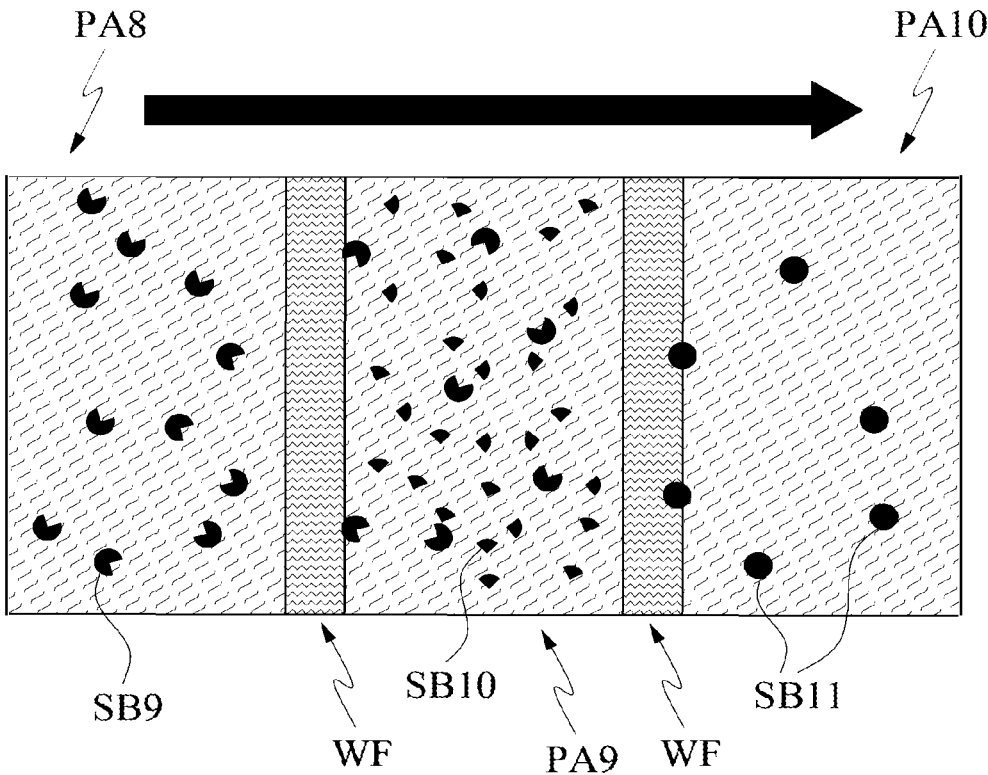
FIG. 32 illustrates performance of absorbing and providing of a substance and providing of an environment as an embodiment of a patch according to the present application.

FIGS. 31 and 32 illustrate providing of a substance movement path between two patches as an embodiment of the patch according to the present application. According to FIGS. 29 and 30, a patch PA9 configured to provide the movement path may be in contact with a patch PA8 configured to contain a ninth substance SB9 and a patch PA10 configured to receive a substance. The patch PA9 providing the movement path may come into contact with the patch PA8 configured to contain the ninth substance SB9 to absorb the ninth substance SB9. The absorbed ninth substance SB9 may react with a tenth substance SB10 contained in the patch PA9, which is configured to provide the movement path, and generate an eleventh substance. An eleventh substance SB11 may be provided from the patch PA9 configured to provide the movement path to the patch PA10 configured to receive the substance. The movement of a substance between the patches PA may be performed through a water film WF formed in the vicinity of a contact region between the patches PA.

3.3 Multi-Patch

A patch PA may be solely used, or a plurality of patches PA may be used together. In this case, the plurality of patches PA being able to be used together includes a case in which the plurality of patches PA are sequentially used as well as a case in which the plurality of patches PA are used simultaneously.

When the plurality of patches PA are used simultaneously, the patches PA may perform different functions. Although each patch PA of the plurality of patches PA may contain the same substance, the plurality of patches PA may also contain different substances.

When the plurality of patches PA are used simultaneously, the patches PA may not come into contact with each other such that substance movement does not occur between the patches PA, or a desired function may be performed in a state in which substances contained in the patches PA are exchangeable.

Although the plurality of patches PA used together may be manufactured in shapes similar to each other or in the same size, the plurality of patches PA may be used together even when the plurality of patches PA have different shapes. Each patch PA constituting the plurality of patches PA may be manufactured such that densities of the mesh structural bodies NS are different or components constituting the mesh structural bodies NS are different.

3.3.1 Contact with Plurality of Patches

When a plurality of patches PA are used, the plurality of patches PA may come into contact with a single target region TA. The plurality of patches PA may come into contact with the single target region TA and perform a desired function.

When a plurality of target regions TA are present, the plurality of patches PA may come into contact with different target regions TA. When the plurality of target regions TA are present, the plurality of patches PA may respectively come into contact with corresponding target regions TA and perform a desired function.

The plurality of patches PA may come into contact with a substance applied on the target region TA. In this case, the substance applied on the target region TA may be fixed or have fluidity.

The desired function may be a function of providing or absorbing the substance. However, each patch PA does not necessarily provide the same substance or absorb the same substance, and the patches PA may provide different substances to the target region TA or absorb different components from a substance placed in the target region TA.

The desired function may be different for each patch PA constituting the plurality of patches PA. For example, one patch PA may perform the function of providing a substance to the target region TA, and another patch PA may perform the function of absorbing the substance from the target region TA.

The plurality of patches PA may include different substances, and the different substances may be provided to a single target region TA and used to induce a desired reaction. When a plurality of components of a substance is required for the desired reaction to occur, the plurality of components may be contained in a plurality of patches PA respectively and provided to the target region TA. Such use of the plurality of patches PA may be particularly useful when properties of substances required for a desired reaction are lost or altered when the substances required for the reaction being mixed for reasons such as being contained in a single patch PA.

According to an embodiment, when the plurality of patches PA include substances formed of different components, and the substances formed of different components have different specific binding relationships, the substances formed of different components may be provided to the target region TA. The plurality of patches PA may be used to detect a plurality of specific bindings from the substances applied on the target region TA, by providing the substances including different components.

According to another embodiment, the plurality of patches PA may include substances formed of the same component, but each patch PA may have a different concentration with respect to the substance formed of the same component. The plurality of patches PA including the substances formed of the same component may come into contact with the target region TA and be used to determine an influence in accordance with a concentration of the substance included in the plurality of patches PA.

When the plurality of patches PA are used as described above, the patches PA may be grouped into more efficient forms and used. In other words, the configuration of the plurality of patches PA being used may be changed every time the plurality of patches PA are used. The plurality of patches PA may be manufactured in the form of a cartridge and used. In this case, the form of each patch PA being used may be suitably standardized and manufactured.

The plurality of patches PA in the form of a cartridge may be suitable when patches PA configured to contain a plurality of types of substances are manufactured to be used by being chosen as necessary.

Particularly, when attempting to detect a specific reaction of each substance from the target region TA using a plurality of types of substances, a combination of specific reactions to be detected may be changed every time the detection is performed.

Figure 33:
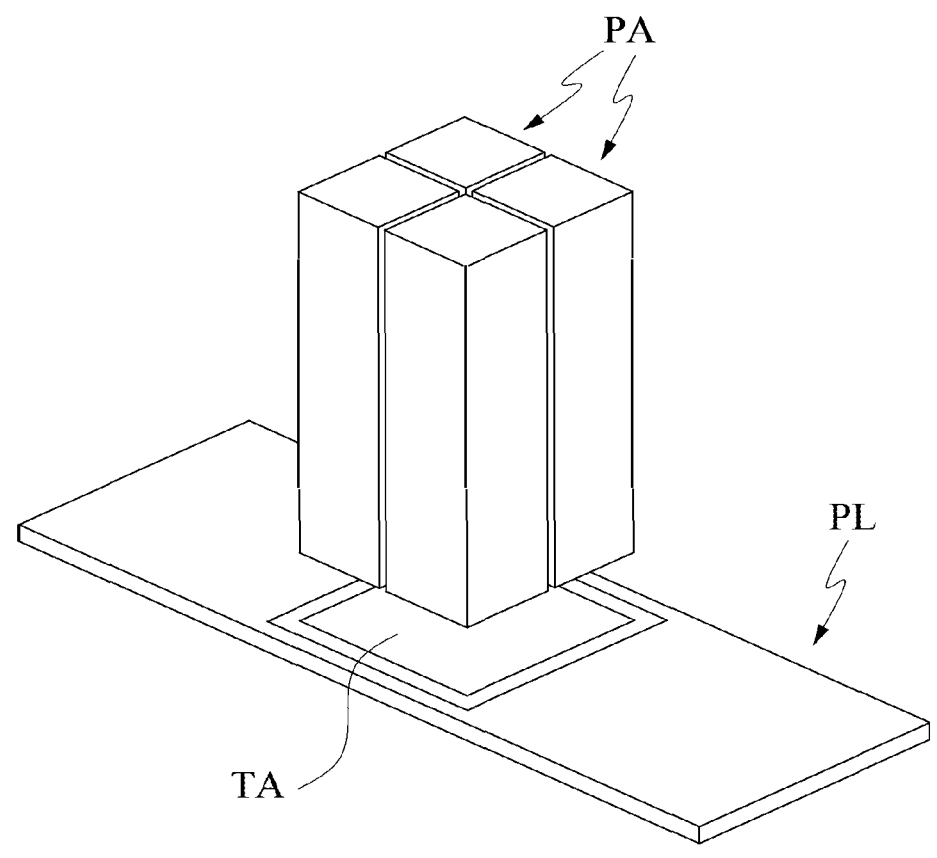
FIG. 33 illustrates an implementation of a plurality of patches as an embodiment of a patch according to the present application.

FIG. 33 illustrates a case in which the plurality of patches PA are used together as an embodiment of the patch PA according to the present application. According to FIG. 33, the plurality of patches PA according to an embodiment of the present application may simultaneously come into contact with a target region TA placed on a plate PL. The patches PA constituting the plurality of patches PA may have a standardized form. The plurality of patches PA may include a first patch and a second patch, and a substance contained in the first patch may be different from a substance contained in the second patch.

Figure 34:
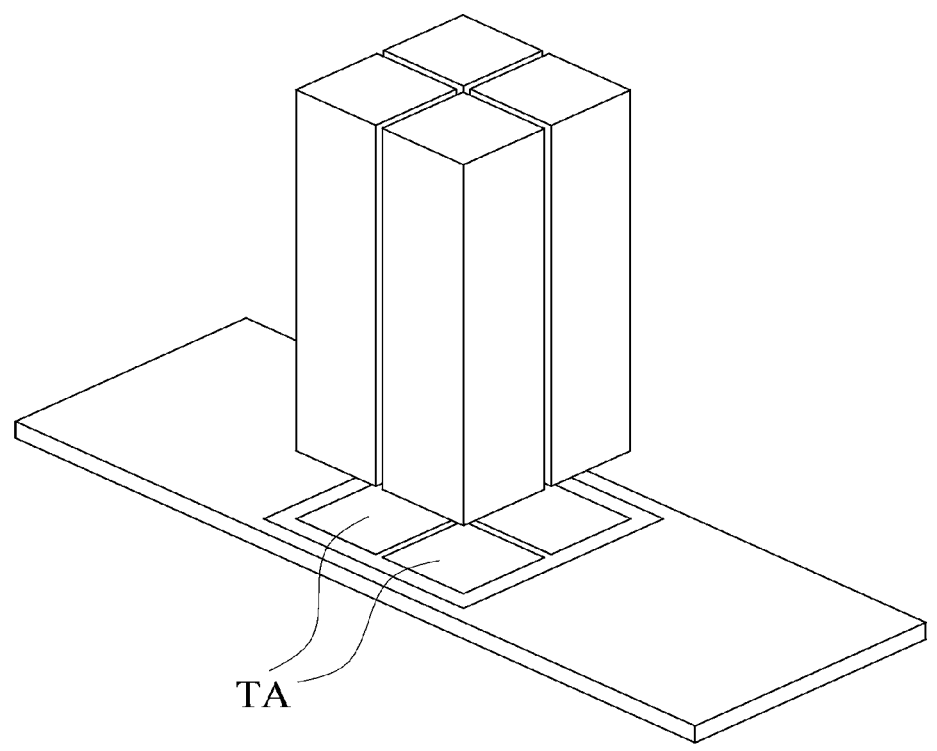
FIG. 34 illustrates an implementation of a plurality of patches and a plate having a plurality of target regions as an embodiment of a patch according to the present application.

FIG. 34 illustrates a case in which the plurality of patches PA are used and the plate PL includes a plurality of target regions TA. According to FIG. 34, the plurality of patches PA according to an embodiment of the present application may simultaneously come into contact with the plurality of target regions TA placed on the plate PL. The plurality of patches PA may include a first patch PA and a second patch PA, the plurality of target regions TA may include a first target region and a second target region, and the first patch may come into contact with the first target region and the second patch may come into contact with the second target region.

3.3.2 Fifth Embodiment

The plurality of patches PA may perform a plurality of functions. As described above, the patches PA may simultaneously perform a plurality of functions, and the patches PA may also simultaneously perform different functions. However, embodiments are not limited to the above, and the functions may also be combined and performed in the plurality of patches PA.

First, in the case in which the patches PA simultaneously perform the plurality of functions, the patches PA may perform both containing and release of a substance. For example, the patches PA may contain different substances and release substances contained in the target regions TA. In this case, the contained substances may be simultaneously or sequentially released.

Next, in the case in which the patches PA simultaneously perform different functions, the patches PA may separately perform containing and release of a substance. In this case, only some of the patches PA may come into contact with a target region TA and release a substance to the target region TA.

3.3.3 Sixth Embodiment

When a plurality of patches PA are used, as described above, the plurality of patches PA may perform a plurality of functions. First, the patches PA may simultaneously perform containing, releasing, and absorbing of substances. Alternatively, the patches PA may also separately perform the containing, releasing, and absorbing of the substances. However, embodiments are not limited thereto, and the functions may also be combined and performed in the plurality of patches PA.

For example, at least some of the plurality of patches PA may contain a substance and release the contained substance to the target region TA. In this case, at least a remainder of the plurality of patches PA may absorb a substance from the target region TA. Some of the plurality of patches PA may release a substance that binds specifically to a substance placed in the target region TA. In this case, specific binding may be detected by absorption of a substance that has not formed specific binding from the substance placed in the target region TA using another patch PA.

3.3.4 Seventh Embodiment

When a plurality of patches PA are used, the patches PA may simultaneously perform containing and release of a substance and providing of an environment. Alternatively, the patches PA may separately perform the containing and release of a substance and providing of an environment. However, embodiments are not limited thereto, and the functions may also be performed in combination in the plurality of patches PA.

For example, a patch PA among the plurality of patches PA may release a substance contained therein to the target region TA. In this case, another patch PA may provide an environment to the target region TA. Here, the providing of an environment may be implemented in the form in which an environmental condition of a substance contained in the other patch PA is provided to the target region TA. More specifically, a reacting substance may be provided to the target region TA by the patch PA, and the other patch PA may come into contact with the target region TA and provide a buffering environment.

As another example, the plurality of patches PA may be in contact with each other. In this case, at least one patch PA may contain a substance and release the substance contained therein to another patch PA configured to provide an environment. In the present embodiment, the patch PA configured to provide an environment may release a substance, come into contact with at least one other patch PA that is not in contact with the patch PA configured to provide an environment, and absorb a substance from the patch PA.

4. Blood Test (Hematologic Diagnosis)

4.1 Meaning

The patch of the present application may be used in a blood test. Blood test refers to an examination for blood in accordance with a hematologic technique for diagnosing a testee's health condition, presence of illness or disease, progress thereof and the like.

The patch of the present application may be used in various blood testing methods of obtaining numerical and morphological information of blood. Hereinafter, a few typical blood tests using the patch of the present application will be mentioned. However, it should be noted that the blood test is not limited to the examples which will be described below in the present application.

In applying the patch of the present application to a blood test, the above-described base substance BS and the additive substance AS may be properly changed in accordance with a site to which the patch is applied.

4.2 Typical Examples of Blood Test

4.2.1 Complete Blood Cell Count (CBC)

A typical example of a blood test may include a CBC (Complete Blood cell Count).

The CBC is one of the most fundamental blood tests that uses numerical information or morphological information on blood cells, i.e., red blood cells, white blood cells, and platelets and has various clinical indications including diagnosis, treatment, and monitoring of a disease.

4.2.2 Peripheral Blood Smear Examination

Another typical example of a blood test may include a peripheral blood smear examination. The peripheral blood smear examination is an examination in which collected blood is smeared on a slide glass and then stained to examine numerical or morphological information of blood cells or discover bacteria or parasites in blood through a microscope. For example, red blood cells may be used in distinguishing anemia and determining a cause thereof, and white blood cells may be helpful in determining myelodysplastic syndrome, leukemia, a cause of infection or inflammation, and megaloblastic anemia. Also, platelets are helpful in determining a myeloproliferative disorder, platelet satellitism, and the like. In addition, platelets may also be used for detecting bacterial pathogens such as tubercule bacillus or various parasites including bacteria present in blood.

4.3 Examples of Staining Techniques

In the present application, a blood test may be performed mostly by smearing blood on a plate PL such as a slide glass, staining the blood, and then observing the stained blood.

Here, various staining techniques may be used as necessary. For example, Romanowsky staining techniques such as a Giemsa staining technique, a Wright staining technique, and a Giemsa-Wright staining technique may be used in staining blood. In addition, staining techniques such as a simple staining technique, a Gram staining technique, or an AFB [Ziehl-Neelsen] staining technique accompanied by a bacteriological examination, and a Papanicolaou staining technique mostly used in cervical cancer examination may be used in a blood test of the present application.

4.4 Performance of Blood Test

4.4.1 Preparation of Sample

Here, preparation of a sample used in a blood test, i.e., blood, will be described.

A sample may be prepared on a plate PL to examine for blood using the patch PA of the present application.

Here, the plate PL may refer to a solid plate such as a general slide glass and a plate manufactured with polystyrene, polypropylene, or the like. A plate having a different form of bottom or different transparency may be used as the plate PL in accordance with a detection method. The plate PL may include a reaction region that may come into contact with the patch PA or in which a desired reaction may occur.

4.4.2 Preparation of Patch

In performing a blood test in the present application, the above-described patch PA may be used.

The patch PA may contain a staining reagent and deliver the staining reagent to the plate PL. Here, the staining reagent may be changed in various ways in accordance with a purpose of a blood test or a staining technique for performing the blood test. Typical examples of a staining reagent include staining solutions which are used in Romanowsky staining techniques such as acetocarmine, methylene blue, eosin, acid fuchsin, safranin, Janus Green B, hematoxylin, Giemsa solution, Wright solution, and Wright-Giemsa solution, Leishman staining solution, Gram staining solution, carbol-fuchsin, and Ziehl-Neelsen solution. Of course, the staining reagent in the present disclosure is not limited to the above-mentioned examples, and various other substances for staining blood may also be used as a staining reagent as necessary.

Only a single staining reagent may be contained in the patch PA. For example, when attempting to perform a staining technique using only one type of staining reagent such as the simple staining technique, the patch PA may contain only one type of staining reagent among methylene blue, crystal violet, safranin, etc. which are used in the simple staining technique.

Here, two or more staining reagents may also be contained together in the patch PA. For example, when attempting to perform a staining technique using two or more staining reagents together such as the Giemsa staining technique, two staining reagents such as eosin, which stains cytoplasm red, and methylene blue, which stains a nucleus violet, may be simultaneously contained in the patch PA.

Of course, even when attempting to perform a staining technique in which two or more staining reagents are used together, it is not always necessary for the patch PA to contain all staining reagents used in the staining technique as described above. That is, the patch PA may contain only some of a plurality of staining reagents used in a staining technique. For example, the Giemsa staining technique may also be performed by simultaneously using a patch PA that only contains eosin as a single staining reagent and a patch PA that only contains methylene blue or azure blue as a single reagent.

In addition to including substances for directly staining cells as staining reagents, the patch PA may also include substances for decolorizing or mordanting. For example, when attempting to perform the Gram staining technique, a patch PA that contains crystal violet, which is a main staining agent, a patch PA that contains safranin, which is a contrast staining agent, a patch PA that contains iodine, which is a mordanting agent, and a patch PA that contains alcohol, which is a decolorizing agent, may be prepared.

The patch PA may contain a fixing solution and fix smeared blood on the plate PL. Alcohol such as methanol or ethanol or formaldehyde may be used as the fixing solution.

When a substance contained in the patch PA is hydrophobic, the patch PA may also be prepared to have hydrophilic property. For example, this applies to a patch PA including alcohol, which is a fixing solution or a decolorizing agent. A polydimethylsiloxane (PDMS) gel, a polymethylmethacrylate (PMMA) gel, a silicone gel, or the like may be used as a material of the hydrophobic patch PA.

Alternatively, in a patch PA that contains a fixing agent or a decolorizing agent, the fixing agent or the decolorizing agent may be replaced with a solid substance which is a solidified substance of the fixing agent or the decolorizing agent. An example thereof may include solidified methanol or the like.

The patch PA may contain a washing solution and absorb residue from the plate PL. By the patch PA containing the washing solution and being brought into contact with the patch PA and then separated therefrom, the patch PA may absorb and remove impurities or the like from the plate PL. The washing solution used above may be a tris buffered saline (TBS) or phosphate buffered saline (PBS) with Tween 20.

The patch PA may contain a buffer solution and provide an environment for the plate PL. In this case, the buffer solution may facilitate each step of the blood test performed properly. Therefore, a buffer solution used in each step may contain different components. A solution having an optimal pH for each staining technique may be used as the buffer solution.

The above-described patches PA may be separately used or used in combination. For example, the patch PA may contain a staining reagent and a buffer solution together.

The performance of the blood test using the patch PA will be described in detail below.

4.4.3 Blood Testing Method

Here, a few typical examples of a method of performing a blood test using the above-described patch PA and plate PL of the present application will be described.

However, the blood testing method of the present disclosure is not limited to examples which will be described below, and since a plurality of modified detection methods may be present, the methods may be applied throughout the blood testing method performed using the patch PA.

A blood test may be performed using the patch PA and the plate PL of the present application.

The blood test using the patch PA and the plate PL may be performed by smearing a sample placed on the plate PL, bringing the patch PA into contact with the smeared sample to stain the sample, and detecting a staining result.

4.4.3.1 Smearing of Blood

Smearing of blood on the plate PL may be performed through various methods. Here, blood may be smeared in a monolayer or in a multi-layer as necessary.

Figure 35:
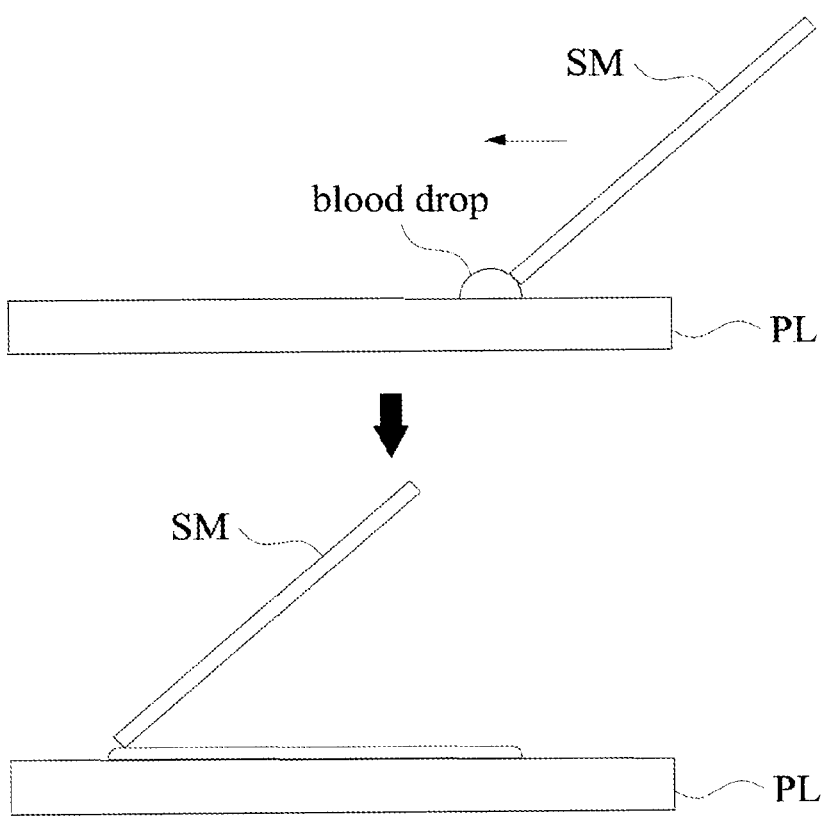
FIGS. 35 and 36 are views illustrating an example of a blood smear method according to an embodiment of the present disclosure.
Figure 36:
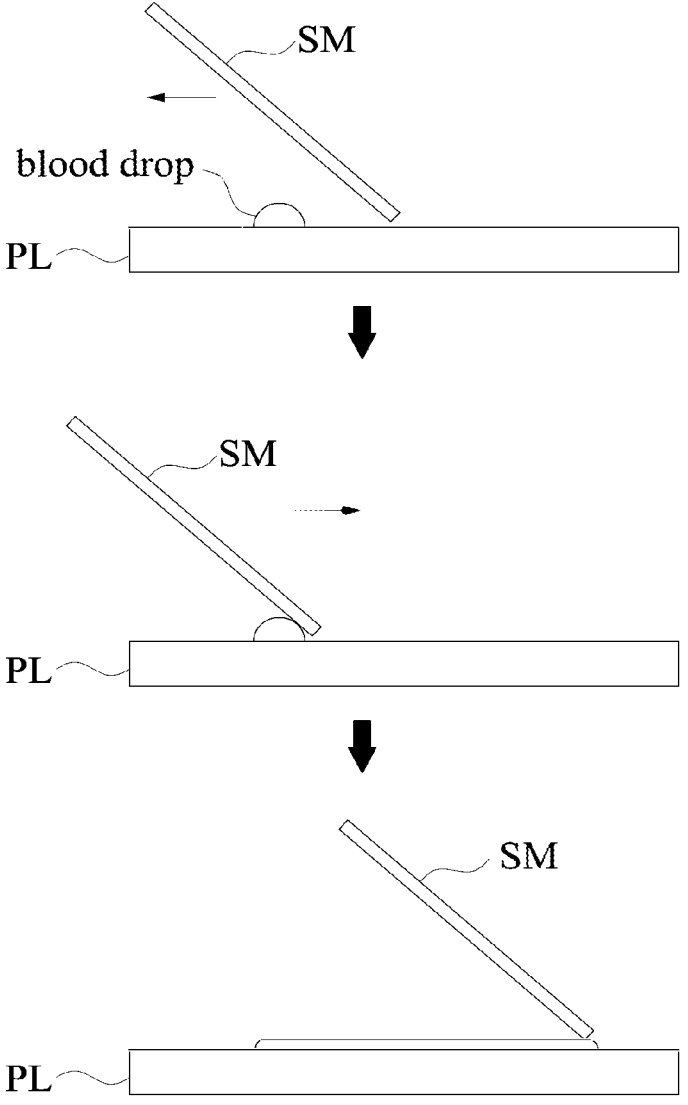

FIGS. 35 and 36 are views related to an example of a blood smearing method according to an embodiment of the present disclosure.

According to an example, smearing a sample on a plate PL may include dropping a blood drop on the plate PL and then smearing blood on the plate PL using a smearing member (another slide glass, a smearing film, or the like).

Referring to FIG. 35, by sliding a smearing member SM in one direction passing through the blood drop dropped on the slide glass, blood may be smeared on the slide glass. In this case, blood may be spread on the slide glass as a result of being physically pushed by the smearing member.

Alternatively, referring to FIG. 36, blood may be smeared on a slide glass by sliding the smearing member SM in one direction up to a point at which the smearing member SM is in contact with the blood drop dropped on the slide glass and then sliding the smearing member SM in the opposite direction. In this case, due to the capillary action that occurs between the smearing member and the slide glass, blood may be spread on the slide glass by following the smearing member in the opposite direction.

Figure 37:
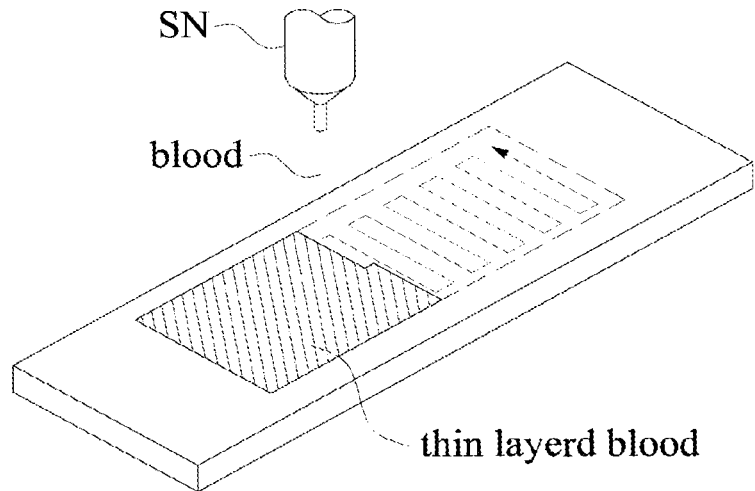
FIG. 37 is a view illustrating another example of a blood smear method according to an embodiment of the present disclosure.

FIG. 37 is a view related to another example of a blood smearing method according to an embodiment of the present disclosure.

According to another example, smearing a sample on a plate PL may include smearing blood on the plate PL by moving a smearing nozzle configured to spray blood in a monolayer on the plate PL. Here, the smearing nozzle may spray inserted blood in a monolayer using a micro-fluidic channel.

Referring to FIG. 37, by a smearing nozzle SN spraying blood while moving along a predetermined path on a slide glass, blood may be smeared on the slide glass.

4.4.3.2 Staining of Blood

Staining of blood may be performed by bringing a patch PA including a staining reagent in contact with blood smeared on a plate PL. When the smeared blood and the patch PA are brought into contact, the staining reagent included in the patch PA may move to the blood and stain a granule present inside a cytoplasm, a nucleus, a white blood cell, or the like in blood.

A patch PA that includes a nucleus staining reagent may stain a nucleus in blood. A basic staining reagent is mostly used as a nucleus staining reagent, and typical examples of the basic staining reagent include methylene blue, toluidine blue, and hematoxylin. Since the basic staining reagent is negatively charged, when the patch PA comes into contact with blood, the basic staining reagent may move from the patch PA to blood and be bound to a positively-charged nucleus in the blood to stain the nucleus.

A patch PA that includes a cytoplasm staining reagent may stain a cytoplasm or an extracellular structure in blood. An acidic staining reagent is mostly used as a cytoplasm staining reagent, and typical examples of the acidic staining reagent include eosin, acid fuchsin, and orange G. Since the acidic staining reagent is positively charged, when the patch PA comes into contact with blood, the acidic staining reagent may move from the patch PA to blood and be bound to a negatively charged cytoplasm or extracellular portion in the blood to stain the cytoplasm or the extracellular portion.

A granule may be stained with appropriate color by a basic staining reagent and an acidic staining reagent. For example, a granule may be stained violet by methylene blue and eosin.

Of course, blood staining is not always necessarily performed using the above-described staining reagents.

For example, the patch PA may contain a neutral staining reagent that simultaneously includes a positively-charged portion and a negatively-charged portion. When the patch PA that contains the neutral staining reagent comes into contact with blood, the negatively-charged portion of the staining reagent may be bound to a positively-charged portion (e.g., a cytoplasm) in blood and stain the positively-charged portion with a predetermined color, and the positively-charged portion of the staining reagent may be bound to a negatively-charged portion (e.g., a nuclei) in blood and stain the negatively-charged portion with a color that is different from the predetermined color. A typical example of a neutral staining reagent may include a Wright staining reagent.

In the above description, staining process for color developing of an actual staining target has been mainly described, unlike this, a fluorescent substance that allows a staining target to be fluorescent color developed may also be used in place of a staining reagent. For example, when attempting to observe a nucleus, a nucleus may be allowed to develop fluorescent color by a method of adding a fluorescent substance to a substance bound to the nucleus.

4.4.3.3 Examination for Blood

An examination for blood may be performed by acquiring an image related to stained blood and analyzing the acquired image.

Here, the image acquisition may be performed using an optical device. Any device capable of acquiring an image of stained blood in a magnification appropriate for detecting blood cells such as red blood cells, white blood cells, or platelets stained in blood or pathogens such as bacteria in blood may be used as the optical device. For example, an optical device may include an optical sensor configured with a charge-coupled device (CCD) or a complementary metal-oxide semiconductor (CMOS), a lens barrel configured to provide an optical path, a lens configured to adjust a magnification or a focal length, and a memory configured to store an image acquired by the CCD or CMOS.

Figure 38:
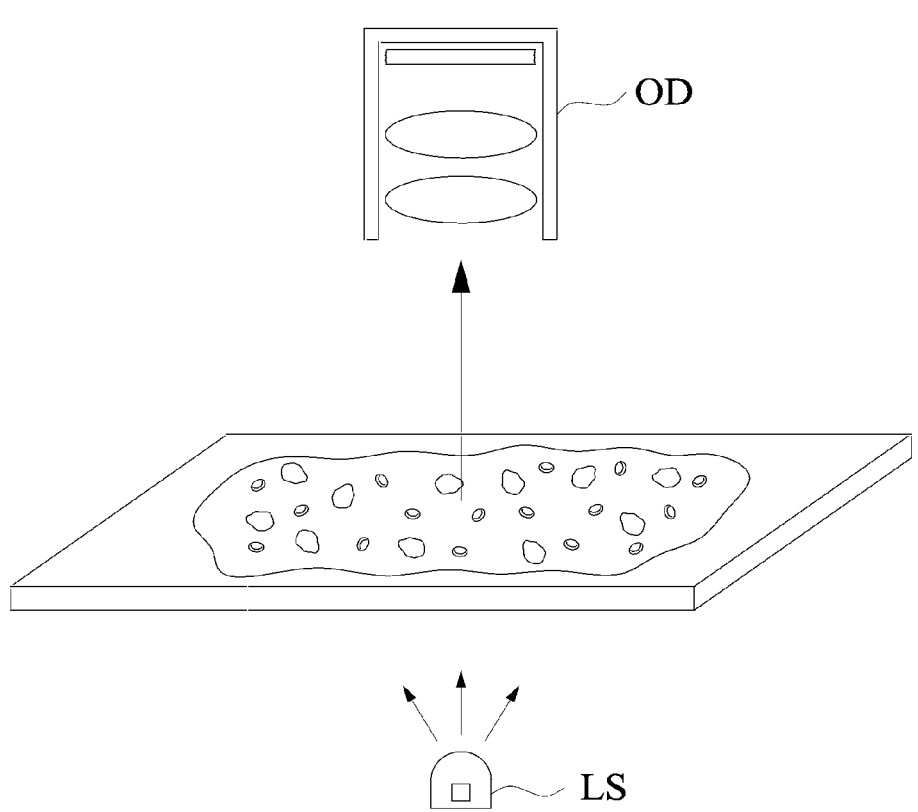
FIGS. 38 and 39 are views illustrating acquiring an image of stained blood according to an embodiment of the present disclosure.
Figure 39:
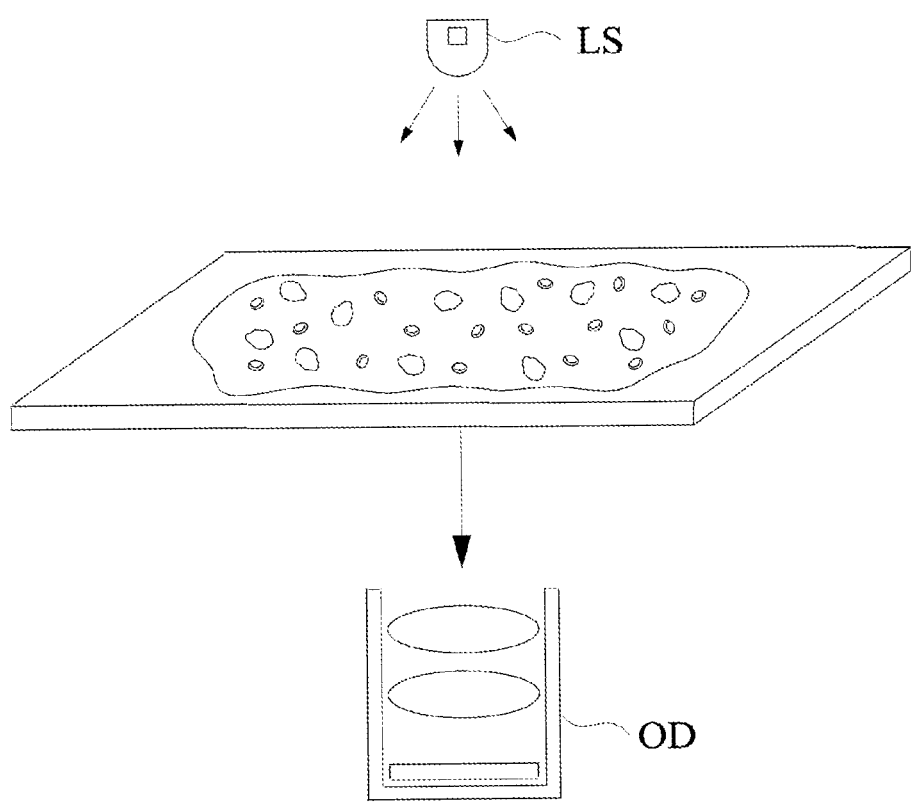

FIGS. 38 and 39 are views related to acquiring an image of stained blood according to an embodiment of the present disclosure.

Referring to FIGS. 38 and 39, an optical device OD may directly acquire an image while blood stained using the patch PA is smeared on a plate PL. Here, the optical device OD may receive light that has been irradiated from a light source LS and passed through the plate PL on which the stained blood is smeared and acquire an image of the stained blood.

As an example, referring to FIG. 38, the optical device OD may be disposed on a surface of a slide glass on which blood is smeared (hereinafter referred to as a "front surface"), and the light source LS may be disposed at a surface opposite the front surface, i.e., a rear surface, of the slide glass. Due to such an arrangement, the optical device OD may receive light that has been irradiated from the light source LS at the rear side of the slide glass and has passed through the slide glass, and acquire an image of the stained blood.

As another example, referring to FIG. 39, the optical device OD may be disposed on a rear surface of the slide glass, and the light source LS may be disposed on a front surface of the slide glass. Due to such arrangement, the optical device OD may receive light that has been irradiated from the light source LS at the front side of the slide glass and has passed through the slide glass, and acquire an image of the stained blood.

Here, preferably, the plate PL may be prepared with a material through which light output from the light source transmitted easily as possible. The light source may output white light or a wavelength in a specific wavelength band.

However, when an image needs to be checked with a high magnification, it may be preferable to perform observation without light being transmitted through the plate PL or the patch PA.

A blood test may be performed by acquiring various pieces of information from an acquired image.

As an example, the image may be provided to a tester through a computer or a monitor of medical equipment. The tester may identify the number of blood cells, the morphology of the blood cells, a presence of bacteria, the number, morphology, or the like of the bacteria, and determine a testee's health condition or a state of a disease on the basis of the identified results.

As another example, an electronic device in which an image analysis program is installed may acquire an image from an optical device, and pieces of information on the number or the morphology of blood cells or a presence, the number, or the morphology of bacteria may be generated from the image. The generated information may be provided to the tester through the computer or the monitor of the medical equipment. The tester may determine the testee's health condition or state of the disease on the basis of the received pieces of information.

As yet another example, the information generated by the electronic device in which an image analysis program is installed may be provided to an electronic device in which a blood test program is installed, and the electronic device in which the blood test program is installed may determine the testee's health condition or state of disease on the basis of the pieces of provided information. Here, a single electronic device in which both an image analysis program and a blood test program are installed may also perform both an image analysis operation and a blood test operation.

The image analysis program may analyze an acquired image. Specifically, the image analysis program may acquire numerical information and morphological information of blood cells or bacteria in blood from an acquired image.

The image analysis program may determine a type of blood cells from the acquired image. The types of blood cells include white blood cells, red blood cells, or platelets, and more specifically, may also include types of white blood cells. The image analysis program may also determine whether blood cells are abnormal.

Here, the image analysis program may determine the type or abnormality of the blood on the basis of the size or morphology of blood cells in the image.

The image analysis program may determine a presence of bacteria in blood. The image analysis program may count the number of different types of blood cells, the number of abnormal blood cells, or the number of bacteria.

The blood test program may determine the testee's health condition, presence of a disease, progress of disease or the like on the basis of numerical information related to blood cells or bacteria (for example, the number of each type of blood cells, the number of abnormal blood cells, the number of bacteria, or the like) and morphological information (the morphology of blood cells or the morphology of bacteria).

At least one of the above-described image analysis program and blood test program may perform the above-described determination process in accordance with a preset algorithm or in accordance with an algorithm formed through mechanical learning such as deep learning.

4.5 Embodiments of Blood Test

Figure 40:
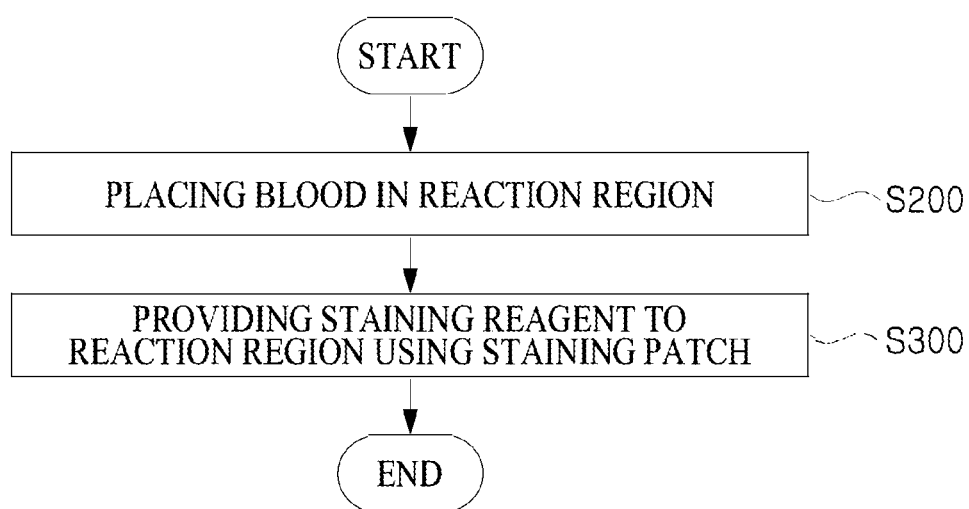
FIG. 40 illustrates a flowchart for describing an example of a blood testing method according to the present application.

FIG. 40 illustrates a flowchart for describing an example of a blood testing method according to the present application.

The blood testing method according to an embodiment of the present application may include placing blood, which is a target to be tested, in a reaction region (S200), and using a patch PA that contains a staining reagent for staining the blood and providing the staining reagent to the reaction region (S300).

The placing of the blood, which is the target to be tested (S200) may be performed by the above-described method of smearing a sample on the plate PL.

Figure 41:
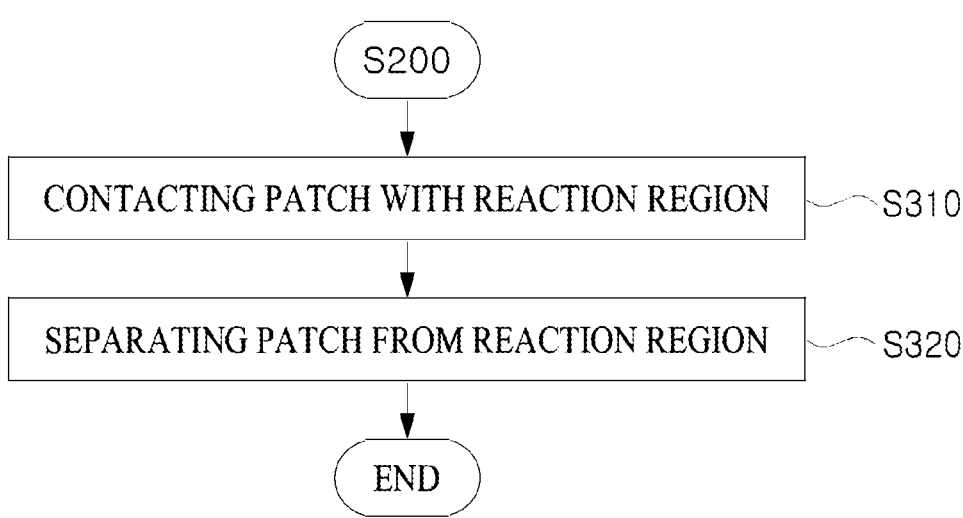
FIG. 41 illustrates a flowchart for describing an example of providing a staining reagent to a reaction region in the blood testing method according to an embodiment of the present application.

FIG. 41 illustrates a flowchart for describing an example of the providing of the staining reagent to the reaction region in the blood testing method according to an embodiment of the present application.

Referring to FIG. 41, the providing of the staining reagent to the reaction region (S300) may include contacting the patch with the reaction region so that the staining reagent is movable to the reaction region (S310) and separating the patch PA from the reaction region.

When the patch PA containing the staining reagent comes into contact with blood (S310), the staining reagent in the patch PA may move to the reaction region and stain the blood. For example, when a patch PA that contains a basic staining reagent comes into contact with blood, the basic staining reagent may move to the reaction region and stain a nucleus of white blood cells from among blood cells or a nucleus of bacteria present in blood. As another example, when a patch PA that contains an acidic staining reagent comes into contact with blood, the acidic staining reagent may move to the reaction region and stain a cytoplasm or an extracellular structure of blood cells or bacteria.

The patch PA is separated from the reaction region (S320). When a duration for maintaining a contact between the patch PA and the reaction region is extremely short, it is difficult to perform sufficient staining. Conversely, when a duration for maintaining the contact is extremely long, not only the time taken for the overall blood test is increased, an excessive amount of staining reagent may be moved to blood and staining quality may be degraded. Therefore, the patch PA is separated from a contact region after a certain amount of time passes after the patch PA has been moved to the reaction region. The duration for maintaining a contact may be properly set in consideration of a concentration of the staining reagent of the patch PA, a density of the gel-type structure, and external conditions such as a temperature condition.

Figure 42:
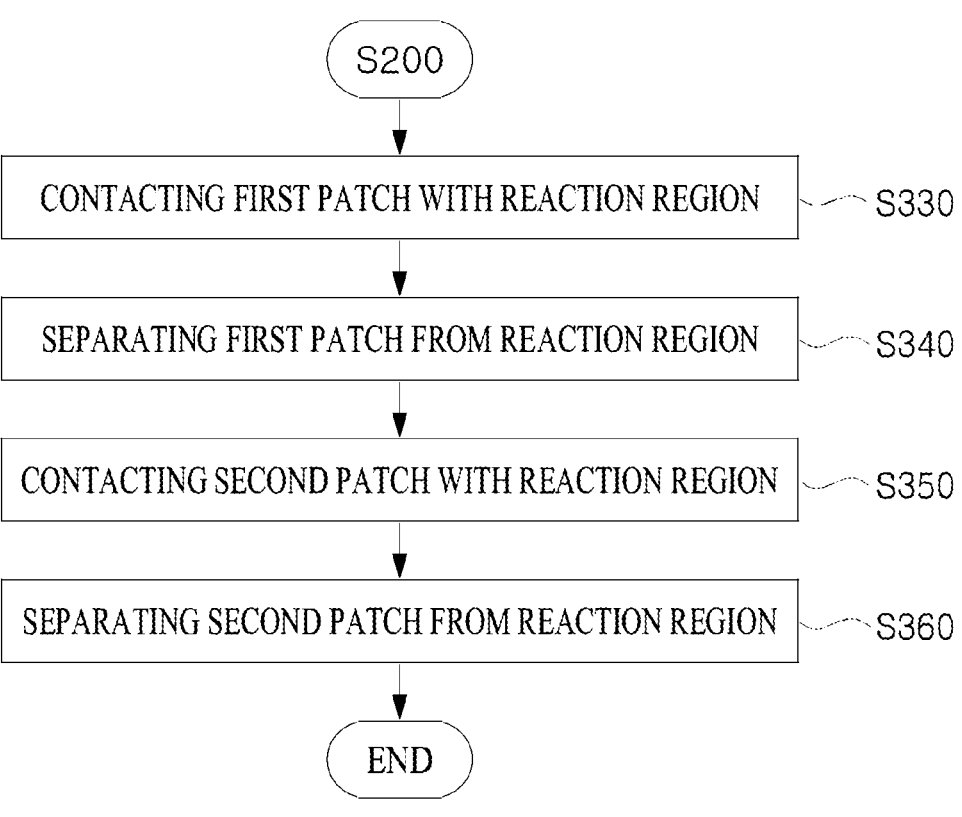
FIG. 42 illustrates a flowchart for describing another example of providing a staining reagent to a reaction region in the blood testing method according to an embodiment of the present application.

FIG. 42 illustrates a flowchart for describing another example of the providing of the staining reagent to the reaction region in the blood testing method according to an embodiment of the present application.

Referring to FIG. 42, the providing of the staining reagent to the reaction region (S300) may include contacting a first patch PA with the reaction region so that a first staining reagent is movable to the reaction region (S330), separating the first patch PA from the reaction region (S340), contacting a second patch PA with the reaction region so that a second staining reagent is movable to the reaction region (S350), and separating the first patch PA from the reaction region (S360).

Here, the first patch PA and the second patch PA are patches PA that respectively contain the first staining reagent and the second staining reagent for staining different components of blood. For example, the first staining reagent may be any one of a basic staining reagent and an acidic reagent, and the second staining reagent may be the other one of the basic staining reagent and the acidic staining reagent. Accordingly, one of the first patch PA and the second staining patch PA may stain a cytoplasm or extracellular structure of blood cells or a cytoplasm or extracellular structure of bacteria in blood, and the other one may stain a nucleus of blood cells or a nucleus of bacteria in blood.

When three or more staining reagents (for example, a main staining agent, a contrast staining agent, a mordanting agent, and the like) are required to be used in staining blood, as many staining patches PA may be added as needed, and the contacting of a staining patch with the reaction region and the separating of the staining patch from the reaction region may be performed for each added staining patch PA.

Figure 43:
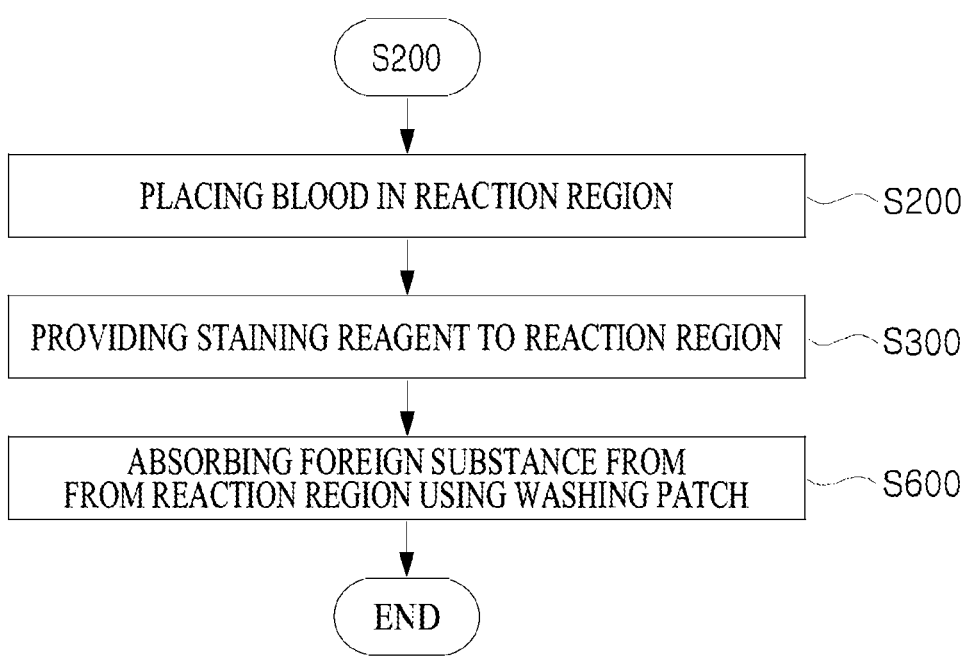
FIG. 43 illustrates a flowchart for describing another example of a blood testing method according to the present application.

FIG. 43 illustrates a flowchart for describing another example of a blood testing method according to the present application.

Referring to FIG. 43, the blood testing method may further include absorbing a foreign substance from the reaction region using a washing patch PA to (S600), in addition to the placing of the sample (S200) and the providing of the staining reagent to the reaction region (S300). Here, the washing patch PA may be a patch PA that contains a washing solution.

Figure 44:
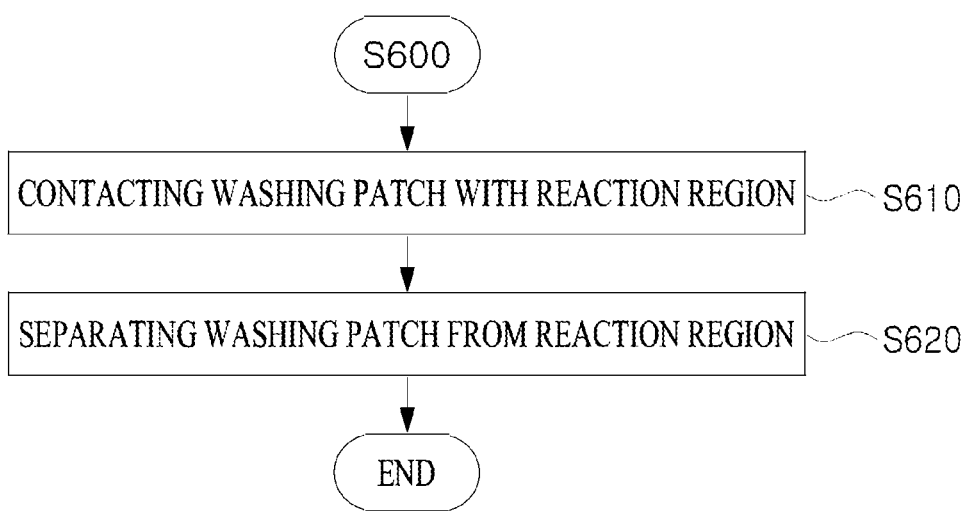
FIG. 44 illustrates a flowchart for describing an example of removing a foreign substance from a reaction region in the blood testing method according to the embodiment of the present application.

FIG. 44 illustrates a flowchart for describing an example of the removing of the foreign substance from the reaction region in the blood testing method according to another embodiment of the present application.

Referring to FIG. 44, the absorbing of the foreign substance from the reaction region using the washing patch PA (S600) may include contacting the patch PA with the reaction region so that the foreign substance is movable from the reaction region to the washing patch PA (S610) and separating the patch PA from the reaction region (S620).

When the patch PA that contains the washing solution comes into contact with blood (S610), the foreign substance remaining in the reaction region may be absorbed into the patch PA during the staining process. Then, when the washing patch PA is separated from the reaction region (S620), the patch PA may absorb a foreign substance in the water film WF while absorbing a water film formed between the plate PL and the patch PA.

Figure 45:
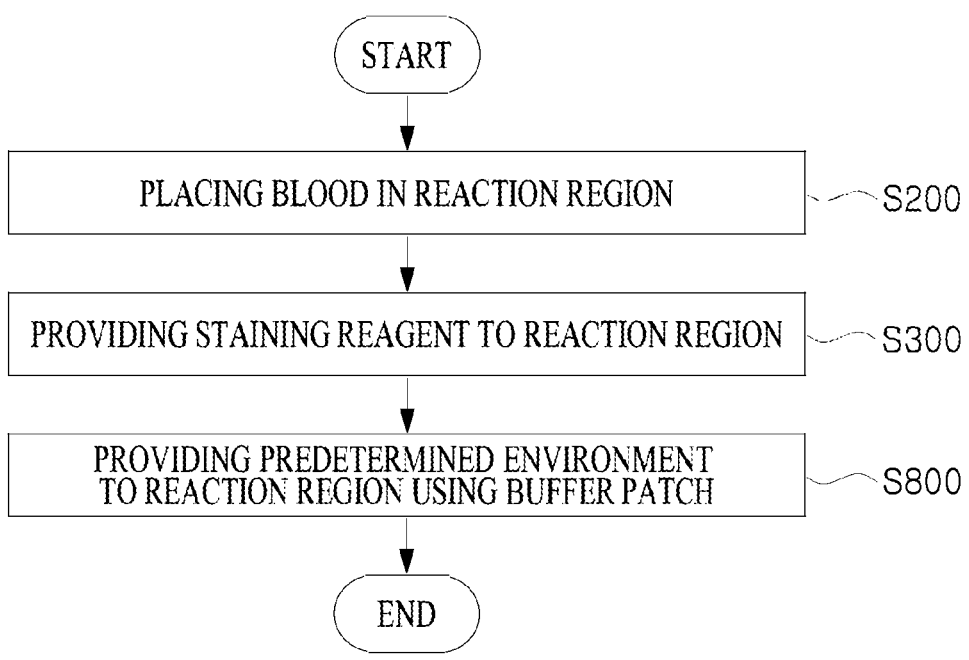
FIG. 45 illustrates a flowchart for describing yet another example of a blood testing method according to the present application.

FIG. 45 illustrates a flowchart for describing yet another example of a blood testing method according to the present application.

Referring to FIG. 45, the blood testing method may further include providing a predetermined environment to the reaction region using buffer patch PA and (S800), in addition to the placing of the sample (S200) and the providing of the staining reagent to the reaction region (S300). Here, the buffer patch PA may be a patch PA that contains a buffer solution.

Figure 46:
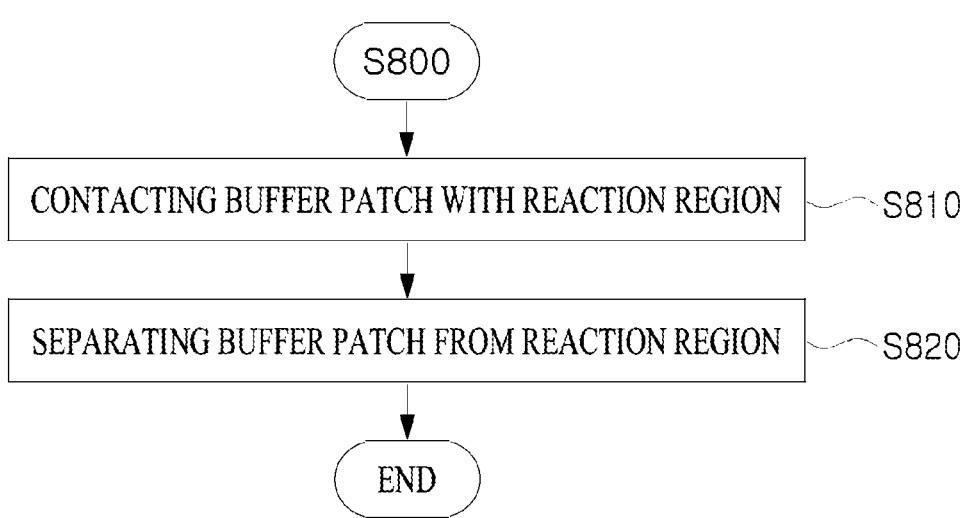
FIG. 46 illustrates a flowchart for describing an example of providing a predetermined environment to a reaction region in the blood testing method according to another embodiment of the present application.

FIG. 46 illustrates a flowchart for describing an example of the providing of the predetermined environment to the reaction region in the blood testing method according to another embodiment of the present application.

Referring to FIG. 46, the providing of the predetermined environment to the reaction region using the buffer patch PA (S800) may include contacting the buffer patch PA with the reaction region so that the predetermined environment is provided to the reaction region (S810) and separating the buffer patch PA from the reaction region (S820).

When the patch PA containing the buffer solution comes into contact with the reaction region (S810), a predetermined condition required for the staining reagent to stain blood may be made in the reaction region. For example, when the buffer patch PA comes into contact with the reaction region, acidity of the water film WF between the buffer patch PA and the plate PL may reach an optimal pH for staining due to the buffer solution, and accordingly, staining quality may be improved. When an excessive amount of staining reagent is moved from the staining patch PA to blood and blood cells or bacteria are overstained, or when blood is stained with two or more staining reagents using a first staining patch PA and a second staining patch PA in order to use a plurality of staining reagents, the buffer patch PA may create an appropriate environment for staining in the reaction region, and staining quality may be improved.

When the buffer patch PA is separated from the reaction region (S820), the water film WF may be absorbed into the buffer patch PA, and a remaining staining reagent that has not been bound to blood may be absorbed into the buffer patch PA together with the water film WF. Accordingly, even when an excessive amount of staining reagent is applied into blood, degradation of staining quality may be prevented when the buffer patch PA is brought into contact with the reaction region and then separated therefrom.

Figure 47:
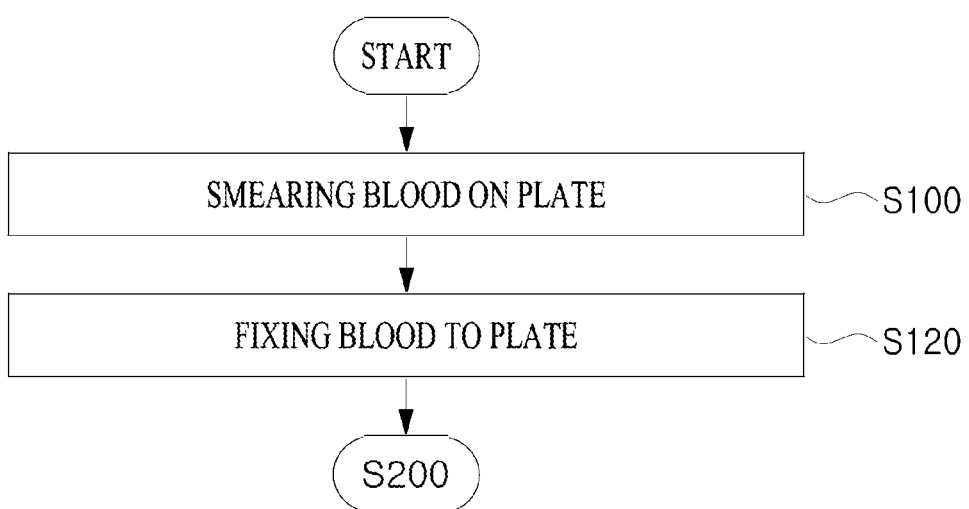
FIG. 47 illustrates a flowchart for describing still another example of a blood testing method according to the present application.

FIG. 47 illustrates a flowchart for describing still another example of a blood testing method according to the present application.

Referring to FIG. 47, a method of performing a blood test of the present application may further include smearing blood on the plate PL (S100) and fixing the smeared blood (S120).

The applying of the blood on the plate PL (S100) may include smearing the blood in a monolayer or in a thin layer similar to the monolayer.

When diagnosis is performed with the blood which is smeared in the shape similar to the monolayer, as described above, an effective surface area between the blood smeared on the plate PL and the patches PA coming into contact with the plate PL may be maximized. In other words, by smearing blood and contacting the patch PA with the blood so that a target is detected, an effective result may be acquired even with a small amount of blood. The reaction region may be very simply implemented in comparison to conventional blood testing methods in which a region in which blood is distributed is complexly designed for an expansion of the effective surface area and diagnosis is performed.

Further, when blood is smeared in a thin layer, there is an advantage in that qualitative analysis is possible when carrying out a disease examination or the CBC through image analysis.

The blood may also be smeared in a thick layer having a predetermined thickness instead of being smeared in a thin layer as necessary.

The fixing of the blood to the plate PL (S120) may include smearing the blood in a monolayer or in a thin layer similar to the monolayer and fixing the blood.

The absorbing of the foreign substance from the reaction region using the washing patch PA (S600) and the providing of the predetermined environment to the reaction region using the buffer patch PA (S800) described above may be performed during at least one time point of time points before and after the staining reagent is provided to the blood using the patch PA containing the staining reagent. However, it may be preferable to perform Step S600 or S800 after the providing of the staining reagent for the final staining quality to be improved.

When a plurality of patches PA that contain different staining reagents are brought into contact with blood and separated therefrom, each of Steps S600 and S800 may be performed during at least one time point of time points before the plurality of patches PA come into contact with blood, after the contact, and between time points during which the plurality of patches come into contact with blood.

However, it may be preferable to perform Steps S600 and S800 after the delivery of the staining regent for the final staining quality to be improved.

Since the buffer patch PA may also serve as the washing patch PA, Step S600 may also be performed using the buffer patch PA. Correspondingly, since the buffer patch PA performs a washing function as well as a buffering function upon coming into contact with blood, Step S800 may be performed together in a process in which Step S800 is performed by the buffer patch PA.

Likewise, since the washing patch PA may also serve as the buffer patch PA, Step S800 may also be performed using the washing patch PA. According to this, since the washing patch PA performs the buffering function as well as the washing function upon coming into contact with blood, Step S600 may be performed together in a process in which Step S600 is performed by the washing patch PA.

When the patch PA containing a staining reagent uses a buffer solution as a solvent, the patch PA containing the staining reagent may also serve as the buffer patch PA. According to this, since the staining patch PA performs the buffering function as well as the staining function upon coming into contact with blood, Step S800 may be performed together in a process in which Step S200 is performed by the staining patch PA.

When the patch PA containing the staining reagent uses a washing solution as a solvent, the patch PA containing the staining reagent may also serve as the washing patch PA. According to this, since the staining patch PA performs the washing function as well as the staining function upon coming into contact with blood, Step S600 may be performed together in a process in which Step S200 is performed by the staining patch PA.

When the patch PA containing the staining reagent uses the washing solution or the buffer solution as an internal solvent, the patch PA containing the staining reagent may also serve as the washing patch PA and the buffer patch PA. According to this, since the staining patch PA performs the washing function and the buffering function as well as the staining function upon coming into contact with blood, Steps S600 and S800 may be performed together in a process in which Step S200 is performed by the staining patch PA.

Hereinafter, a specific way of performing a blood test using the patch PA and the plate PL will be described using a few embodiments.

4.5.1 Reference Embodiment 1—Simple Stain

A blood test according to an embodiment of the present application may be performed by the simple staining technique using the plate PL and the patch PA.

Figure 48:
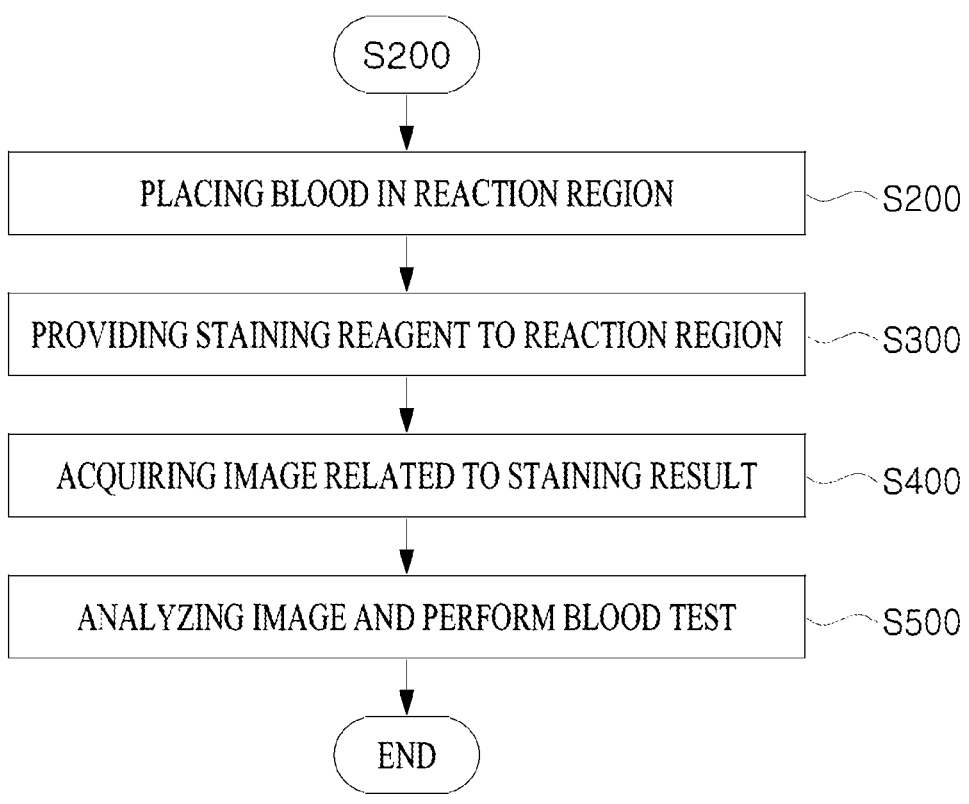
FIG. 48 illustrates a flowchart for describing a blood testing method using a simple stain as an example of a blood testing method according to the present application.

FIG. 48 illustrates a flowchart for describing a blood testing method by simple staining as an example of a blood testing method according to the present application.

The blood testing method by simple staining according to an embodiment of the present application may include placing blood in a reaction region (S200), providing staining reagent to the reaction region (S300), acquiring an image related to a staining result (S400), and analyzing the image and performing a blood test (S500).

The providing of the staining reagent (S300) in the blood test by simple staining includes providing a single staining reagent to blood. In the present embodiment, this may be performed mostly using a single staining patch that contains a single staining reagent.

The providing of the staining reagent (S300) may include first contacting a staining patch PA that contains the staining reagent with the reaction region on a plate PL such as a slide glass (S310) and separating the staining patch PA from the plate PL.

Figure 49:
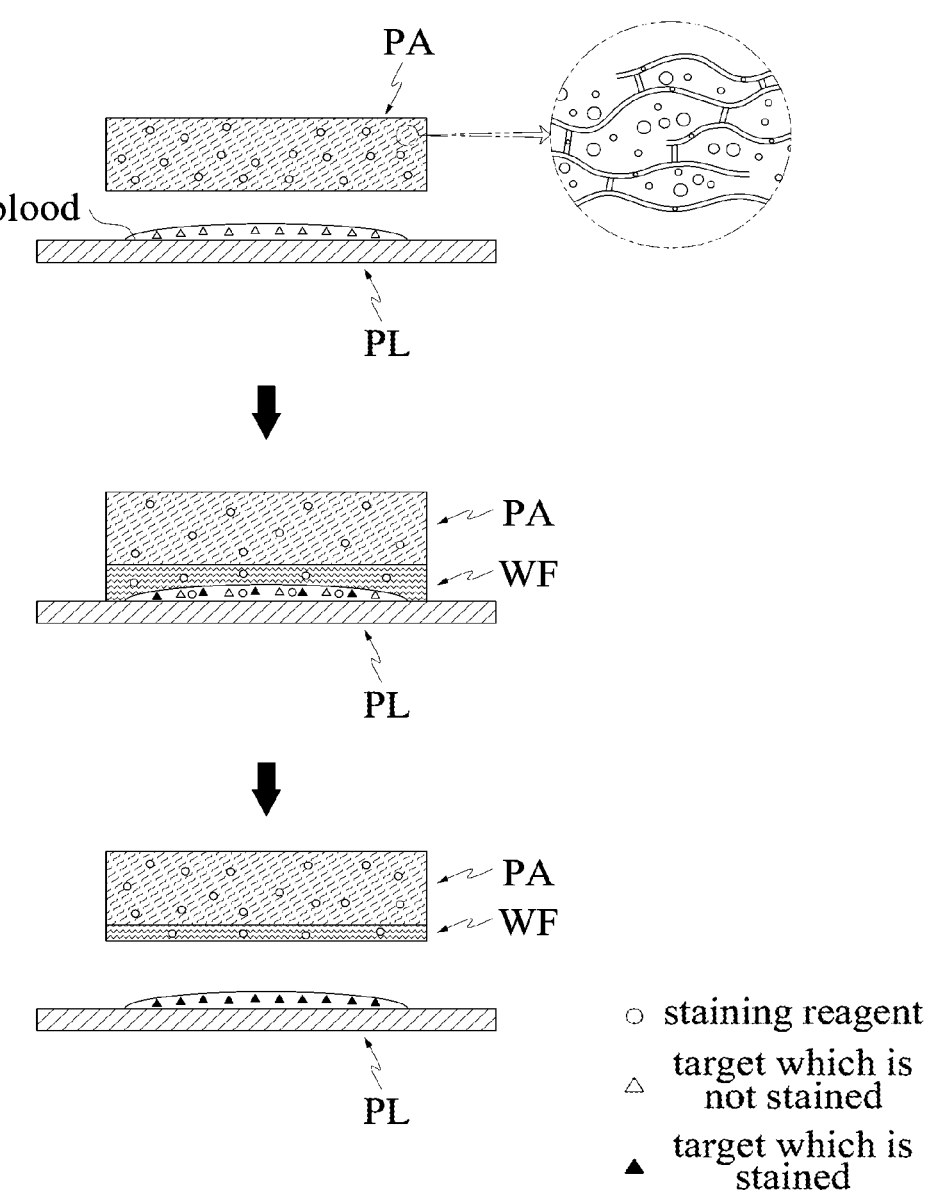
FIG. 49 is a view illustrating a process in which a staining reagent is provided in the blood testing method using a simple stain according to the present application.

FIG. 49 is a view illustrating a process in which a staining reagent is provided in the blood testing method by simple staining according to the present application.

Referring to FIG. 49, the staining patch PA may contain a staining reagent and provide the staining reagent to blood placed on the plate PL (S310). The providing of the staining reagent to the plate PL by the patch PA may be performed by the patch PA contacting with the plate PL so that the staining reagent is movable to the plate PL or the reaction region on the plate PL through a water film WF formed in the vicinity of a contact region.

The providing of the staining reagent to the plate PL may be due to a reaction between the staining reagent and the blood, particularly, a nucleus, a cytoplasm, an extracellular structure, and the like of blood cells or bacteria included in the blood. In other words, when the staining patch PA comes into contact with the reaction region, the staining reagent may be moved from the staining patch PA to the blood which is smeared and fixed in the reaction region, and the moved staining reagent may be bound to a target substance in blood and stain the target substance.

Here, when a buffer solution is used as a solvent in the staining patch PA, staining may be facilitated. Of course, a buffer patch may be used to implement a predetermined environment that is appropriate for a staining reaction.

When the staining reagent is sufficiently provided to the blood, the staining patch PA is separated from the reaction region (S320). In this case, the staining reagent that has reacted with the target substance in the blood may remain in the reaction region while being bound to the target substance, and a residual staining reagent that has not been bound to the target substance may be re-absorbed into the staining patch PA.

Specifically, as the patch PA containing the staining reagent is separated from the plate PL, the staining reagent that has been moved to the plate PL without being bound to the blood may be absorbed into the staining patch PA and removed from the plate PL. Here, the absorption of the residual staining reagent into the staining patch PA may be performed through the residual staining reagent remaining in the water film WF that has been formed by contact between the staining patch PA and the plate PL and through the water film WF being moved along with the staining patch PA when the staining patch PA is separated from the plate PL.

In this process, at least a part of staining reagent may remain in the blood without being absorbed into the staining patch PA. The remaining staining reagent may be removed from the reaction region by the buffer patch or the washing patch being brought into contact with the remaining staining reagent and being separated therefrom.

Of course, since the residual staining reagent is removed from the plate PL just by separation of the staining patch PA, the washing process and the buffering process which are essentially required in performing staining for a conventional blood test may also be omitted. In other words, according to the present embodiment, a washing process for removing the remaining staining reagent from the plate PL using the washing solution may be omitted.

When staining is completed, an image of the reaction region of the plate PL may be acquired to acquire a staining image (S400), and the acquired image may be analyzed to perform a blood test (S500).

The blood testing method by simple staining according to an embodiment of the present application may further include at least one of the smearing of the blood on the plate PL (S100), the fixing of the smeared blood (S120), the washing of the reaction region using the washing patch PA (S600), and the providing of the predetermined environment to the reaction region using the buffer patch PA (S800) described above. Here, Steps S100 and S120 may be performed before Step S200. In addition, Steps S600 and S800 may be performed one or more times between Steps S200 and S400.

The washing of the reaction region using the washing patch PA (S600) may include the washing patch PA coming into contact with the plate PL and absorbing a residue. The absorption of the residue using the washing patch PA may include the washing patch PA coming into contact with the plate PL and absorbing a staining reagent that has not reacted with at least a portion of the fixed blood or various foreign substances present in the reaction region.

Therefore, the washing (S600) may be performed after blood is fixed to the plate PL as described above, before or after the providing of the staining reagent to the reaction region (S300), or both before and after the providing of the staining reagent to the reaction region (S300). Alternatively, the washing (S600) may also be performed before or after the image acquisition (S400) or both before and after the image acquisition (S400).

The providing of the predetermined environment to the reaction region using the buffer patch PA (S800) may include the buffer patch PA coming into contact with the plate PL and facilitating a reaction between the staining reagent and a target substance in the blood. The buffer patch PA may be used after the providing of the staining reagent (S300), and when the buffer patch PA comes into contact with the reaction region, a water film WF that has the buffer solution contained in the buffer patch PA as a main component may be formed on the plate PL and the patch PA, the water film may provide an optimal pH for the reaction between the staining reagent and the target substance, and the staining reagent and the target substance may react under the optimal pH condition in the water film. Accordingly, staining of the target substance by the staining reagent may be facilitated.

Here, although the buffering (S800) and the washing (S600) have been described as being separately performed by the buffer patch PA and the washing patch PA above, the two steps may also be performed together with a single patch PA having the washing function and the buffering function.

According to the present embodiment, the staining of blood, the washing of the reaction region, the providing of a predetermined environment to the reaction region, and the like may not necessarily be performed using the patch PA. In other words, some of the processes may be performed using a solution required for a corresponding process instead of using the patch PA. For example, the washing of the reaction region may be performed by spraying a washing solution on the reaction region instead of contacting the washing patch PA with the reaction region.

In the present embodiment, when the staining of blood, the washing of the reaction region, the providing of a predetermined environment to the reaction region, and the like are performed by contacting the patch PA with the blood, the corresponding processes may be completed with a smaller amount of solution or reagent in comparison to when performing the corresponding processes by directly spraying the solution and an economical advantage may be obtained. Also, since, according to the present embodiment, it is easier to control a degree of staining reaction, a degree of washing, and a degree of buffering in comparison to directly spraying various solutions contained in the patch PA to the plate PL and an over-reaction may be prevented, the corresponding processes may be more precisely performed, and staining quality may be improved as a result.

Figure 50:
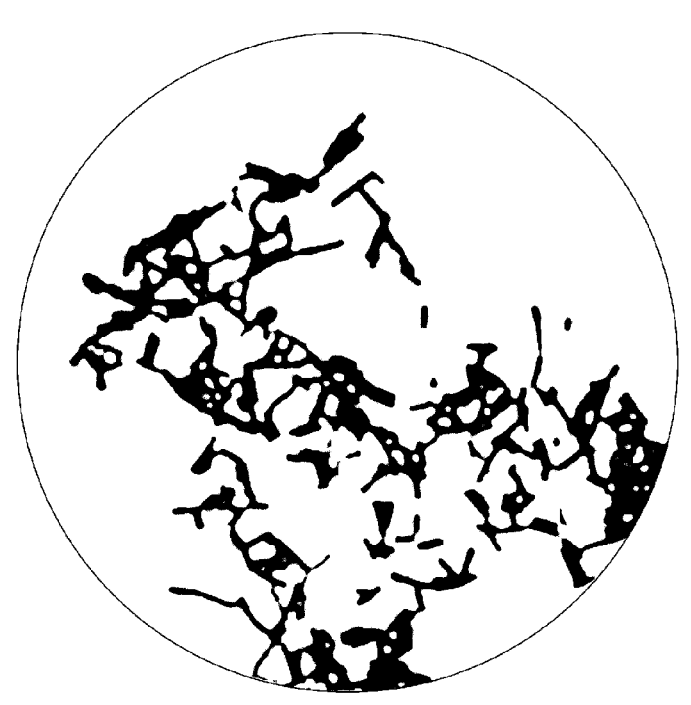
FIGS. 50 to 53 are views of images acquired in the blood testing method using a simple stain according to the present application.
Figure 51:
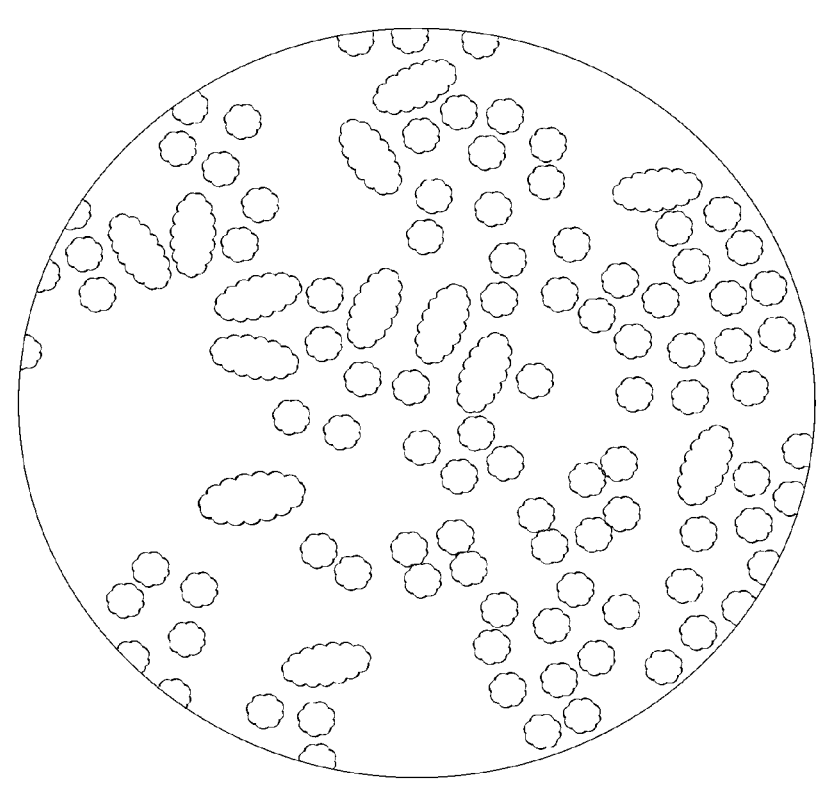
Figure 52:
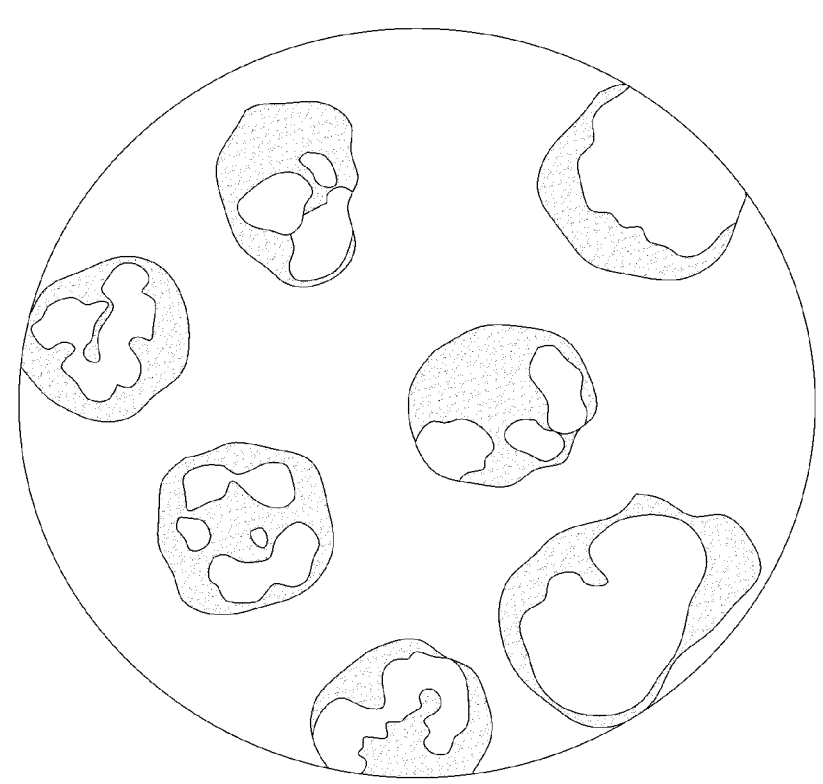

FIGS. 50 to 52 are views related to images acquired in the blood testing method by simple staining according to the present application.

The above-described simple staining may be generally used to detect bacteria in blood or check a degree of bacterial infection, a degree of bacterial growth, and the like. Referring to FIG. 50, when crystal violet is used as a staining reagent, colon bacillus in blood may be stained. Referring to FIG. 51, when methylene blue is used as a staining reagent, *Corynebacterium diphtheriae* in blood may be stained. In order to detect bacteria as above, a basic staining reagent for staining a nucleus may be used mostly to distinguish between bacteria and red blood cells in blood. However, embodiments are not necessarily limited thereto, and an acidic staining reagent or a neutral staining reagent may also be used in accordance with a staining target.

Figure 53:
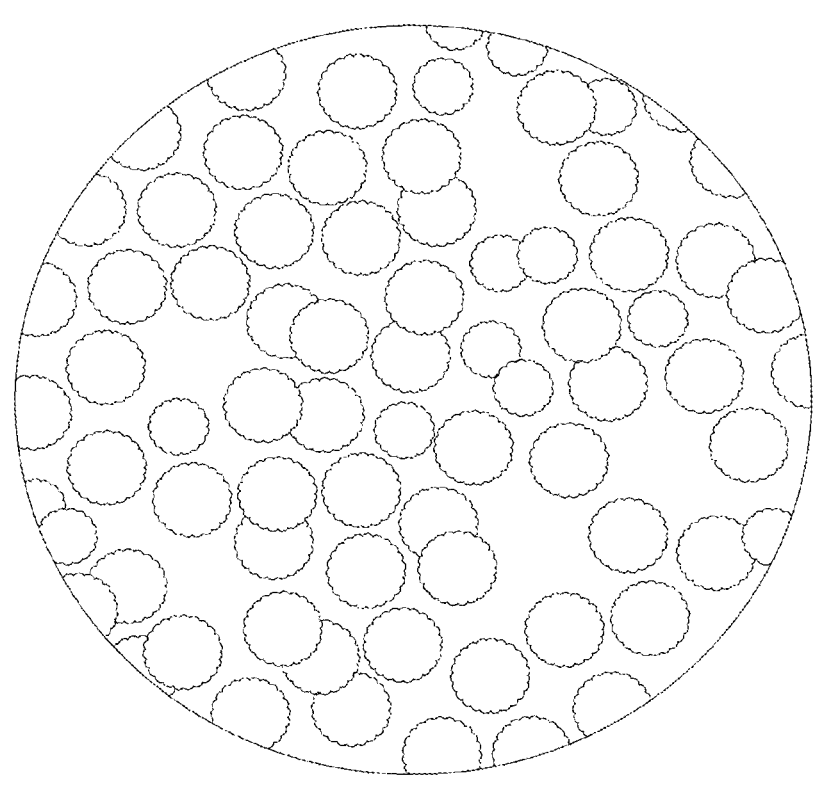

In addition, the above-described simple staining may also be used for the CBC. Referring to FIG. 52, when methylene blue is used as a staining reagent, white blood cells in blood may be stained. In this way, the number of white blood cells in blood may be quantified. Referring to FIG. 53, when eosin is used as a staining reagent, blood cells in blood may be stained. In this case, cytoplasm of red blood cells or platelets, as well as white blood cells, are all stained, and different blood cells may be distinguished through an image analysis on the basis of morphologies or sizes of blood cells. When different blood cells are distinguished, each type of blood cells in blood may be quantified. Accordingly, the CBC may be completed.

Embodiments of patches PA that may be used in a blood test according to the present embodiment will be described below. Each patch PA will be described as containing a few components, and each component may be understood as the above-described base substance BS or additive substance AS. However, the components which will be described as being able to be contained in each patch PA do not represent all components contained in each patch PA, and each patch PA may also contain other unmentioned components.

4.5.1.1 Staining Patch

A blood test of the present application may be performed using a staining patch PA that contains a staining reagent. In other words, the patch PA may contain a staining reagent that reacts with a target substance in blood and stains the target substance and may deliver the staining reagent to the plate PL.

The staining reagent may be the additive substance AS contained in the patch PA. In other words, the patch PA may contain a solution including the staining reagent. The patch PA in which the staining reagent is contained may also contain, in addition to the staining reagent or a solution containing the staining reagent, a base substance BS or additive substance AS that allows the staining reagent to easily bind to a target substance in blood.

The staining reagent may be a substance that mostly electrochemically binds to the target substance and develops color. Examples of the staining reagent include a basic staining reagent, a neutral staining reagent, and an acidic staining reagent. Since the examples have been described in detail above, the detailed description thereof will be omitted.

When, as in the present embodiment, the staining reagent is contained in the patch PA and provided to the plate PL, a portion of the staining reagent that has not reacted with blood fixed to the plate PL may be re-absorbed into the patch PA. Accordingly, the washing process may be omitted, the patch PA may be reused in some cases, and prompt and efficient diagnosis may be realized.

The patch PA according to an embodiment of the present application may be a staining reagent containing patch PA that includes a staining reagent configured to react with a target substance and a mesh structural body NS that is provided in a mesh structure forming micro-cavities in which the staining reagent is contained and configured to come into contact with a reaction region in which blood is placed so that a portion of the contained staining reagent is provided to the reaction region.

4.5.1.2 Washing Patch

A blood testing method according to the present embodiment may be performed using a washing patch PA configured to absorb a residue. In other words, in the blood testing method according to the present embodiment, the residue may be absorbed by the washing patch PA being brought into contact with the plate PL and being separated therefrom. The residue may refer to a residue that is not absorbed into each patch PA and removed when the above-described staining patch PA is brought into contact with the plate PL and then separated therefrom.

The washing patch PA may contain a washing solution. The washing solution may include a TBS or PBS with Tween 20 added to a portion thereof. The washing solution may be provided as a solution in which the residue may be dissolved in accordance with a residue to be absorbed. The patch PA containing the washing solution may further contain the base substance BS or additive substance AS that assists in the washing.

By the patch PA containing the washing solution and being brought into contact with the plate PL and then separated therefrom, impurities or residue on the plate PL, for example, a staining reagent that has not been bound or other foreign substances may be absorbed into the washing patch PA and removed.

In the absorption of the residue into the washing patch PA, the washing patch PA may come into contact with the plate PL, that is, the plate PL region on which blood is placed, so that the water film WF is formed, and the residue may be dissolved in the water film WF. The residue dissolved in the water film WF may be absorbed into the washing patch PA when water film WF is separated from the plate PL and moved along with the washing patch PA. 4.5.1.3 Buffer patch.

A blood testing method according to the present embodiment may be performed using a buffer patch. In other words, the buffer patch PA may contain a buffer solution and provide a predetermined environment to the plate PL. The buffer patch PA may contain a buffer solution that facilitates each step of the blood test. The buffer solution may mostly be a buffer solution having an optimal pH required for a desired basic reaction.

4.5.2 Reference Embodiment 2—Romanowsky Stain

A blood test according to an embodiment of the present application may be performed by a Romanowsky staining technique using the plate PL and the patch PA.

Figure 54:
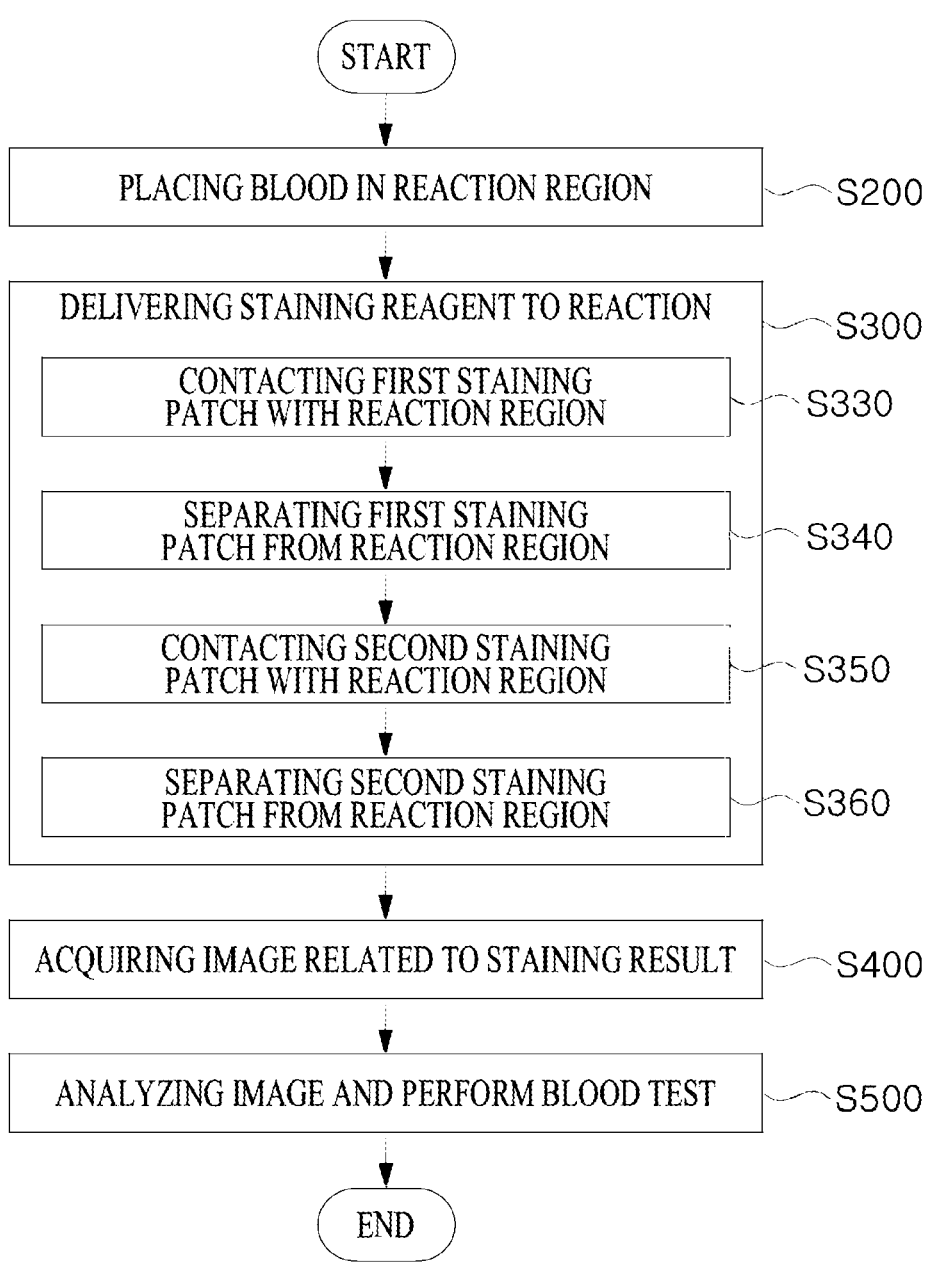
FIG. 54 illustrates a flowchart for describing a blood testing method using a Romanowsky stain as another example of a blood testing method according to the present application.

FIG. 54 illustrates a flowchart for describing a blood testing method by Romanowsky staining as another example of a blood testing method according to the present application.

The blood testing method by Romanowsky staining according to an embodiment of the present application may include placing blood in a reaction region (S200), providing a staining reagent to the reaction region (S300), acquiring an image related to a staining result (S400), and analyzing the image to perform a blood test (S500).

The providing of the staining reagent (S300) in the blood test by Romanowsky staining includes providing at least two or more staining reagents to the blood. In the present embodiment, this may be performed mostly using a plurality of staining patches PA that each contain one of a plurality of staining reagents. However, for convenience of description, description will be given below on the basis of using two staining patches PA, i.e., a first staining patch PA and a second staining patch PA, to stain the blood using two staining reagents. However, in the present embodiment, the number of staining patches PA is not limited to two, and three or more staining patches PA may also be used. In the following description, since a modified example in which three or more staining patches PA are used may be applied without inventiveness of those of ordinary skill in the art, the modified example should be understood as belonging to the present embodiment.

The providing of the staining reagent (S300) may include first bringing a first staining patch PA that contains the staining reagent into contact with the reaction region on a plate PL such as a slide glass (S330), bringing a second patch PA into contact with the reaction region so that a second staining reagent is movable to the reaction region (S350), and separating the first patch PA from the reaction region (S360).

Figure 55:
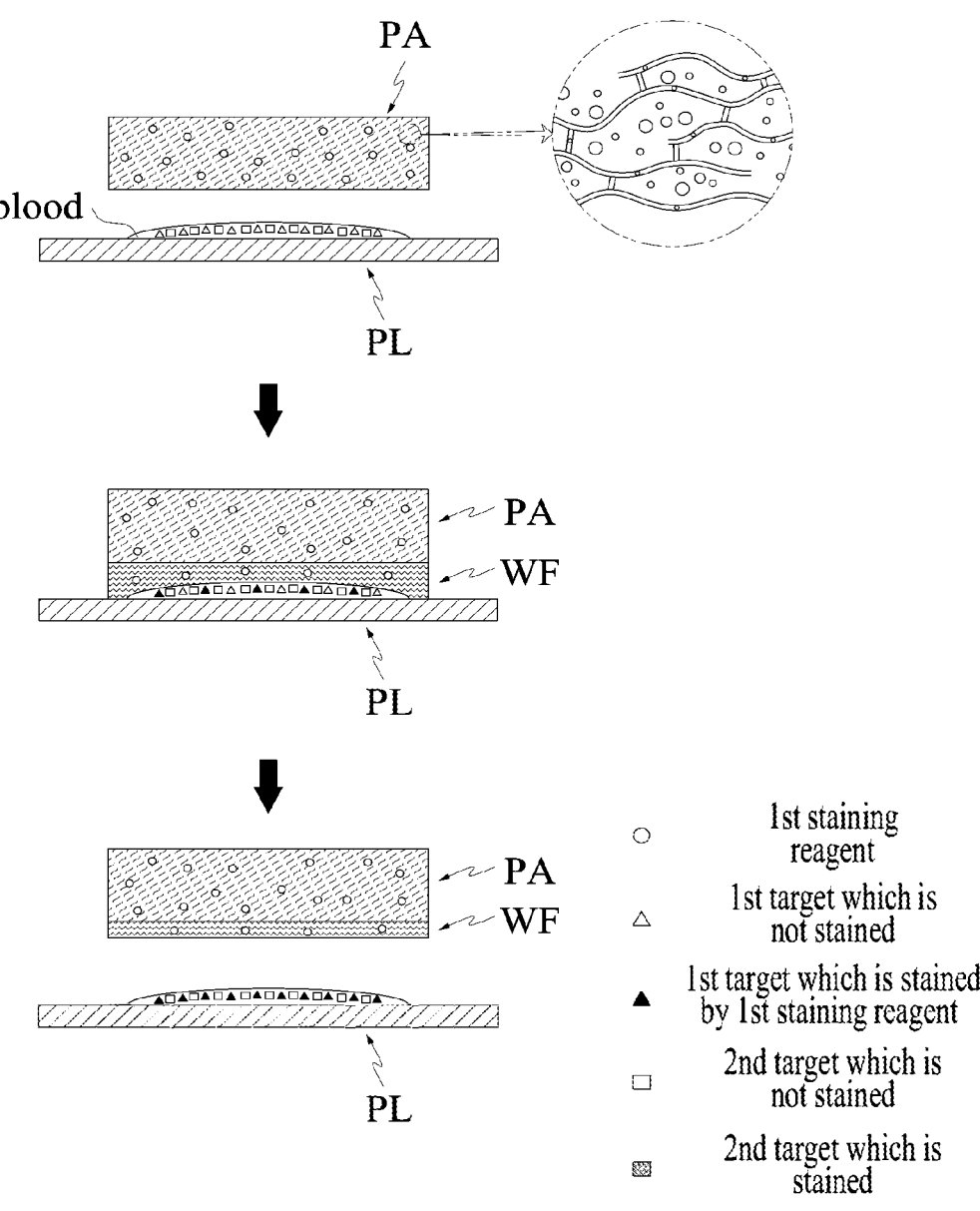
FIG. 55 is a view illustrating a process in which a first staining reagent is provided in the blood testing method using a Romanowsky stain according to the present application.
Figure 56:
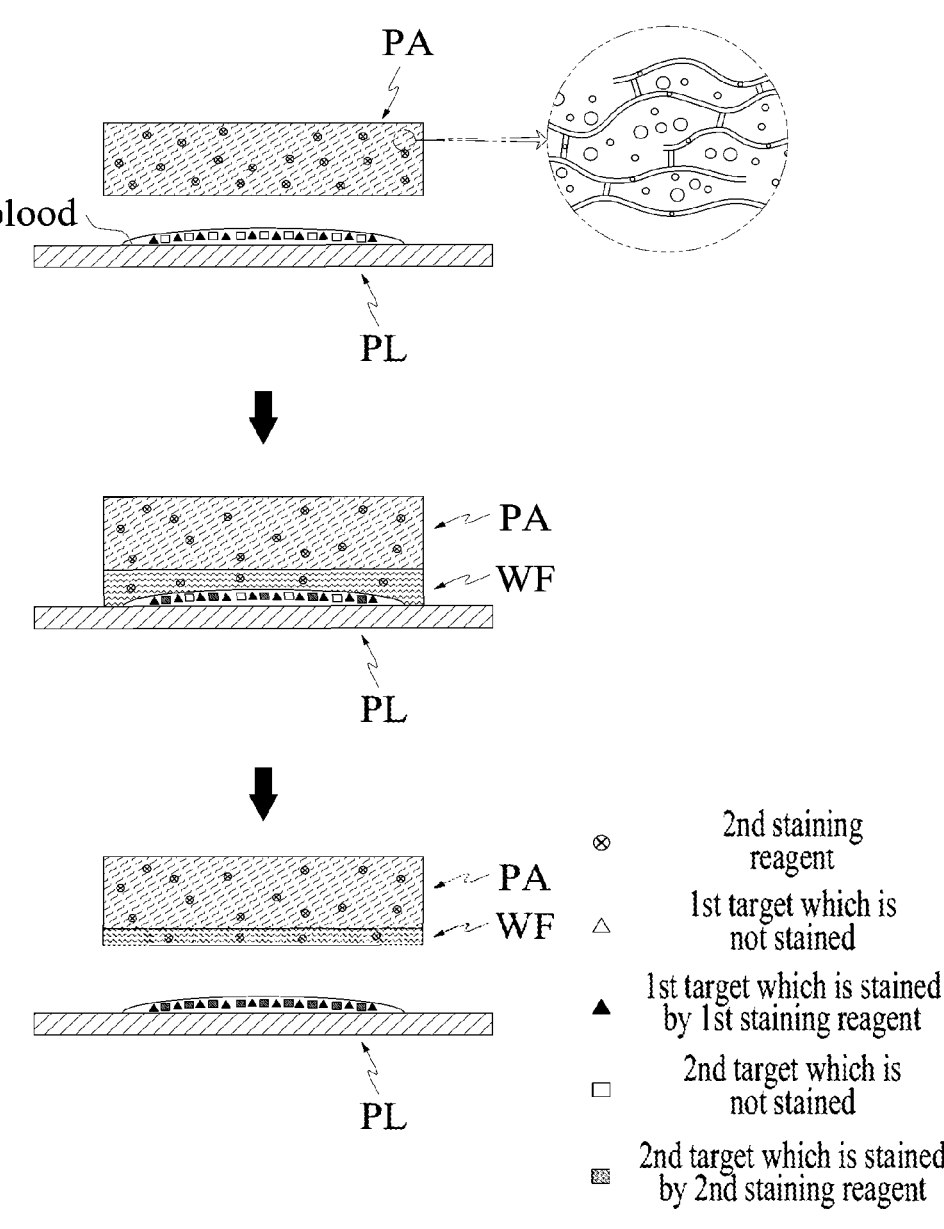
FIG. 56 is a view illustrating a process in which a second staining reagent is provided in the blood stain method using a Romanowsky stain according to the present application.

FIG. 55 is a view illustrating a process in which a first staining reagent is provided in the blood testing method by Romanowsky staining according to the present application, and FIG. 56 is a view illustrating a process in which a second staining reagent is provided in the blood testing method by Romanowsky staining according to the present application.

Referring to FIGS. 55 and 56, a first staining patch PA contains a first staining reagent and provides the staining reagent to blood placed on the plate PL (S330). Then, when the first staining reagent is sufficiently provided to the blood, the first staining patch PA is separated from the reaction region (S340). Next, the second staining patch PA contains a second staining reagent and provides the staining reagent to the blood placed on the plate PL (S350). Then, when the second staining reagent is sufficiently provided to the blood, the second staining patch PA is separated from the reaction region (S360).

Here, the first staining reagent and the second staining reagent may stain different target substances in blood. For example, the first staining reagent may be any one of a basic staining reagent that stains a nucleus and an acidic staining reagent that stains a cytoplasm, and the second staining reagent may be the other, or vice versa. Specifically, the first staining reagent may be methylene blue, and the second staining reagent may be eosin. Of course, it should be noted that the types of the first staining reagent and the second staining reagent are not limited to the above-mentioned examples.

Referring again to FIG. 55, when the first staining patch PA comes into contact with the reaction region, the first staining reagent may stain a first target substance. Referring again to FIG. 56, when the second staining patch PA comes into contact with the reaction region, the second staining reagent may stain a second target substance. Here, the first target substance may be any one of a nucleus and a cytoplasm, and the second target substance may be the other one of the nucleus and the cytoplasm.

Since the process in which the staining reagent stains a target substance has already been described with respect to Step S310, detailed description thereof will be omitted.

Referring again to FIGS. 55 and 56, in a process in which each of the first staining patch PA and the second staining patch PA is separated from the reaction region, a water film WF formed in the vicinity of a contact region is absorbed into the staining patch PA. In this case, the residual staining reagent that remains in the blood without reacting may also be absorbed into the staining patch PA. Since the absorption of the remaining staining reagent by the staining patch PA has already been described above with respect to Step S320, the detailed description thereof will be omitted.

When staining is completed, an image of the reaction region of the plate PL is acquired to acquire a staining image (S400), and the acquired image is analyzed to perform a blood test (S500).

The blood testing method by simple staining according to an embodiment of the present application may further include at least one of the smearing of the blood on the plate PL (S100), the fixing of the smeared blood (S120), the washing of the reaction region using the washing patch PA (S600), and the providing of the predetermined environment to the reaction region using the buffer patch PA (S800) described above. Here, Steps S100 and S120 may be performed before Step S200. In addition, Steps S600 and S800 may be performed one or more times between Steps S200 and S400.

The washing of the reaction region using the washing patch PA (S600) may include contacting the washing patch PA with the plate PL and absorbing a residue. This step has already been described with respect to the blood testing method by simple staining according to the present disclosure. However, in the present embodiment, the washing (S600) may be performed between the separating of the first staining patch PA from the reaction region (S340) and the contacting of the second staining patch PA with the reaction region (S350), after the separating of the second staining patch PA from the reaction region (S360), or at both time points.

The providing of the predetermined environment to the reaction region using the buffer patch PA (S800) may include contacting the buffer patch PA with the plate PL and facilitating a reaction between the staining reagent and a target substance in the blood.

The present Step S800 may be performed using two patches PA, a first buffer patch PA that contains a first buffer solution having an optimal pH for a staining reaction of the first staining reagent and a second buffer patch PA that contains a second buffer solution having an optimal pH for a staining reaction of the second staining reagent. That is, Step S800 may include providing a first environment for first staining by the first staining reagent using the first buffer patch PA (S810) and providing a second environment for second staining by the second staining reagent using the second buffer patch PA (S820). Here, the first buffer step (S810) and the second buffer step (S820) may be performed respectively after the separation of the first staining patch PA (S340) and the separation of the second staining patch (S360).

Alternatively, the present Step S800 may also be performed through a single buffer patch PA. In this case, buffering (800) may be performed during at least one time point of time points after Steps S340 and S360.

Here, although the buffering (S800) and the washing (S600) have been described as being separately performed by the buffer patch PA and the washing patch PA, respectively, the two steps may also be performed together with a single patch PA having the washing function and the buffer function.

Figure 57:
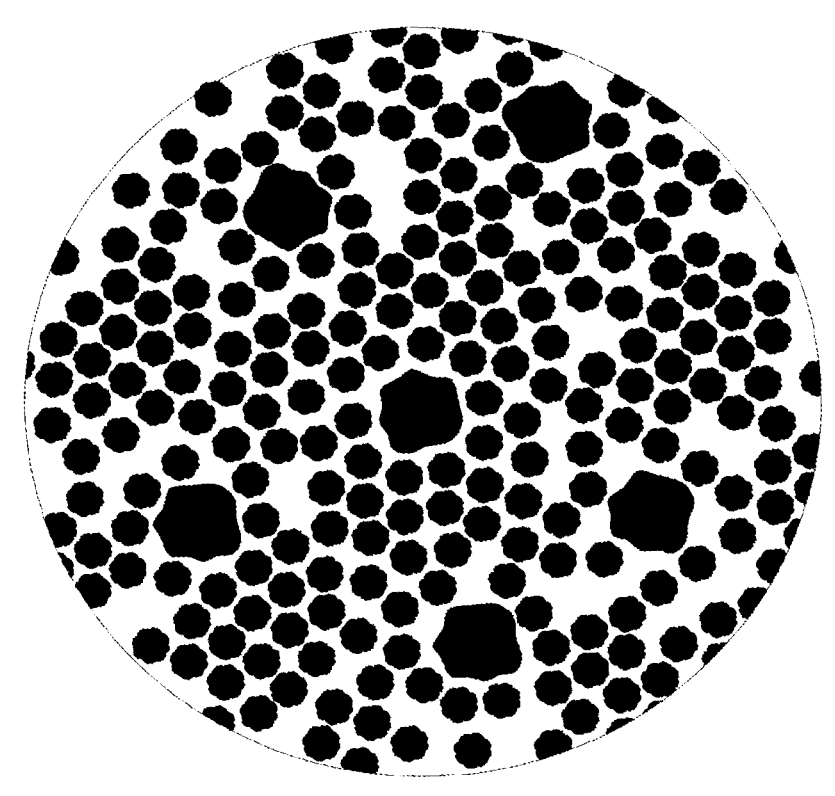
FIGS. 57 and 58 are views of images acquired in the blood testing method using a Romanowsky stain according to the present application.
Figure 58:
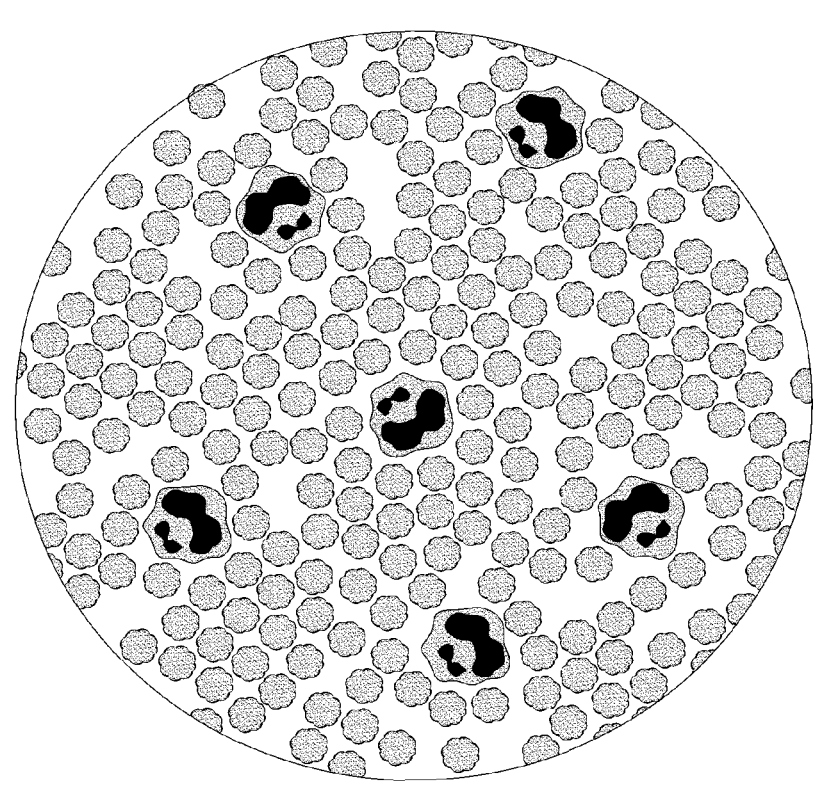

FIGS. 57 and 58 are views related to images acquired in the blood testing method by Romanowsky staining according to the present application.

Comparing FIGS. 57 and 58, FIG. 57 relates to a result of staining performed without the buffering (S800), and FIG. 58 relates to a result of staining performed with the buffering (S800) after Step S360. Since blood staining quality may be degraded due to precipitation between staining reagents when two staining reagents are used, it may be preferable for the buffering (S800) to be performed after Step S360 in which two or more staining reagents are present in the reaction region.

Figure 59:
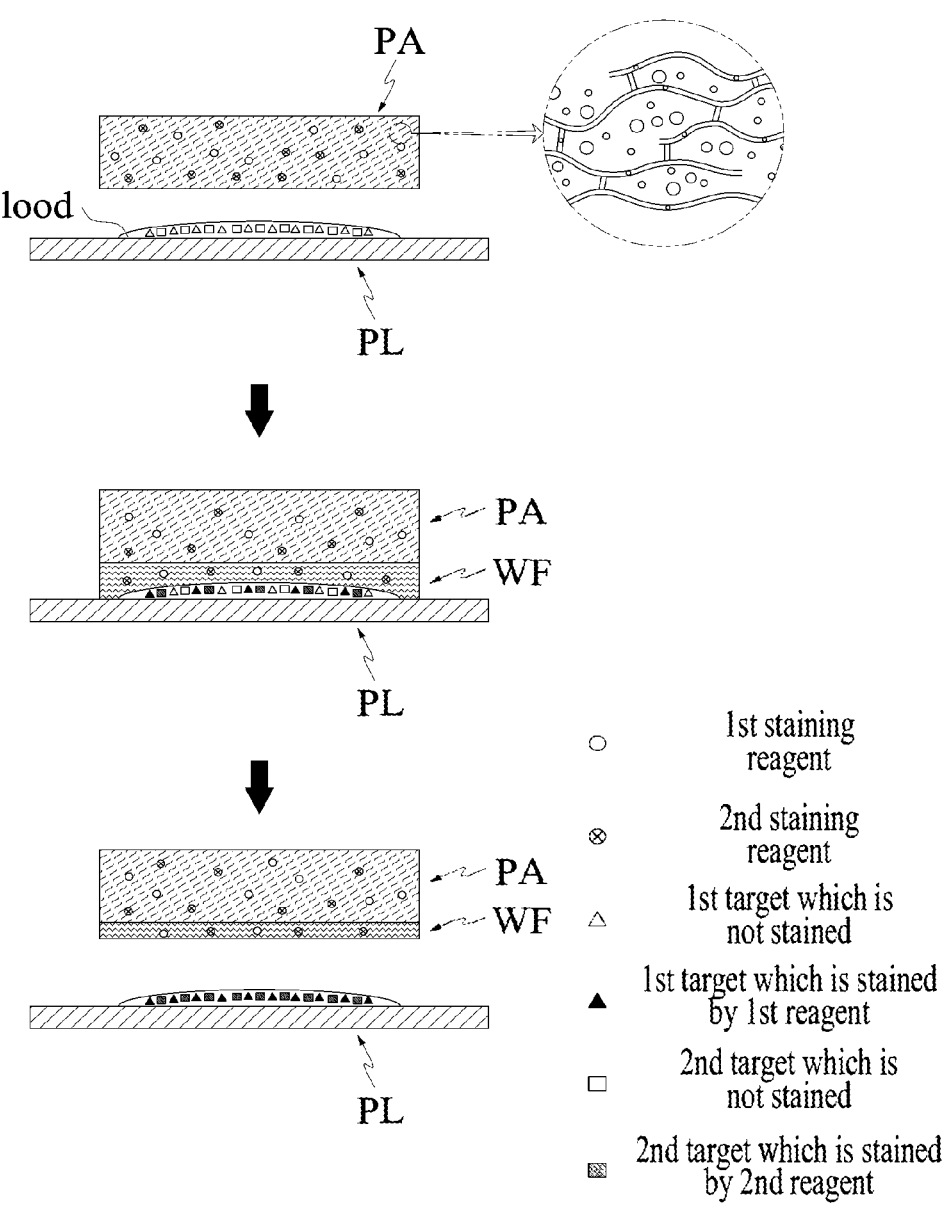
FIG. 59 is a view illustrating a process in which a first staining reagent and a second staining reagent are provided together in the blood testing method using a Romanowsky stain according to the present application.

FIG. 59 is a view illustrating a process in which a first staining reagent and a second staining reagent are provided together in the blood testing method by Romanowsky staining according to the present application.

It has been described above that the blood test is performed using a plurality of staining patches PA, each including one of a plurality of staining reagents. However, only a single staining patch PA may be used even when staining of blood requires a plurality of staining reagents, as shown in FIG. 59.

For example, although a first staining patch PA that contains methylene blue and a second staining patch PA that contains eosin may be used as in the present embodiment to perform Romanowsky staining using methylene blue and eosin, instead, a Giemsa solution, a Wright solution, or the like in which methylene blue and eosin are mixed may be contained in a single staining patch PA, and then blood may be stained similarly as simple staining.

However, in such a case, since precipitation may occur between staining reagents contained in the patch PA upon staining, it may be preferable for buffering process to be performed after staining.

Although it has been described above that the plurality of patches PA each contain only a single staining substance, unlike this, at least one of the plurality of patches PA may contain a plurality of staining substances. For example, a Wright solution may be contained in the first staining patch and a Giemsa solution may be contained in the second staining patch to perform Wright-Giemsa staining, and the Wright-Giemsa staining may be performed by each step according to the present embodiment being performed.

Although the present embodiment has been described above on the basis of the Romanowsky staining technique, it should be noted that the present embodiment may be universally used for a staining technique in which at least two or more staining substances are used.

In the present embodiment, it is not always necessary for the staining of blood, the washing of the reaction region, the providing of a predetermined environment to the reaction region, and the like to be performed using patches PA. In other words, some of the processes may be performed using solutions required for the corresponding processes instead of using the patches PA. For example, the first staining may be performed using a staining solution that accommodates the first staining reagent, and the second staining may be performed using the second staining patch PA.

In the present embodiment, when the staining of blood, the washing of the reaction region, the providing of a predetermined environment to the reaction region, and the like are performed by bringing the patch PA into contact, since the corresponding processes may be completed with a smaller amount of solution or reagent in comparison to when performing the corresponding processes by directly spraying the solution, the present embodiment may be more economical. Also, since, according to the present embodiment, it is easier to control a degree of staining reaction, a degree of washing, and a degree of buffering in comparison to directly spraying various solutions contained in the patch PA on the plate PL and thus an over-reaction may be prevented, the corresponding processes may be more precisely performed, and staining quality may be improved as a result.

4.5.3 Reference Embodiment 3—Gram Stain

A blood test according to an embodiment of the present application may be performed by a Gram staining technique using a plate PL and a patch PA.

FIG. 60 is a flowchart for describing a blood testing method by Gram staining as yet another example of a blood testing method according to the present application.

The blood testing method by Gram staining according to an embodiment of the present application may include placing blood in a reaction region (S200), providing a staining reagent to the reaction region (S300'), acquiring an image related to a staining result (S400), and analyzing the image to perform a blood test (S500).

The providing of the staining reagent (S300') in the blood test by Gram staining may include providing a main staining reagent, a mordanting reagent, a decolorizing reagent, and a contrast staining reagent to the blood. In the present embodiment, this may be performed mostly using a plurality of patches PA that each contain at least one of the main staining reagent, the mordanting reagent, the decolorizing reagent, and the contrast staining reagent.

Here, the plurality of patches PA may each contain a single reagent related to Gram staining. For example, the patches PA may include a main staining patch PA that contains the main staining reagent, a mordanting patch PA that contains the mordanting reagent, a decolorizing patch PA that contains the decolorizing reagent, and a contrast staining patch PA that contains the contrast staining reagent.

Here, some of the reagents related to Gram staining may be provided to the reaction region in forms in which solutions are directly sprayed instead of being provided on the reaction region in forms of being contained in the patches PA. For example, the decolorizing process may be performed by spraying a decolorizing agent on blood instead of bringing a patch PA that contains the decolorizing agent in contact with the reaction region. When the staining process is carried out by spraying a solution instead of bringing the patch PA into contact, some specific steps of Step S300 which will be described below may be changed into a solution spraying step.

Here, at least some of the plurality of patches PA may contain a plurality of reagents related to Gram staining. However, the Gram staining should be performed in the order of main staining, mordanting, decolorizing, and contrast staining, wherein mordanting and decolorizing should be performed sequentially. In consideration of the above, for example, the main staining reagent and the mordanting reagent may be contained together in a single patch PA.

However, for convenience of description, description will be given below on the basis of a case in which the plurality of patches PA each include a single reagent related to Gram staining.

In relation to the Gram staining, the providing of the staining reagent (S300') may include first contacting a main staining patch PA t with a reaction region on a plate PL such as a slide glass (S310'), separating the main staining patch PA from the reaction region (S320'), bringing a mordanting patch PA into contact with the reaction region (S330'), separating the mordanting patch PA from the reaction region (S340'), bringing a decolorizing patch PA into contact with the reaction region (S350'), separating the decolorizing patch PA from the reaction region (S360'), bringing a contrast staining patch PA into contact with the reaction region (S370'), and separating the contrast staining patch PA from the reaction region (S380').

Figure 61:
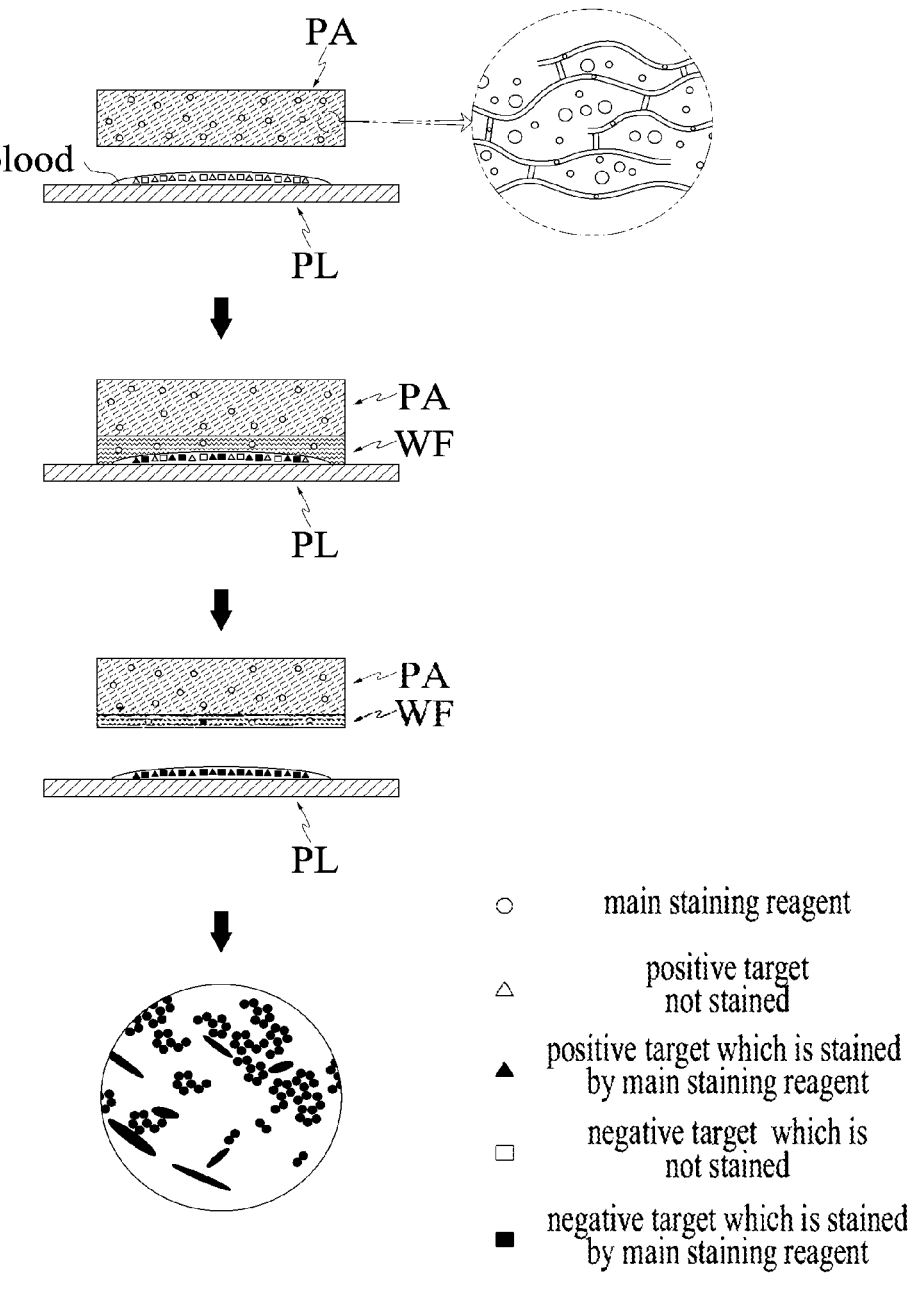
FIGS. 61 to 63 are views illustrating main staining, mordanting, decolorizing, and contrast staining processes in the blood testing method using a Romanowsky stain according to the present application.
Figure 62:
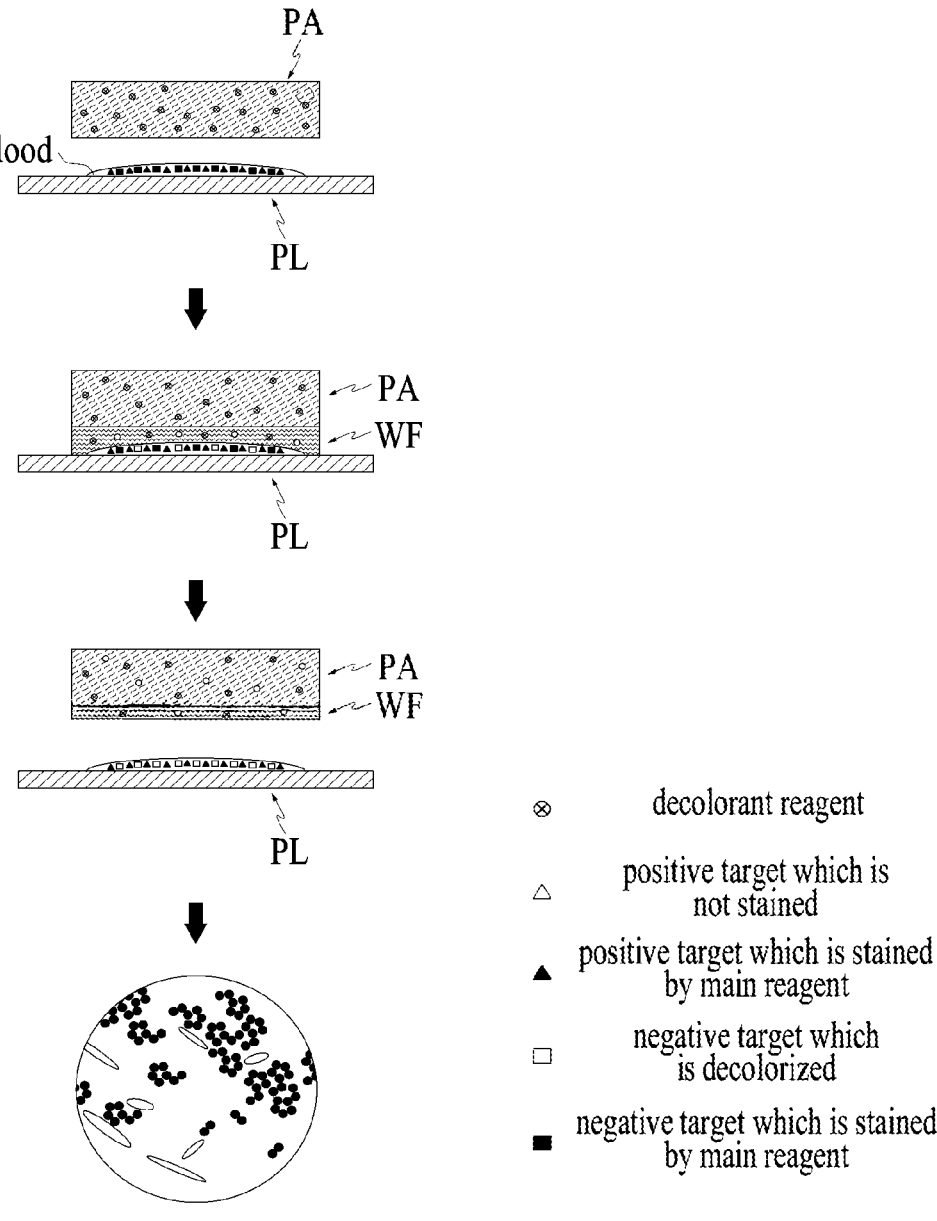
Figure 63:
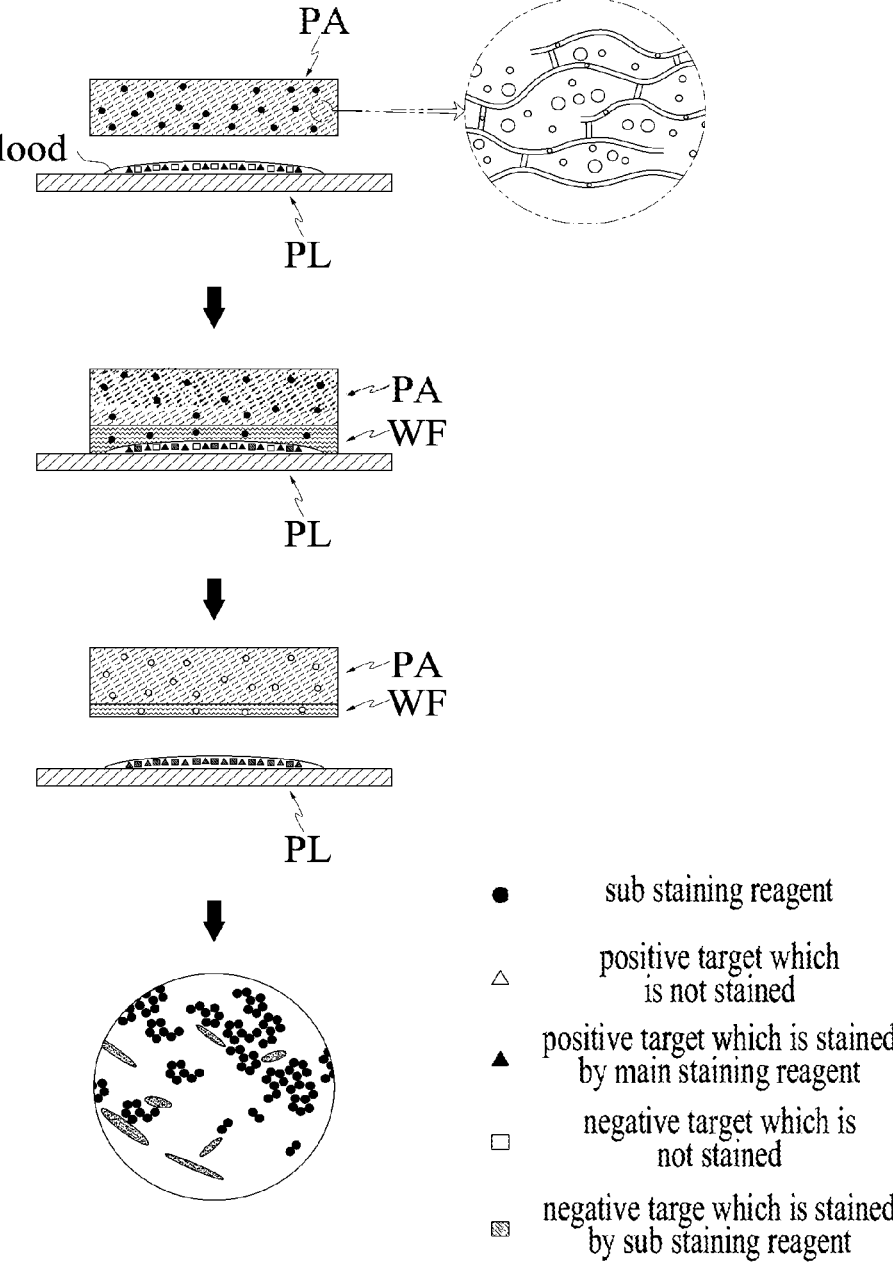

FIGS. 61 to 63 are views illustrating main staining, mordanting, decolorizing, and contrast staining processes in the blood testing method by Romanowsky staining according to the present application.

Referring to FIG. 61, the main staining patch PA is brought into contact with the reaction region (S310'), a main staining reagent is provided to the blood, and the main staining patch PA is separated from the reaction region (S310'). The main staining reagent provided to the blood through a water film WF between the reaction region and the patch PA may stain substances which are both positive and negative to the main staining reagent. For example, the main staining agent of Gram staining may stain Gram-positive bacteria and Gram-negative bacteria violet.

The mordanting patch PA is brought into contact with the reaction region (S330'), a mordanting reagent is provided to the blood, and the mordanting patch PA is separated from the reaction region (S340'). The mordanting reagent provided to the blood through a water film WF between the reaction region and the patch PA may strengthen binding between the main staining reagent and a substance positive to the main staining reagent or, conversely, weaken binding between the main staining reagent and a substance negative to the main staining reagent. For example, in Gram staining, the mordanting agent may strength binding between a Gram main staining agent and Gram-positive bacteria. Since there is a case in which a positive substance is not decolorized due to a decolorizing reagent, even when the positive substance is not mordanted in accordance with a type of staining technique, Steps S330' and S340' are not essential.

Referring to FIG. 62, the decolorizing patch PA is brought into contact with the reaction region (S350'), a decolorizing reagent is provided to the blood, and the decolorizing patch PA is separated from the reaction region (S360'). The decolorizing reagent provided to the blood through a water film WF between the reaction region and the patch PA decolorizes a substance negative to the main staining reagent. That is, the decolorizing reagent may separate the main staining agent from a substance negative to the main staining agent.

Referring to FIG. 63, the contrast staining patch PA is brought into contact with the reaction region (S370'), a contrast staining reagent is provided to the blood, and the contrast staining patch PA is separated from the reaction region (S380'). The contrast staining reagent provided to the blood through a water film WF between the reaction region and the patch PA binds to a substance negative to the main staining reagent and stains the negative substance. For example, a Gram contrast staining reagent may stain Gram-negative bacteria red. Since there is a case in which only substances positive to main staining are attempted to be observed in accordance with a type of staining technique, Steps S370' and S380' are not essential.

When staining is completed, an image of the reaction region of the plate PL may be acquired to acquire a staining image (S400), and the acquired image may be analyzed to perform a blood test (S500).

The blood testing method by simple staining according to an embodiment of the present application may further include at least one of the smearing of the blood on the plate PL (S100), the fixing of the smeared blood (S120), the washing of the reaction region using the washing patch PA (S600), and the providing of the predetermined environment to the reaction region using the buffer patch PA (S800) described above.

Here, Steps S600 and S800 may be performed after Step S300. More specifically, Steps S600 and S800 may be performed during at least one time point of time points between Steps S310' and S380' and after Step S380'.

4.6 Embodiment of Blood Test Device

A blood test of the present application may be performed using a blood test device.

Figure 64:
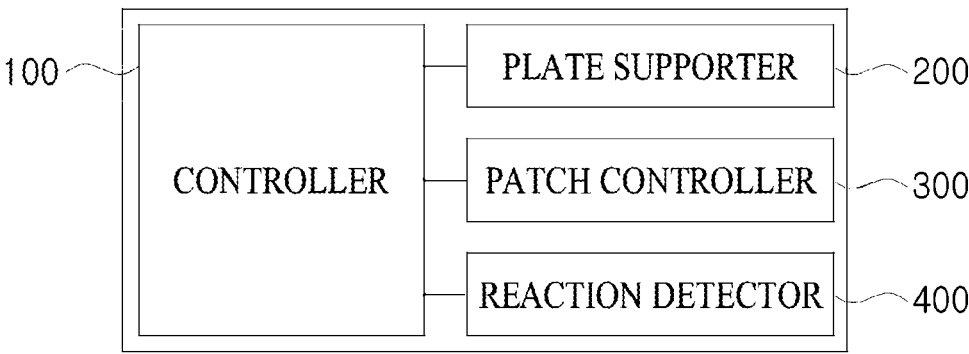
FIG. 64 illustrates an embodiment of a blood test device according to the present application.

FIG. 64 illustrates a blood test device 10 according to an embodiment of the present application.

The blood test device according to an embodiment of the present application may include a plate supporter 200, a patch controller 300, and an imaging device 400. The blood test device according to the present embodiment may include a mesh structural body NS forming micro-cavities, and using a patch in which a liquid substance SB may be contained in the micro-cavities, blood may be stained and a staining image may be acquired.

The plate supporter 200 may support a plate PL on which a sample SM to be diagnosed is placed on a reaction region.

The patch controller 300 may use at least one or more of the above-described patches PA used in the blood testing method according to an embodiment of the present disclosure and control positions of the patches PA relative to the reaction region so that a staining reagent is provided to the reaction region.

The imaging device 400 may acquire an image of the reaction region and acquire an image related to stained blood.

Specifically, the imaging device 400 may include an image acquisition module. Here, the image acquisition module may include a camera module.

Accordingly, the imaging device 400 may acquire partial images of the reaction region, respectively. Also, the imaging device 400 may combine the partial images.

The blood test device may further include a controller 100.

At least one of an image analysis program and a blood test program may be installed in the controller 100, and by operating a program installed therein, the controller 100 may determine a type of blood cells, presence of bacteria, and the like from an image of stained blood, count the number of blood cells and bacteria, generate numerical or morphological information on the blood cells or information on the presence of bacteria and numerical or morphological information on the bacteria on the basis of determined results, and finally determine a testee's health condition, presence of illness, progress of disease, or the like.

Figure 65:
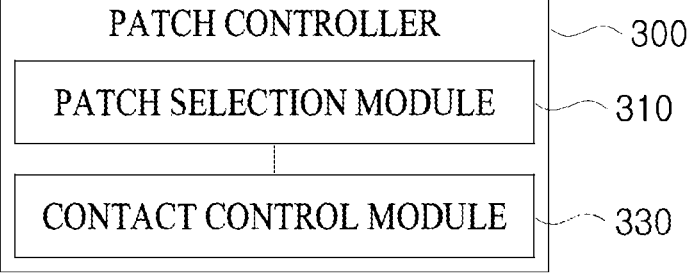
FIG. 65 illustrates an example of a patch controller in the embodiment of the blood test device according to the present application.

FIG. 65 illustrates an example of the patch controller 300 in an embodiment of the blood test device 10 according to the present application.

In the blood test device 10 according to an embodiment of the present application, the patch controller 300 may include a patch selection module 310 and a contact control module 330.

The patch selection module 310 may select a patch PA to be controlled. The selection of the patch PA to be controlled by the patch selector may include selecting one or more staining patches PA that contain a staining reagent or various patches PA that contain a fixing solution, a washing solution, a decolorizing agent, a mordanting agent, or a buffer solution.

The contact control module 330 may control a state of contact between a selected patch PA and the reaction region. The controlling of the contact state may include controlling a position of the patch PA relative to the reaction region.

The above description is merely illustrative of the technical spirit of the present disclosure, and those of ordinary skill in the art to which the present disclosure pertains should be able to make various modifications and changes within a scope not departing from essential characteristics of the present disclosure.

Therefore, the above-described embodiments of the present disclosure may also be implemented separately or in combination.

The embodiments disclosed herein are for describing the technical spirit of the present disclosure instead of limiting the same, and the scope of the technical spirit of the present disclosure is not limited by such embodiments. The scope of the present disclosure should be interpreted on the basis of the claims below, and all technical spirits within the equivalent scope should be interpreted as belonging to the scope of the present disclosure.

The invention claimed is:

1. A blood testing method for performing hematological analysis through staining of staining targets using at least one staining gel patch, wherein the staining gel patch is three-dimensional gel matrix containing at least one staining reagent for staining the staining targets present in blood, the blood testing method comprising:

smearing blood on a plate;

fixating the blood on the plate; and providing the staining reagent to the plate using the staining gel patch, wherein the providing the staining reagent to the plate using the staining gel patch includes:

delivering the staining reagent to the plate by contacting the staining gel patch containing the staining reagent to the plate; and washing a residual staining reagent that has not reacted with the staining targets among the delivered staining reagent from the plate by lifting the residual staining reagent along with patch, wherein the staining target are blood cells, parasites or bacteria in the blood wherein the method does not comprise washing step that involves directly spraying a washing solution onto the plate.

2. The blood testing method of claim 1, further comprising acquiring an image of the blood stained by the provided staining reagent.

3. The blood testing method of claim 2, further comprising acquiring at least one of a type information of the blood cells, a count information of the blood cells, and a morphological information of the blood cells on the basis of the image.

4. The blood testing method of claim 3, further comprising performing a complete blood cell count (CBC) on the basis of the acquired information.

5. The blood testing method of claim 1, further comprising acquiring at least one of an information related to presence of the parasites or bacteria, an information related to a type of the parasites or bacteria, an information related to a number of the parasites or bacteria, and a morphological information on the parasites or bacteria.

6. The blood testing method of claim 5, further comprising performing a peripheral blood smear examination on the basis of the acquired information.

7. The blood testing method of claim 1, further comprising absorbing the residual staining reagent and a foreign substance remaining in the plate from the plate using a washing gel patch, wherein the washing gel patch is three-dimensional gel matrix containing a washing liquid.

8. The blood testing method of claim 1, wherein the providing of the staining reagent to the plate using the staining gel patch includes:

using a first staining gel patch, the first staining gel patch being three-dimensional gel matrix containing a first staining reagent for staining any one of a cytoplasm and a nucleus in staining targets and providing the first staining reagent to the plate; and using a second staining gel patch, the second staining gel patch being three-dimensional gel matrix containing a second staining reagent for staining the other one of the cytoplasm and the nucleus in the staining targets and providing the second staining reagent to the plate.

9. The blood testing method of claim 8, further comprising providing an optimal pH for the plate using a first buffer gel patch, wherein the first buffer gel patch is three-dimensional gel matrix containing a first buffer solution having an optimal pH for a staining reaction of the first staining reagent.

10. The blood testing method of claim 9, wherein the providing of the optimal pH is performed during at least one time point of a time point between the providing of the first staining reagent and the providing of the second staining reagent and a time point after the providing of the second staining reagent.

11. The blood testing method of claim 1, wherein:

the staining gel patch contains a first staining reagent staining the cytoplasm of the staining targets and a second staining reagent staining the nucleus of the staining targets; and the providing of the staining reagent to the plate using the staining gel patch includes providing the first staining reagent and the second staining reagent to the plate so that the staining gel patch stains both the cytoplasm and the nucleus of the staining targets.

12. The blood testing method of claim 11, further comprising, after the providing of the first staining reagent and the second staining reagent, providing an optimal pH for the plate using a buffer gel patch, wherein the buffer gel patch is three-dimensional gel matrix containing a buffer solution.

* * * * *